US012410244B2

(12) United States Patent
Downey et al.

(10) Patent No.: US 12,410,244 B2
(45) Date of Patent: *Sep. 9, 2025

(54) ANTI-ALPHA-SYNUCLEIN ANTIBODIES

(71) Applicant: UCB Biopharma SRL, Brussels (BE)

(72) Inventors: Patrick Downey, Brussels (BE); Kerry Louise Tyson, Slough (GB); Marco Kriek, Slough (GB); Lorenzo De Lichtervelde, Brussels (BE); Daniel John Lightwood, Slough (GB); David James Mcmillan, Slough (GB); Peter Charles Elliott, Slough (GB); Terence Seward Baker, Berkshire (GB)

(73) Assignee: UCB Biopharma SRL, Brussels (BE)

( * ) Notice: Subject to any disclaimer, the term of this patent is extended or adjusted under 35 U.S.C. 154(b) by 838 days.

This patent is subject to a terminal disclaimer.

(21) Appl. No.: 17/682,082

(22) Filed: Feb. 28, 2022

(65) Prior Publication Data
US 2022/0340648 A1 Oct. 27, 2022

Related U.S. Application Data

(63) Continuation of application No. 16/772,043, filed as application No. PCT/EP2018/084689 on Dec. 13, 2018, now Pat. No. 11,292,831.

(30) Foreign Application Priority Data

Dec. 15, 2017 (GB) ...................... 1720970

(51) Int. Cl.
C07K 16/18 (2006.01)
A61P 25/16 (2006.01)
A61K 39/00 (2006.01)

(52) U.S. Cl.
CPC ............. C07K 16/18 (2013.01); A61P 25/16 (2018.01); A61K 2039/505 (2013.01); C07K 2317/24 (2013.01); C07K 2317/565 (2013.01); C07K 2317/92 (2013.01)

(58) Field of Classification Search
None
See application file for complete search history.

(56) References Cited

U.S. PATENT DOCUMENTS

| 6,890,535 | B1 | 5/2005 | Schenk |
| 7,306,945 | B2 | 12/2007 | Chilcote et al. |
| 7,358,331 | B2 | 4/2008 | Chilcote et al. |
| 7,727,957 | B2 | 6/2010 | Schenk et al. |
| 7,910,333 | B2 | 3/2011 | Chilcote et al. |
| 7,919,088 | B2 | 4/2011 | Schenk et al. |
| 7,977,316 | B2 | 7/2011 | Schenk |
| 8,092,801 | B2 | 1/2012 | Schenk et al. |
| 8,147,833 | B2 | 4/2012 | Schenk et al. |
| 8,506,959 | B2 | 8/2013 | Schenk et al. |
| 8,609,820 | B2 | 12/2013 | Saldanha et al. |
| 8,632,776 | B2 | 1/2014 | Nordström et al. |
| 8,673,593 | B2 | 3/2014 | Chilcote et al. |
| 8,741,293 | B2 | 6/2014 | Dodel et al. |
| 8,790,644 | B2 | 7/2014 | Saldanha et al. |
| 8,809,506 | B2 | 8/2014 | Lannfelt et al. |
| 8,940,276 | B2 | 1/2015 | Weihofen et al. |
| 8,968,734 | B2 | 3/2015 | Nordström et al. |
| 9,315,569 | B2 | 4/2016 | Lannfelt et al. |
| 9,493,553 | B2 | 11/2016 | Kaluza et al. |
| 9,605,056 | B2 | 3/2017 | Barbour et al. |
| 9,670,274 | B2 | 6/2017 | Kaluza et al. |
| 9,732,148 | B2 | 8/2017 | Ayalon et al. |
| 9,890,209 | B2 | 2/2018 | Kaluza et al. |
| 9,896,504 | B2 | 2/2018 | Weihofen et al. |
| 10,081,674 | B2 | 9/2018 | Barbour et al. |
| 11,261,242 | B2 | 3/2022 | Adams et al. |
| 2003/0166558 | A1 | 9/2003 | Frangione et al. |
| 2004/0136993 | A1 | 7/2004 | Schenk et al. |
| 2005/0037013 | A1 | 2/2005 | Schenk et al. |
| 2005/0196818 | A1 | 9/2005 | Chilcote et al. |
| 2008/0014194 | A1 | 1/2008 | Schenk et al. |
| 2011/0059093 | A1 | 3/2011 | Bohrmann et al. |
| 2013/0072663 | A1 | 3/2013 | Chilcote et al. |
| 2013/0108546 | A1 | 5/2013 | Saldanha et al. |
| 2014/0241984 | A1 | 8/2014 | El-Agnaf |
| 2014/0369940 | A1 | 12/2014 | Weihofen et al. |
| 2015/0139937 | A1 | 5/2015 | Gendelman et al. |
| 2015/0140003 | A1 | 5/2015 | Kaluza et al. |
| 2016/0060331 | A1 | 3/2016 | Schenk et al. |
| 2017/0320940 | A1 | 11/2017 | Ayalon et al. |
| 2017/0349651 | A1 | 12/2017 | Schenk et al. |
| 2018/0134775 | A1 | 5/2018 | El-Agnaf et al. |
| 2018/0134776 | A1 | 5/2018 | El-Agnaf et al. |
| 2018/0134777 | A1 | 5/2018 | El-Agnaf et al. |
| 2018/0237510 | A1 | 8/2018 | Kaluza et al. |

FOREIGN PATENT DOCUMENTS

| DE | 102011008153 A1 | 7/2012 |
| EP | 1185296 B1 | 1/2011 |
| EP | 2371396 B1 | 1/2014 |
| EP | 2272539 B1 | 3/2014 |
| EP | 2807188 B1 | 12/2014 |

(Continued)

OTHER PUBLICATIONS

Almandoz-Gil et al., "Low molar excess of 4-oxo-2-nonenal and 4-hydroxy-2-nonenal promote oligomerization of alpha-synuclein through different pathways," Free Radical Biology and Medicine 110:421-431 (2017).

(Continued)

Primary Examiner — Daniel E Kolker
Assistant Examiner — James Ryland Melchior
(74) Attorney, Agent, or Firm — MEDLER FERRO WOODHOUSE & MILLS PLLC

(57) ABSTRACT

The present invention relates to alpha synuclein binding antibodies and fragments thereof capable of binding alpha synuclein as a monomer and in fibrils and preventing alpha synuclein aggregation induced by alpha synuclein fibrils. The antibodies of the present invention are for use in the treatment of alpha synucleinopathies, including Parkinson's disease.

15 Claims, 16 Drawing Sheets
Specification includes a Sequence Listing.

(56) References Cited

FOREIGN PATENT DOCUMENTS

| EP | 2370466 | B1 | 5/2015 |
|---|---|---|---|
| EP | 1578253 | B1 | 8/2015 |
| EP | 2903648 | B1 | 8/2015 |
| EP | 2949666 | B1 | 12/2015 |
| EP | 2583978 | B1 | 4/2016 |
| EP | 3067066 | B1 | 9/2016 |
| EP | 2450056 | B1 | 3/2017 |
| EP | 2361928 | B1 | 4/2017 |
| EP | 1633189 | B1 | 7/2017 |
| EP | 2539366 | B1 | 11/2017 |
| EP | 2723379 | B1 | 9/2018 |
| EP | 3369433 | A1 | 9/2018 |
| EP | 2282758 | B1 | 11/2018 |
| WO | 2002/050121 | A1 | 6/2002 |
| WO | 2004/041067 | A3 | 5/2004 |
| WO | 2005/013889 | A3 | 2/2005 |
| WO | 2005/047860 | A3 | 5/2005 |
| WO | 2006/020581 | A3 | 2/2006 |
| WO | 2006/045037 | A3 | 4/2006 |
| WO | 2007/012061 | A3 | 1/2007 |
| WO | 2007011907 | A2 | 1/2007 |
| WO | 2007/021255 | A1 | 2/2007 |
| WO | 2008/103472 | A3 | 8/2008 |
| WO | 2009/133521 | A3 | 11/2009 |
| WO | 2010/069603 | A1 | 6/2010 |
| WO | 2011/104696 | A1 | 9/2011 |
| WO | 2011/107544 | A1 | 9/2011 |
| WO | 2012/061785 | A3 | 5/2012 |
| WO | 2012/061786 | A1 | 5/2012 |
| WO | 2012/177972 | A1 | 12/2012 |
| WO | 2013/063516 | A1 | 5/2013 |
| WO | 2013/112945 | A1 | 8/2013 |
| WO | 2013/180201 | A1 | 12/2013 |
| WO | 2014/058924 | A3 | 4/2014 |
| WO | 2014/132210 | A1 | 9/2014 |
| WO | 2015/001504 | A2 | 1/2015 |
| WO | 2015/051159 | A1 | 4/2015 |
| WO | 2015/075011 | A1 | 5/2015 |
| WO | 2015/075635 | A2 | 5/2015 |
| WO | 2015/155694 | A1 | 10/2015 |
| WO | 2015/179867 | A1 | 11/2015 |
| WO | 2015/197772 | A1 | 12/2015 |
| WO | 2016/040903 | A1 | 3/2016 |
| WO | 2016/040905 | A1 | 3/2016 |
| WO | 2016/040907 | A1 | 3/2016 |
| WO | 2016/061389 | A3 | 4/2016 |
| WO | 2017/009312 | A1 | 1/2017 |
| WO | 2017/033152 | A1 | 3/2017 |
| WO | 2017/091512 | A1 | 6/2017 |
| WO | 2017/176835 | A2 | 10/2017 |
| WO | 2017/207739 | A1 | 12/2017 |
| WO | 2018/007817 | A1 | 1/2018 |
| WO | 2018/039147 | A1 | 3/2018 |
| WO | 2018/091444 | A1 | 5/2018 |
| WO | 2018/109058 | A1 | 6/2018 |
| WO | 2018/111670 | A3 | 6/2018 |
| WO | 2018/115225 | A1 | 6/2018 |
| WO | 2018/128454 | A1 | 7/2018 |
| WO | 2018/128722 | A1 | 7/2018 |
| WO | 2018/151821 | A1 | 8/2018 |
| WO | 2018/178950 | A1 | 10/2018 |
| WO | 2018/213440 | A1 | 11/2018 |
| WO | 2018/237338 | A1 | 12/2018 |
| WO | 2019/115674 | A1 | 6/2019 |

OTHER PUBLICATIONS

Anderson et al., "Phosphorylation of Ser-129 is the dominant pathological modification of alpha-synuclein in familial and sporadic Lewy body disease," J Biol Chem 281:29739-29752 (2006).
Assayag et al., "Polyunsaturated fatty acids induce a-synuclein-related pathogenic changes in neuronal cells," Am J Pathology 171(6):2000-2011 (2007).
Baba et al., "Aggregation of alpha-synuclein in Lewy bodies of sporadic Parkinson's disease and dementia with Lewy bodies," Am J Pathology 152(4):879-884 (1998).
Bae et al., "Lipid peroxidation product 4-hydroxy-2-nonenal promotes seeding-capable oligomer formation and cell-to-cell transfer of α-synuclein," Antioxid. Redox Signal 18(7):770-783 (2013).
Bengoa-Vergniory et al., "Alpha-synuclein oligomers: a new hope," J. Acta Neuropathol 134:819-838 (2017).
Bergström et al., "Development of Passive Immunotherapies for Synucleinopathies," Movement Disorders 31(2):203-213 (2016).
Bloch et al., "α-Synuclein pathology of the spinal and peripheral autonomic nervous system in neurologically unimpaired elderly subjects," Neuropathology and Applied Neurobiology 32:284-295 (2006).
Bosco et al., "Elevated levels of oxidized cholesterol metabolites in Lewy body disease brains accelerate α-synuclein fibrilization," Nature Chemical Biology 2(5):249-253 (2006).
Chen et al., "Enhancement and destruction of antibody function by somatic mutation: unequal occurrence is controlled byV gene combinatorial associations" EMBO 14(12):2784-2794 (1995).
Cole et al., "Lipid droplet binding and oligomerization properties of the Parkinson's disease protein α-synuclein," JBC 277(8):6344-6352 (2002).
Cole et al., "Metal-catalyzed Oxidation of α-Synuclein Helping to Define the Relationship Between Oligomers, Protofibrils, and Filaments," J Biol Chem 280(10):9678-9690 (2005).
Conway et al., "Accelerated in vitro fibril formation by a mutant α-synuclein linked to early-onset Parkinson disease," Nature Medicine 4(11):1318-1320 (1998).
Cremades et al., "Chapter Three—Structural Characteristics of α-Synuclein Oligomers," International Review of Cell and Molecular Biology 329:79-143 (2017).
Cremades et al., "Direct observation of the interconversion of normal and toxic forms of α-synuclein," Cell 149:1048-1059 (2012).
Croisier et al., "Comparative study of commercially available anti α-synuclein antibodies," Neuropathology and Applied Neurobiology 32:351-356 (2006).
Curtiss et al., "Selection of monoclonal antibodies for linear epitopes of an apolipoprotein yields antibodies with comparable affinity for lipid-free and lipid-associated apolipoprotein," Journal of Lipid Research 37:884-892 (1996).
Danzer et al., "Different species of α-synuclein oligomers induce calcium influx and seeding," J Neuroscience 27(34):9220-9232 (2007).
Dehay et al., "Targeting α-synuclein for treating Parkinson's disease: mechanistic and therapeutic considerations," Lancet Neurol. 14(8): 855-866 (2015).
Deng et al., "Projecting human pharmacokinetics of therapeutic antibodies from nonclinical data. What have we learned?" mAbs 3:1, 61-66; (2011).
Dimitrov et al., "Therapeutic Antibodies: Current State and Future Trends—is a Paradigm Change Coming Soon?" Meth Mol Biol 525: Chapter 1, pp. 1-27 (2009).
Duda et al., "Immunohistochemical and Biochemical Studies Demonstrate a Distinct Profile of a-Synuclein Permutations in Multiple System Atrophy," Journal of Neuropathology and Experimental Neurology 59:9 830-841 (2000).
El-Agnaf et al., "α-Synuclein implicated in Parkinson's disease is present in extracellular biological fluids, including human plasma," FASEB J 17:1945-1947 (2003).
Emadi et al., "Inhibiting aggregation of α-synuclein with human single chain antibody fragments," Biochem 43(10):2871-2878 (2004).
Emadi et al., "Isolation of a human single chain antibody fragment against oligomeric α-synuclein that inhibits aggregation and prevents α-synuclein-induced toxicity," J. Mol. Biol. 368(4):1132-1144 (2007).
Fagerqvist et al., "Monoclonal antibodies selective for α-synuclein oligomers/protofibrils recognize brain pathology in Lewy body disorders and α-synuclein transgenic mice with the disease-causing A30P mutation," Journal of Neurochemistry 126:131-144 (2013).
Fairfoul et al., "Alpha-synuclein RT-QuIC in the CSF of patients with alpha-synucleinopathies," Annals of Clinical and Translational Neurology 3(10): 812-818 (2016).

(56) References Cited

OTHER PUBLICATIONS

Fernagut et al., "Behavioral and histopathological consequences of paraquat intoxication in mice: Effects of α-synuclein over-expression," Synapse 61(12):991-1001 (2007).
Fjorback et al., "Determination of α-synuclein concentration in human plasma using ELISA," Scandanavian Journal of Clinical & Laboratory Investigation 67:431-435 (2007).
Fujiwara et al., "α-Synuclein is phosphorylated in synucleinopathy lesions," Nat Cell Biol 4: 160-164 (2002).
Games et al., "Reducing C-Terminal-Truncated Alpha-Synuclein by Immunotherapy Attenuates Neurodegeneration and Propagation in Parkinson's Disease-Like Models," J. Neurosci 34(28):9441-9454 (2014).
Garambois et al., "Fully human IgG and IgM antibodies directed against the carcinoembryonic antigen (CEA) Gold 4 epitope and designed for radioimmunotherapy (RIT) of colorectal cancers," BMC Cancer 4:75 (2004).
George et al., "Characterization of a novel protein regulated during the critical period for song learning in the zebra finch," Neuron 15:361-372 (1995).
Giasson et al., "A panel of epitope-specific antibodies detects protein domains distributed throughout human a-synuclein in lewy bodies of Parkinson's disease," J Neurosci Res 59:528-533 (2000).
Goedert, "α-synuclein and neurodegenerative diseases," Nature Reviews Neuroscience 2:491-501 (2001).
Gomez-Tortosa et al., "α-Synuclein immunoreactivity in dementia with Lewy bodies: morphological staging and comparison with ubiquitin immunostaining," Acta Neuropathologica 99(4):352-357 (2000).
Guilliams et al., "Nanobodies raised against monomeric alpha-synuclein distinguish between fibrils at different maturation stages," Journal of Molecular Biology 425:2397-2411 (2013).
Jakes et al., "Epitope mapping of LB509, a monoclonal antibody directed against human a-synuclein," Neuroscience Letters 269:13-16 (1999).
Jakobovits, "A Production of fully human antibodies by transgenic mice," Current Opinion in Biotechnology 6:561-566 (1995).
Jankovic et al., "Safety and Tolerability of Multiple Ascending Doses of PRX002/RG7935, an Anti-α-Synuclein Monoclonal Antibody, in Patients with Parkinson Disease. A Randomized Clinical Trial," JAMA Neurol. 75(10):1206-1214 (2018).
Jensen et al., "α-Synuclein binds to tau and stimulates the protein kinase A—catalyzed tau phosphorylation of serine residues 262 and 356," J. Biol. Chem 274(36):25481-25489 (1999).
Jensen et al., "Microtubule-associated protein 1B is a component of cortical Lewy bodies and binds α-synuclein filaments," JBC 275(28):21500-21507 (2000).
Kahle et al., "Physiology and pathophysiology of alpha-synuclein. Cell culture and transgenic animal models based on a Parkinson's disease-associated protein," Ann N Y Acad Sci 920:33-41 (2000).
Kahle et al., "Subcellular Localization of Wild-Type and Parkinson's Disease-Associated Mutant a-Synuclein in Human and Transgenic Mouse Brain," J. Neuroscience 20(17):6365-6373 (2000).
Kawamata et al., "Interaction of α-synuclein and synphilin-1: effect of Parkinson's disease-associated mutations," J. Neurochem. 77:929-934 (2001).
Kayed et al., "Common structure of soluble amyloid oligomers implies common mechanism of pathogenesis," Science 300:486-489 (2003).
Kim et al., "Transneuronal Propagation of Pathologic α-Synuclein from the Gut to the Brain Models Parkinson's Disease," Neuron. 103(4):627-641 (2019).
Klos et al., "α-Synuclein pathology in the spinal cords of neurologically asymptomatic aged individuals," Neurology 66:1100-1102 (2006).
Kramer et al., "Presynaptic alpha-Synuclein Aggregates, Not Lewy Bodies, Cause Neurodegeneration in Dementia with Lewy Bodies," J. Neuroscience 27(6):1405-1410 (2007).
Kunik et al., "Structural Consensus among Antibodies defines the antigen binding site," PLoS Comput Biol 8(2) (2012).
Kussie et al., "A Single Engineered Amino Acid Substitution Changes Antibody Fine Specificity," J Immunol 152(1):146-52 (1994).
Lee et al., "Characterization of Cytoplasmic alpha-Synuclein Aggregates," J Biol Chem 277(50):48976-48983 (2002).
Lee et al., "Intravesicular localization and exocytosis of α-synuclein and its aggregates," J. Neuroscience 25(25):6016-6024 (2005).
Lee et al., "Real-time analysis of amyloid fibril formation of α-synuclein using a fibrillation-state-specific fluorescent probe of JC-1," Biochem J 418:311-323 (2009).
Lipman et al., "Monoclonal versus polyclonal antibodies: distinguishing characteristics, applications, and information resources," ILAR Journal 46:258-268 (2005).
Lynch et al., "An ScFv Intrabody Against the Non-Amyloid Component of Alpha Synuclein Reduces Intracellular Aggregation and Toxicity," J Mol Biol 377(1):136-147 (2008).
Maguire-Zeiss et al., "Identification of human α-synuclein specific single chain antibodies," Biochem Biophys Res Comm 349:1198-1205 (2006).
Margutti et al., "Autoantibodies to the C-terminal subunit of RLIP76 induce oxidative stress and endothelial cell apoptosis in immune-mediated vascular diseases and atherosclerosis," Blood 111(9):4559-4570 (2007).
Mariuzza, R.A., "The Structural Basis of Antigen-Antibody Recognition," Ann. Rev. Biophys. Biophys. Chem. 16:139-159 (1987).
Masliah et al., "Effects of α-synuclein immunization in a mouse model of Parkinson's disease," Neuron 46:857-868 (2005).
Masliah et al., "Passive Immunization Reduces Behavioral and Neuropathological Deficits in an Alpha-Synuclein Transgenic Model of Lewy Body Disease," PLoS One 4:1-17 (2011).
Mayo "Parkinson's disease," accessed from mayoclinic.org on Nov. 7, 2018.
McLean et al., "Membrane Association and Protein Conformation of α-Synuclein in Intact Neurons Effect of Parkinson's Disease-Linked Mutations," J. Biol. Chem 275(12):8812-8816 (2000).
Miller et al., "α-Synuclein in blood and brain from familial Parkinson disease with SNCA locus triplication," Neurology 62:1835-1838 (2004).
Milne et al., "Heat-Labile Antigens of *Salmonella enteritidis* I. Extraction of Antigens," J Bacteriol. 92(3):543-548 (1966).
Näsström et al., "P4-284: Oligomeric amorphous species of alpha-synuclein induce toxicity in a cellular model," Alzh Dem: J Alzh Assoc 4(4):T754 (2008).
Näsström et al., "The lipid peroxidation metabolite 4-oxo-2-nonenal cross-links α-synuclein causing rapid formation of stable oligomers," Biochem. Biophys. Res. Comm. 378:872-876 (2009).
Näsström et al., "Antibodies against α-synuclein reduce oligomerization in living cells," PLoS One 6(10):e27230 (2011).
Okochi et al., "Constitutive phosphorylation of the Parkinson's disease associated alpha-synuclein," J Biol Chem 275: 390-397 (2000).
Olanow et al., "Parkinson's Disease and Alpha Synuclein: Is Parkinson's Disease a Prion-Like Disorder?" Movement Disorders 28(1):31-40 (2013).
Oueslati, "Implication of Alpha-Synuclein Phosphorylation at S129 in Synucleinopathies: What Have We Learned in the Last Decade?" Journal of Parkinson's Disease 6:39-51 (2016).
Perez De La Lastra et al., "Epitope mapping of 10 monoclonal antibodies against the pig analogue of human membrane cofactor protein (MCP)," Immunology 96(4):663-670 (1999).
Qin et al., "Effect of 4-hydroxy-2-nonenal modification on α-synuclein aggregation," J Biol Chem 282(8):5862-5870 (2007).
Reichmann et al., "Reshaping human antibodies for therapy," Nature 332:323-327 (1988).
Ruesink et al., "Stabilization of α-synuclein oligomers using formaldehyde," PLoS One 14(10): e0216764 (2019).
Schenk et al., "First in human assessment of PRX002, an anti-alpha-synuclein monoclonal antibody, in healthy volunteers," Movement Disorders 32(2):211-218 (2017).
Schneider et al., "Over-expression of alpha-synuclein in human neural progenitors leads to specific changes in fate and differentiation," Human Molecular Genetics 16(6):651-666 (2007).

(56) References Cited

OTHER PUBLICATIONS

Shen et al., "Identifying the Pathological Domain of Alpha-Synuclein as a Therapeutic for Parkinson's Disease," Int J Mol Sci. 20(9):2338 (2019).
Seo et al., "α-Synuclein regulates neuronal survival via Bcl-2 family expression and PI3/Akt kinase pathway," FASEB J 16(13):1826-1828 (2002).
Serpell et al., "Fiber diffraction of synthetic a-synuclein filaments shows amyloid-like cross-β conformation," PNAS 97(9):4897-4902 (2000).
Shamoto-Nagai et al., "In parkinsonian substantia nigra, α-synuclein is modified by acrolein, a lipid-peroxidation product, and accumulates in the dopamine neurons with inhibition of proteasome activity," J Neural Transm 114:1559-1567 (2007).
Sharma et al., "A close association of torsinA and α-synuclein in lewy bodies: a fluorescence resonance energy transfer study," American J. Pathology 159(1):339-344 (2001).
Sharon et al., "The Formation of Highly Soluble Oligomers of alpha-Synuclein is Regulated by Fatty Acids and Enhanced in Parkinson's Disease," Neuron 37:583-595 (2003).
Souza et al., "Dityrosine Cross-linking Promotes Formation of Stable a-Synuclein Polymers," JBC 275:24 18344-18349 (2000).
Stefanis, "A-Synuclein in Parkinson's Disease," Cold Spring Harb Perspect Med 4:a009399 (2012).
Sumikura et al., "Distribution of α-synuclein in the spinal cord and dorsal root ganglia in an autopsy cohort of elderly persons," Acta neuropathologica communications 3(1):1-11 (2015).
Tickle et al., "A fully automated primary screening system for the discovery of therapeutic antibodies directly from B cells," J Biomol Screen 20(4):492-497 (2015).
Toyokuni et al., "The monoclonal antibody specific for the 4-hydroxy-2-nonenal histidine adduct," FEBS Letters 359:189-191 (1995).
Tran et al., "α-Synuclein Immunotherapy Blocks Uptake and Templated Propagation of Misfolded alpha-Synuclein and Neurodegeneration," Cell Reports 7(6):2054-2065 (2014).
Trostchansky et al., "Interaction with phospholipids modulates α-synuclein nitration and lipid-protein adduct formation," Biochem. J. 393: 343-349 (2006).
Vaikath et al., "Generation and Characterization of novel conformation-specific monoclonal antibodies for alpha-synuclein pathology," Neurobiology of Disease 79: 81-99 (2015).
Van Der Putten et al., "Neuropathology in mice expressing human α-synuclein," J. Neuroscience 20(16):6021-6029 (2000).
Van Diggelen et al., "Two conformationally distinct α-synuclein oligomers share common epitopes and the ability to impair long-term potentiation," PLoS One 14(3):e0213663 (2019).
Msanji et al., "α-Synuclein-Based Animal Models of Parkinson's Disease: Challenges and Opportunities in a New Era," Trends in Neurosciences, 39(11) 750-762 (2016).
Vogiatzi et al., "Wild type α-synuclein is degraded by chaperone-mediated autophagy and macroautophagy in neuronal cells," JBC 283(35):23542-23556 (2008).
Volpicelli-Daley et al., "Exogenous a-Synuclein Fibrils Induce Lewy Body Pathology Leading to Synaptic Dysfunction and Neuron Death," Neuron 72, 57-71 (2011).
Wahlberg et al., "Development of oligomer-specific alpha-synuclein antibodies," Alzheimer's & Dementia 4(4) Suppl. T481-T482, P2-372 (2008).
Weber et al., "From rabbit antibody repertoires to rabbit monoclonal antibodies," Experimental and Molecular Medicine 49: e305 (2017).
Yamashita et al., "Recent advances in the generation of human monoclonal Antibody," Cytotechnology 55:55-60 (2007).
Zhou et al., "Intrabody and Parkinson's disease," Biochim Biophys Acta 1792:634-642 (2009).
The International Search Report issued in PCT/EP2018/084689 dated Mar. 25, 2019.
Information on H3C Ab from U Iowa—D2 in Opposition of EP 2282758 submitted Aug. 16, 2019.
Datasheet for the 211 antibody—D14 in Opposition of EP 2282758 submitted Aug. 16, 2019.
Cosmo Bio News Topics Digest 2004—D17 in Opposition of EP 2282758 submitted Aug. 16, 2019.
Webpage for 610787 antibody—D20 in Opposition of EP 2282758 submitted Aug. 16, 2019.
Datasheet for 610787 antibody—D21 in Opposition of EP 2282758 submitted Aug. 16, 2019.
Screenshot for MAB3249 antibody—D29 in Opposition of EP 2282758 submitted Aug. 16, 2019.
MAb3249 Datasheet—D30 in Opposition of EP 2282758 submitted Aug. 16, 2019.
Screenshot for ab48506 antibody—D33 in Opposition of EP 2282758 submitted Aug. 16, 2019.
Screenshot of HNEJ-2 antibody—D34 in Opposition of EP 2282758 submitted Aug. 16, 2019.
Asano thesis 2007 Marshall University—D36 in Opposition of EP 2282758 submitted Aug. 16, 2019.
Experimental report for 8A5 antibody—D40 in Opposition of EP 2282758 submitted Aug. 16, 2019.
Product sheet for 8A5 producing cell line—D41 in Opposition of EP 2282758 submitted Aug. 16, 2019.
Patentee's letter of Jul. 9, 2014 re EP2539366—D45 in Opposition of EP 2282758 submitted Aug. 16, 2019.
Technical Report—Binding data of anti-alpha synuclein antibodies—D1 in Opposition of EP 2282758 submitted Aug. 21, 2019.
Tocris—Datasheet for DHA—D6 in Opposition of EP 2282758 submitted Aug. 21, 2019.
Exhibit 1 submitted by patentee Feb. 27, 2018—D12 in Opposition of EP 2282758 submitted Aug. 21, 2019.
EP Appl. No. 08022188—priority to WO2010069603—E6 in Opposition of EP 2282758 submitted Aug. 21, 2019.
Letter dated Mar. 14, 2017—D1 in Opposition of EP3067066 submitted Dec. 24, 2019.
Letter dated Jan. 8, 2018 filed during examination—D2 in Opposition of EP 3067066 submitted Dec. 24, 2019.
Letter dated Jul. 30, 2018 filed during examination—D3 in Opposition of EP 3067066 submitted Dec. 24, 2019.
Letter dated Aug. 24, 2018 filed during examination—D4 in Opposition of EP 3067066 submitted Dec. 24, 2019.
Response filed May 31, 2011 in U.S. Appl. No. 12/037,081—D5 in Opposition of EP 3067066 submitted Dec. 24, 2019.
ATCC deposit receipt for antibody 9E4 dated Feb. 26, 2007—D6 in Opposition of EP 3067066 submitted Dec. 24, 2019.
Declaration of E Masliah filed in U.S. Pat. No. 11,710,248—D27 in Opposition of EP 3067066 submitted Jun. 8, 2020.
Declaration of Leda Alfonso Trujillo filed in Ecuador Application SENADI-2020-39610, mailed May 5, 2021.
Declaration of Leda Alfonso Trujillo filed in Ecuador Application SENADI-2020-39623, mailed May 5, 2021.
Non-final Office Action in U.S. Appl. No. 16/771,993 dated May 5, 2021.
Notice of Allowance in U.S. Appl. No. 16/771,993 dated Nov. 5, 2021.

ELISA Binding of 6470 RbIgG1 to recombinant human alpha synuclein monomer and fibrils and PVDPDNEAYE peptide ELISA Binding of 5811 mIgG1 to recombinant human alpha synuclein monomer and fibrils FIG. 6
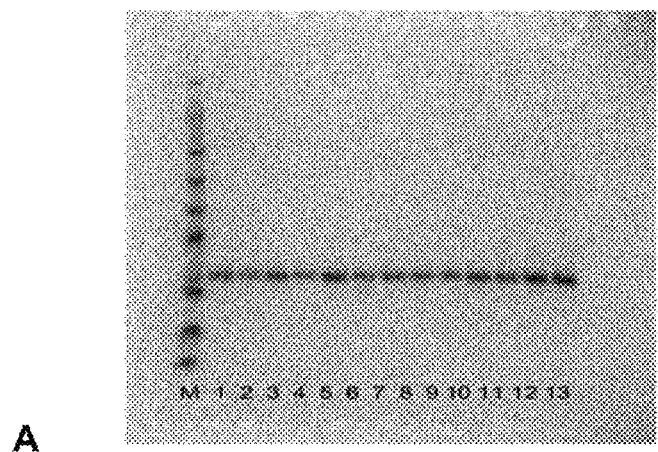
A
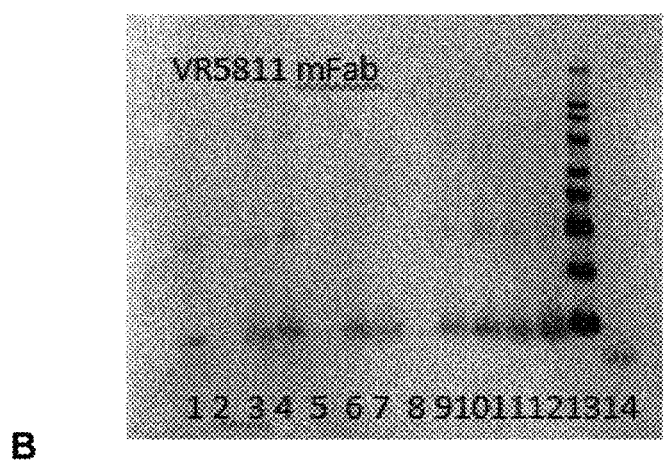
B
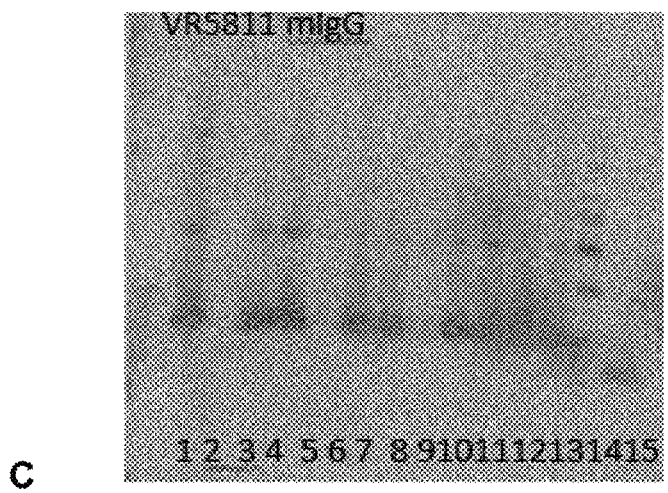
C

FIG. 7

```
                1       5        10        15        20        25        30        35        40        45        50        55        60        65        70        75        80        85        90        95        100       105
Light 5811      NIQMTQSPPVLSASVGDRVTLSCRASQNINKNLDWYQQRPGERPKLLMYIANNLQTGIPSRFSGSGSGTDYTLTISSLQPEDVATYYCLQYKNG-WTFGQGTKLELK
IGKV1-39        DIQMTQSPSSLSASVGDRVTITCRASQSISSYLNWYQQKPGKAPKLLIYAASSLQSGVPSRFSGSGSGTDFTLTISSLQPEDFATYYCQQSYSTPWTFGQGTKVEIK
5811g15         DIQMTQSPSSLSASVGDRVTITCRASQNINKNLDWYQQKPGKAPKLLIYANNLQTGVPSRFSGSGSGTDFTLTISSLQPEDFATYYCLQYKNG-WTFGQGTKVEIK
5811g16         DIQMTQSPSSLSASVGDRVTITCRASQNINKNLDWKQQPGKAPKLLIYANNLQTGVPSRFSGSGSGTDFLLTISSLQPEDFADYYCLQYKNG-WTFGQGTKVEIK
5811g14         DIQMTQSPSSLSASVGDRVTILCKASQNINKNLDWYQQKPGKAPKLLIYANNLQTGVPSRFSGSGSGTDFTLTISSLQPEDFATYYCLQYKNA-WTFGQGTKVEIK
```

ANTI-ALPHA-SYNUCLEIN ANTIBODIES

REFERENCE TO AN ELECTRONIC SEQUENCE LISTING

The instant application contains a Sequence Listing which has been submitted electronically in ASCII format and is hereby incorporated by reference in its entirety. Said ASCII copy, created on Oct. 5, 2021, is named 0089-0028US1_SL.txt and is 45,967 bytes in size.

FIELD OF THE INVENTION

The present invention relates to anti-alpha synuclein antibodies and method of using the same to treat synucleinopathies. In particular, the present invention relates to anti-human alpha synuclein antibodies and their use in the treatment of Parkinson's Disease.

BACKGROUND OF THE INVENTION

Alpha synuclein is a small soluble 140 amino acid long protein existing in radically different forms. Alpha synuclein is mainly found in pre-synaptic nerve terminals and although its precise function is unknown researchers believe it plays a central role in multiple neurodegenerative processes.

Over the past 15 years, alpha synuclein has been shown to play a key role in the pathogenesis of all forms of Parkinson's disease. Genetic mutations or gene multiplications of the alpha synuclein gene cause familial early onset Parkinson's disease (PD). Interestingly in gene locus multiplication families, the pathogenic effect is clearly dependent on the gene dosage. Gene duplications cause a relatively early onset form of PD (~47 years old) which has a normal disease course, while gene triplications are associated with a very early age of onset (~33 years old) and a very rapid disease course. In all forms of Parkinson's disease alpha synuclein is the main constituent of Lewy bodies, the key pathological hallmark of the disease.

Lewy bodies pathology expands during the course of the disease and it is proposed that alpha synuclein acts as a prion like protein, which misfolds to form toxic oligomers and aggregates that can spread from affected to unaffected neurons (Olanow C. W et al. Movement Disorders, Vol 28, No. 1, 2013). Current existing therapies are not capable of stopping the disease spreading and only aid the treatment of the symptoms associated with the progressive loss of motor-neurons dependent activities. In 2014, Tran H. T. et al (Tran H. T. et al, Cell Reports 7, 2054-2065, Jun. 26, 2014) showed that intraperitoneal administration of a monoclonal antibody for misfolded alpha synuclein to mice previously injected intrastriatally with alpha synuclein preformed fibrils reduced the Lewy bodies pathology, ameliorated substantia nigra dopaminergic neuron loss and improved motor impairments. Hence, there still remains the need of a passive immune-therapy that could exert therapeutic effects in PD and other synucleinopathies.

SUMMARY OF THE INVENTION

The present invention addresses the above-identified need by providing anti-alpha synuclein antibodies according to the following embodiments.

Embodiment 1: An antibody or antigen-binding fragment thereof which binds to alpha synuclein wherein the antibody or fragment thereof comprises:

a. a light chain variable region comprising a CDR-L1 selected from SEQ ID NO: 1; a CDR-L2 according to SEQ ID NO: 2 and a CDR-L3 according to SEQ ID NO: 3; and
b. a heavy chain variable region comprising a CDR-H1 according to SEQ ID NO: 4; a CDR-H2 selected from SEQ ID NO: 5 and a CDR-H3 selected from SEQ ID NO: 6.

Embodiment 2: The antibody or antigen-binding fragment thereof according to Embodiment 1, wherein amino acid residue glycine (Gly; G) at position 6 with reference to SEQ ID NO: 3 is replaced by alanine (Ala; A).

Embodiment 3: The antibody or antigen-binding fragment thereof according to Embodiments 1 or 2, wherein the antibody or antigen-binding fragment thereof binds two or more amino acid residues of alpha synuclein between position 113 and 129 with reference to SEQ ID NO: 8 wherein the antibody or antigen-binding fragment thereof binds at least amino acid residues D119, N122 and Y125.

Embodiment 4: The antibody or antigen-binding fragment thereof according to any one of the preceding claims, wherein the antibody or antigen-binding fragment prevents aggregation of alpha synuclein induced by alpha synuclein fibrils Embodiment 5: The antibody or antigen-binding fragment thereof according to any one of the preceding Embodiments, wherein the antibody or antigen-binding fragment thereof is capable of binding alpha synuclein as a monomer and in fibrils.

Embodiment 6: The antibody or antigen-binding fragment thereof according to any one of the preceding Embodiments which has a higher binding affinity for alpha synuclein in fibrils compared to alpha synuclein as monomer characterized by a constant of dissociation ($K_D$) at least 10 fold higher for monomeric alpha synuclein than for alpha synuclein in fibrils.

Embodiment 7: The antibody or antigen-binding fragment thereof according to any one of the preceding Embodiments which has a ($K_D$) for alpha synuclein in fibrils of 60 pM or less.

Embodiment 8: The antibody or antigen-binding fragment thereof according to any one of the preceding Embodiments wherein the antibody is a chimeric, humanized or human antibody.

Embodiment 9: The antibody or antigen-binding fragment thereof according to any one of the preceding Embodiments, wherein the antibody is a full-length antibody.

Embodiment 10: The antibody or antigen-binding fragment thereof according to Embodiment 9, wherein the full-length antibody is selected from an IgG1, IgG4 or IgG4P.

Embodiment 11: The antibody or antigen-binding fragment thereof according to any one of the preceding Embodiments, wherein the antigen-binding fragment is selected from a Fab, a Fab', a F(ab')$_2$, a scFv, a dAb or a $V_{HH}$.

Embodiment 12: The antibody or antigen-binding fragment thereof according to any one of the preceding Embodiments, wherein the antibody or fragment thereof comprises:

a. a light chain variable region according to SEQ ID NO: 13 and a heavy chain variable region selected from SEQ ID NO: 25; or
b. a light chain variable region according to SEQ ID NO: 17 and a heavy chain variable region selected from SEQ ID NO: 25; or
c. a light chain variable region according to SEQ ID NO: 21 and a heavy chain variable region selected from SEQ ID NO: 25.

Embodiment 13: The antibody or antigen-binding fragment thereof according to any one of Embodiments 1 to 11, wherein the antibody or fragment thereof comprises:
  a. a light chain according to SEQ ID NO: 14 and a heavy chain according to SEQ ID NO: 26; or
  b. a light chain according to SEQ ID NO: 18 and a heavy chain according to SEQ ID NO: 26; or
  c. a light chain according to SEQ ID NO: 22 and a heavy chain according to SEQ ID NO: 26.

Embodiment 14: An isolated polynucleotide encoding the antibody or antigen-binding fragment thereof according to any one of Embodiments 1 to 13.

Embodiment 15: The isolated polynucleotide according to Embodiment 14, wherein the polynucleotide encodes:
  a. a light chain variable region, wherein the polynucleotide:
    i. is at least 90% identical to SEQ ID NO: 15, 19 or 23; or
    ii. comprises SEQ ID NO: 15, or 19 or 23; or
    iii. consists essentially of SEQ ID NO: 15, 19 or 23; or
  b. a heavy chain variable region, wherein the polynucleotide:
    iv. is at least 90% identical to SEQ ID NO: 27; or
    v. comprises SEQ ID NO: 27; or
    vi. consists essentially of SEQ ID NO: 27; or
  c. a light chain, wherein the polynucleotide:
    vii. is at least 90% identical to SEQ ID NO: 16, 20 or 24; or
    viii. comprises SEQ ID NO: 16, 20 or 24; or
    ix. consists essentially of SEQ ID NO: 16, 20 or 24;
  d. a heavy chain, wherein the polynucleotide:
    x. is at least 90% identical to SEQ ID NO: 28; or
    xi. comprises SEQ ID NO: 28; or
    xii. consists essentially of SEQ ID NO: 28.

Embodiment 16: A cloning or expression vector comprising one or more polynucleotides according to any one of Embodiments 14 or 15.

Embodiment 17: A host cell comprising:
  a. one or more polynucleotides according to any one of Embodiments 14 or 15 or
  b. one or more expression vectors according to Embodiment 16.

Embodiment 18: A process for the production of an antibody or antigen-binding fragment thereof according to any one of Embodiments 1 to 13, comprising culturing the host cell according to claim 17 under suitable conditions for producing the antibody or antigen-binding fragment thereof and isolating the antibody or antigen-binding fragment thereof.

Embodiment 19: A pharmaceutical composition comprising the antibody or antigen-binding fragment thereof according to any one of Embodiments 1 to 13 and one or more pharmaceutically acceptable carriers, excipients or diluents, wherein the pharmaceutical composition comprises one or more additional active ingredients.

Embodiment 20: The antibody or antigen-binding fragment thereof according to any one of Embodiments 1 to 13 or the pharmaceutical composition according to Embodiment 19 for use in therapy.

Embodiment 21: The antibody or antigen-binding fragment thereof according to any one of Embodiments 1 to 13 or the pharmaceutical composition according to Embodiment 19 for use in the treatment of one or more synucleinopathies.

Embodiment 22: The antibody or antigen-binding fragment thereof of use according to Embodiment 21 wherein the synucleinopathy is selected from Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

Embodiment 23: The antibody or antigen-binding fragment thereof of use according to Embodiment 22 wherein the synucleinopathy is Parkinson's disease.

Embodiment 24: A method of treating a synucleinopathy in a patient comprising administering to said patient a therapeutically effective amount of an antibody or antigen-binding fragment thereof according to any one of Embodiments 1 to 13 or the pharmaceutical composition according to Embodiment 19.

Embodiment 25: The method according to Embodiment 24 wherein the synucleinopathy is selected from Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease.

Embodiment 26: The antibody or antigen-binding fragment thereof according to any one of Embodiments 1 to 13 or the pharmaceutical composition according to Embodiment 19 for use in the diagnosis of synucleinopathy, preferably in the diagnosis of Parkinson's disease.

BRIEF DESCRIPTION OF THE DRAWINGS

FIG. 1.

FIG. 2.

FIG. 4.

FIG. 6. Western blot of alanine scanning for the characterization of the epitope. (A) 4-12% Bis/Tris NuPage analysis of wild-type and single amino acid mutants of human alpha-synuclein (His-tagged). Lanes: M, SeeBluePlus2; 1, h a-syn V118A; 2, h a-syn D119A; 3, h a-syn P120A; 4, h a-syn D121A; 5, h a-syn N122A; 6, h a-syn E123A; 7, h a-syn A124S; 8, h a-syn Y125A; 9, h a-syn E126A; 10, h a-syn M127A; 11, h a-syn P128A; 12 and 13 h a-syn wild type. PVDF blot using (B) 5811 mFab and (C) 5811 mIgG as primary antibodies. Lanes: M, SeeBluePlus2; 1, h a-syn V118A; 2, h a-syn D119A; 3, h a-syn P120A; 4, h a-syn D121A; 5, h a-syn N122A; 6, h a-syn E123A; 7, h a-syn A124S; 8, h a-syn Y125A; 9, h a-syn E126A; 10, h a-syn M127A; 11, h a-syn P128A; 12 h a-syn wt (His-tagged); 13, MagicMark XP; 14, h a-syn wild type (no tag).

FIG. 7. Light Chain Humanization. 5811 is for the rat variable light chain sequence. 5811gL5, 5811gL8 and 5811gL14 are for the humanized grafts of antibody 5811 variable light chain using IGKV1-39 human germline as the acceptor framework. CDRs are shown in bold/underlined. Donor residue is shown in bold/italic and is shaded: Y71. The mutation in CDR-L3 to modify a potential deamidation site is shown in bold/underlined and is shaded: G94A. Figure discloses SEQ ID NOS 9, 29, 13, 17, and 21, respectively, in order of appearance.

DETAILED DESCRIPTION OF THE INVENTION

Figure 1A:
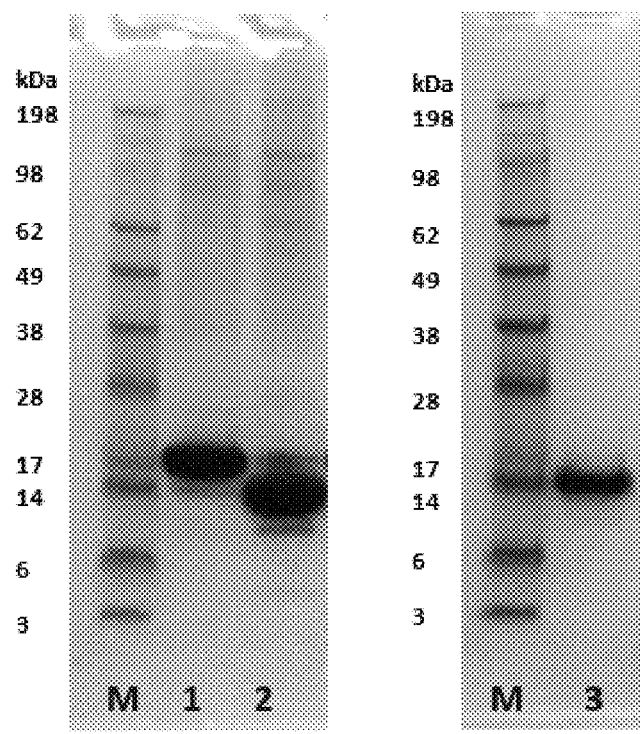
FIG. 1A SDS-PAGE of samples of alpha synuclein expression. Alpha synuclein with His tag (1) and after removal of His tag by TEV protease (2), Superdex 75 size exclusion chromatography on the TEV protease treated human alpha-synuclein (3). Protein molecular weight marker SeeBluePlus2 (Invitrogen) (M).

The present disclosure will now be described with respect to particular non-limiting aspects and embodiments thereof and with reference to certain figures and examples.

Technical terms are used by their common sense unless indicated otherwise. If a specific meaning is conveyed to certain terms, definitions of terms will be given in the context of which the terms are used.

Where the term "comprising" is used in the present description and claims, it does not exclude other elements. For the purposes of the present disclosure, the term "consisting of" is considered to be a preferred embodiment of the term "comprising of".

Where an indefinite or definite article is used when referring to a singular noun, e.g. "a", "an" or "the", this includes a plural of that noun unless something else is specifically stated.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of an anti-alpha synuclein antibody or antigen-binding fragment thereof that, when administered to a mammal or other subject for treating a disease, is sufficient to produce such treatment for the disease. The therapeutically effective amount will vary depending on the anti-alpha synuclein antibody or antigen-binding fragment thereof, the disease and its severity and the age, weight, etc., of the subject to be treated.

The term "isolated" means, throughout this specification, that the antibody, antigen-binding fragment or polynucleotide, as the case may be, exists in a physical milieu distinct from that in which it may occur in nature.

The present invention provides for an antibody or antigen-binding fragment thereof which binds to alpha synuclein wherein the antibody or fragment thereof comprises:
  a. a light chain variable region comprising a CDR-L1 selected from SEQ ID NO: 1; a CDR-L2 according to SEQ ID NO: 2 and a CDR-L3 according to SEQ ID NO: 3; and
  b. a heavy chain variable region comprising a CDR-H1 according to SEQ ID NO: 4; a CDR-H2 selected from SEQ ID NO: 5 and a CDR-H3 selected from SEQ ID NO: 6.

In one embodiment the amino acid residue glycine (Gly; G) at position 6 with reference to SEQ ID NO: 3 is replaced by alanine (Ala; A).

Alpha synuclein (or alpha syn; a-synuclein; a-syn or any other known synonym) refers to the general name of this protein and includes, without being limited to, alternative splicing variants, mutants and alpha synuclein from other species (mouse, monkey, etc.). Unless otherwise specified, when human alpha synuclein is intended or explicitly mentioned, such alpha synuclein comprises the sequence given in SEQ ID NO: 8 or in Uniprot P37840.

(SEQ ID NO: 8)
MDVFMKGLSKAKEGVVAAAEKTKQGVAEAAGKTKEGVLYVGSKTKEGVV
HGVATVAEKTKEQVTNVGGAVVTGVTAVAQKTVEGAGSIAAATGFVKKD
QLGKNEEGAPQEGILEDMPVDPDNEAYEMPSEEGYQDYEPEA.

The term 'antibody' as used herein generally relates to intact (whole) antibodies i.e. comprising the elements of two heavy chains and two light chains. The antibody may comprise further additional binding domains for example as per the molecule DVD-Ig as disclosed in WO 2007/024715, or the so-called (FabFv)$_2$Fc described in WO2011/030107. Thus, antibody as employed herein includes bi, tri or tetra-valent full-length antibodies.

Antigen-binding fragments of antibodies include single chain antibodies (i.e. a full length heavy chain and light chain); Fab, modified Fab, Fab', modified Fab', F(ab')$_2$, Fv, Fab-Fv, Fab-dsFv, single domain antibodies (e.g. $V_H$ or $V_L$ or $V_{HH}$), scFv, bi, tri or tetra-valent antibodies, Bis-scFv, diabodies, tribodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). The Fab-Fv format was first disclosed in WO2009/040562 and the disulphide stabilized versions thereof, the Fab-dsFv, was first disclosed in WO2010/035012. Other antibody fragments for use in the present invention include the Fab and Fab' fragments described in International patent applications WO2005/003169, WO2005/003170 and WO2005/003171. Multi-valent antibodies may comprise multiple specificities e.g. bispecific or may be monospecific (see for example WO 92/22583 and WO05/113605). One such example of the latter is a Tri-Fab (or TFM) as described in WO92/22583.

An alternative antigen-binding fragment comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in International Patent Application Publication No, WO2015/197772, which is hereby incorporated by reference in its entirety and particularly with respect to the discussion of antibody fragments.

A typical Fab' molecule comprises a heavy and a light chain pair in which the heavy chain comprises a variable region VH, a constant domain CH1 and a natural or modified hinge region and the light chain comprises a variable region VL and a constant domain CL. Dimers of a Fab' according to the present disclosure create a F(ab')$_2$ where, for example, dimerization may be through the hinge.

The antibody or antigen-binding fragment thereof according to the present invention binds to an epitope of alpha synuclein. Within the present invention, the term "epitope" is used interchangeably for both conformational and linear epitopes, where a conformational epitope is composed of discontinued sections of the antigen's amino acid primary sequence and a linear epitope is formed by a sequence formed by continuous amino acids.

The epitope can be identified by any suitable epitope mapping method known in the art in combination with any one of the antibodies provided by the present invention. Examples of such methods include screening peptides of varying lengths derived from full length alpha synuclein for binding to the antibody or fragment thereof of the present invention and identify the smallest fragment that can specifically bind to the antibody containing the sequence of the epitope recognized by the antibody. Alpha synuclein peptides may be produced synthetically or by proteolytic digestion of the alpha synuclein protein. Peptides that bind the antibody can be identified by, for example, mass spectrometric analysis. In another example, NMR spectroscopy or X-ray crystallography can be used to identify the epitope bound by an antibody of the present invention. Once identified, the epitope may serve for preparing fragments which bind an antibody of the present invention and, if required, used as an immunogen to obtain additional antibodies which bind the same epitope.

In one embodiment, the antibody or antigen-binding fragment thereof according to the present invention, binds two or more amino acid residues of alpha synuclein between position 113 and 129 with reference to SEQ ID NO: 8. In particular, the antibody or antigen-binding fragment thereof binds at least amino acid residues D119, N122 and Y125 with reference to SEQ ID NO: 8.

Preferably, the antibody or antigen-binding fragment thereof according to the present invention prevents alpha synuclein aggregation induced by alpha synuclein fibrils.

Within this specific context, the term "prevent" (and grammatical variations thereof) is used herein interchangeably with the term "inhibit" and indicates the effect antibodies according to the present invention have with respect to alpha synuclein aggregation induced by alpha synuclein fibrils. The effect may be prophylactic in terms of completely or partially preventing the aggregation; or completely or partially reducing, i.e. blocking aggregation that has already commenced from further progressing, or completely or partially reducing the occurrence of further aggregation; or completely or partially reversing aggregation which has already occurred.

Without wishing to be bound by theory it is believed that the antibody or antigen-binding fragment thereof according to the present invention binds to alpha synuclein:
  i) in monomeric form and prevents alpha synuclein to form oligomers and aggregates; and/or
  ii) in oligomeric and fibrillar form and prevents alpha synuclein to spread from neuron to neuron and/or
  iii) in oligomeric and/or fibrillar form and prevents alpha synuclein aggregation induced by alpha synuclein fibrils, preferably endogenous alpha synuclein aggregation.

The term "fibrils", "fibrillar form" or "in fibrils" as used herein with respect to alpha synuclein is meant to refer to non-monomeric forms of alpha synuclein, including alpha synuclein oligomers, which may constitute the spreading species within and between brain structures.

In one embodiment, the antibody or antigen-binding fragment thereof according to the present invention is capable of binding alpha synuclein as a monomer and in fibrils. In one embodiment, the antibody or antigen-binding fragment thereof has a stronger binding affinity for alpha synuclein in fibrils compared to alpha synuclein as monomer. This is characterized by a constant of dissociation ($K_D$) at least 10-fold higher for monomeric alpha synuclein than for alpha synuclein in fibrils.

In one embodiment, the antibody or antigen-binding fragment thereof according to the present invention has a constant of dissociation ($K_D$) of less than 60 pM for monomeric alpha synuclein. In another embodiment, the antibody or antigen-binding fragment thereof according to the present invention has a constant of dissociation ($K_D$) of less than 30 pM for alpha synuclein in fibrils.

The term "$K_D$" as used herein refers to the constant of dissociation which is obtained from the ratio of $K_d$ to $K_a$ (i.e. $K_d/K_a$) and is expressed as a molar concentration (M). $K_d$ and $K_a$ refers to the dissociation rate and association rate, respectively, of a particular antigen-antibody (or antigen-binding fragment thereof) interaction. $K_D$ values for antibodies can be determined using methods well established in the art. A method for determining the $K_D$ of an antibody is by using surface plasmon resonance, such as Biacore® system for example as described in the Examples herein, using isolated natural or recombinant alpha synuclein, a suitable fusion protein/polypeptide thereof or fibrils thereof. In one example affinity is measured using recombinant human alpha synuclein as described in the Examples herein. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In one embodiment, the antibody or antigen-binding fragment thereof according to the present invention has a higher binding affinity (i.e. smaller $K_D$) for alpha synuclein in fibrils compared to alpha synuclein as monomer. The term "affinity" refers to the strength of an interaction between the antibody or antigen-binding fragment thereof and alpha synuclein.

In one embodiment, the antibody or antigen-binding fragment thereof according to the present invention block or prevent or reduce aggregation induced by alpha synuclein, preferably, induced by alpha synuclein in fibrils.

In one embodiment, the antibody or antigen-binding fragment thereof according to the present invention has an $IC_{50}$ of less than 10 nM for blocking the aggregation induced by alpha synuclein in fibrils, preferably, the antibody or antigen-binding fragment thereof according to the present invention has an $IC_{50}$ of less than 5 nM for blocking the aggregation induced by alpha synuclein in fibrils.

The term $IC_{50}$ as used herein refers to the half maximal inhibitory concentration which is a measure of the effectiveness of a substance, such as an antibody, in inhibiting a specific biological or biochemical function, in the present invention aggregation induced by alpha synuclein, preferably alpha synuclein in fibrils. The $IC_{50}$ is a quantitative measure which indicates how much of a particular substance is needed to inhibit a given biological process by half.

In one embodiment, the antibody or antigen-binding fragment thereof according to the present invention do not bind beta synuclein and/or gamma synuclein and are specific for alpha synuclein.

Specific as employed herein is intended to refer to an antibody that only recognizes the antigen to which it is specific or an antibody that has significantly higher binding affinity to the antigen to which it is specific (e.g. alpha synuclein) compared to binding to antigens to which it is non-specific (gamma and beta synucleins), for example at least 5, 6, 7, 8, 9, 10 times higher binding affinity.

Antibodies according to the present invention may be obtained using any suitable method known in the art. The alpha synuclein polypeptide/protein including fusion proteins, cells (recombinantly or naturally) expressing the polypeptide can be used to produce antibodies which specifically recognize alpha synuclein. The polypeptide may be the 'mature' polypeptide or a biologically active fragment or derivative thereof.

In one embodiment, the polypeptide (i.e. antigen) is human alpha synuclein monomer or a fragment thereof, preferably produced as described in the Examples below.

Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The alpha synuclein polypeptide or a fragment thereof may in some instances be part of a larger protein such as a fusion protein for example fused to an affinity tag or similar.

Antibodies generated against the alpha synuclein polypeptide may be obtained, where immunization of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and WO2004/106377.

Screening for antibodies can be performed using assays to measure binding to alpha synuclein and/or assays to measure the inhibition of alpha synuclein to form fibrils in the presence of the antibody or fragment thereof.

The antibody or antigen-binding fragment thereof according to the present invention comprises complementarity determining regions (CDRs), three from a heavy chain and three from a light chain. Generally, the CDRs are in a framework and together form a variable region. By convention, the CDRs in the heavy chain variable region of an antibody or antigen-binding fragment thereof are referred as CDR-H1, CDR-H2 and CDR-H3 and in the light chain variable regions as CDR-L1-CDR-L2 and CDR-L3. They are numbered sequentially in the direction from the N-terminus to the C-terminus of each chain.

CDRs are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In one embodiment, the antibody may be a chimeric, humanized or human antibody or fragment thereof.

In one embodiment, the antibody or antigen-binding fragment thereof according to the present invention may comprise the framework regions of the animal in which the antibody was raised. For example, if the antibody was raised in a rat, it will comprise the CDRs as defined and claimed herein and the framework regions of the rat antibody such as an antibody or antigen-binding fragment thereof comprising a light chain variable region according to SEQ ID NO: 9 (which nucleotide sequence is shown in SEQ ID NO: 11) and a heavy chain variable region according to SEQ ID NO: 10 (which nucleotide sequence is shown in SEQ ID NO: 12).

Chimeric antibodies are typically produced using recombinant DNA methods. The DNA may be modified by substituting the coding sequence for human L and H chains for the corresponding non-human (e.g. murine) H and L constant regions (Morrison; PNAS 81, 6851 (1984)).

Human antibodies comprise heavy or light chain variable regions or full length heavy or light chains that are "the product of" or "derived from" a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertoires (Winter G; (1994) Annu Rev Immunol 12:433-455, Green L L, (1999) J Immunol Methods 231:1 1-23).

In one preferred embodiment of the invention, the antibody or antigen-binding fragment thereof according to the disclosure are humanized.

As used herein, the term 'humanized antibody molecule' refers to an antibody molecule wherein the heavy and/or light chain contains one or more CDRs (including, if desired, one or more modified CDRs) from a donor antibody (e.g. a non-human antibody such as a murine or rabbit monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs are grafted, any appropriate acceptor variable region framework sequence may be used having regard to the class/type of the donor antibody from which the CDRs are derived, including mouse, primate and human framework regions.

Suitably, the humanized antibody according to the present invention has a variable domain comprising human acceptor framework regions as well as one or more of the CDRs provided specifically herein. Thus, provided in one embodiment is a blocking humanized antibody which binds alpha synuclein, preferably human alpha synuclein, wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://www.imgt.org/.

In a humanized antibody or antigen-binding fragment thereof according to the present invention, the acceptor heavy and light chains do not necessarily need to be derived from the same antibody and may, if desired, comprise composite chains having framework regions derived from different chains.

A suitable framework region for the light chain of the humanized antibody of the present invention is derived from the human germline IGKV1-39 having SEQ ID NO:29 and which nucleotide sequence is shown in SEQ ID NO: 31.

Accordingly, in one embodiment there is provided a humanized antibody or antigen-binding fragment thereof comprising the sequence given in SEQ ID NO: 1 for CDR-L1, the sequence given in SEQ ID NO: 2 for CDR-L2 and the sequence given in SEQ ID NO: 3 or SEQ ID NO: 7 for CDRL3, wherein the light chain framework region is derived from the human germline IGKV1-39.

A suitable framework region for the heavy chain of the humanized antibody or antigen-binding fragment thereof according to the present invention is derived from the human germline IGHV3-15 having the sequence as shown in SEQ ID NO: 30 and which nucleotide sequence is shown in SEQ ID NO: 32.

In one embodiment there is provided a humanized antibody or antigen-binding fragment thereof comprising the sequence given in SEQ ID NO: 4 for CDR-H1, the sequence given in SEQ ID NO: 5 for CDR-H2 and the sequence given in SEQ ID NO: 6 for CDR-H3, wherein the heavy chain framework region is derived from the human germline IGHV3-15.

In another embodiment, there is provided a humanized antibody or antigen-binding fragment thereof comprising:
a light chain variable region comprising a CDR-L1 according to the sequence given in SEQ ID NO: 1, a CDR-L2 according to the sequence given in SEQ ID NO: 2 and a CDR-L3 according to the sequence given in SEQ ID NO: 3 or SEQ ID NO: 7, wherein the light chain framework region is derived from the human germline IGKV1-39 and
a heavy chain variable region comprising a CDR-H1 according to the sequence given in SEQ ID NO: 4, a CDR-H2 according to the sequence given in SEQ ID NO: 5 and a CDR-H3 according to the sequence given in SEQ ID NO: 6, wherein the heavy chain framework region is derived from the human germline IGHV3-15.

In a humanized antibody or antigen-binding fragment thereof according to the present invention, the framework regions may not have the same sequence as those of the acceptor antibody. For instance, unusual residues may be changed to more frequently-occurring residues for that acceptor chain class or type. Alternatively, selected residues in the acceptor framework regions may be changed so that they correspond to the residues found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967.

Thus, in one embodiment 1, 2, 3, 4, 5, 6, 7 or 8 residues in the framework are replaced with an alternative amino acid residue.

Accordingly, in one embodiment, there is provided a humanized antibody or antigen-binding fragment thereof, wherein the residue at position 71 (Phe (F) 71) of the variable domain of the light chain (with reference to SEQ ID NO: 17 or 18) is a donor residue (Tyr (Y) 71), see for example the sequence given in SEQ ID NO: 13 and 14.

In another embodiment, there is provided a humanized antibody or antigen-binding fragment thereof, wherein the residues at each of positions 49 and 100 (Gly (G) 49 and Thr (T) 100) with reference to SEQ ID NO: 30 of the variable domain of the heavy chain are donor residues (Ala 49 and Ala 100), see for example the sequence given in SEQ ID NO: 25 and 26.

In one embodiment, the invention provides for an antibody or antigen-binding fragment thereof comprising:
1. a light chain variable region according to SEQ ID NO: 13 and a heavy chain variable region selected from SEQ ID NO: 25; or
2. a light chain variable region according to SEQ ID NO: 17 and a heavy chain variable region selected from SEQ ID NO: 25; or
3. a light chain variable region according to SEQ ID NO: 21 and a heavy chain variable region selected from SEQ ID NO: 25.

In one embodiment, the invention provides an antibody or an antigen-binding fragment thereof comprising a sequence which is 80% similar or identical to a sequence disclosed herein, for example 85%, 90%, 91%, 92%, 93%, 94%, 95% 96%, 97%, 98% or 99% over part or whole of the relevant sequence, for example a variable domain sequence, a CDR sequence or a variable domain sequence, excluding the CDRs. In one embodiment the relevant sequence is SEQ ID NO: 25. In one embodiment the relevant sequence is SEQ ID NO: 13, SEQ ID NO: 17 or SEQ ID NO: 21.

In one embodiment, the present invention provides an antibody or an antigen-binding fragment thereof which binds human alpha synuclein comprising a light chain, wherein the variable domain of the light chain comprises a sequence having at least 80%, 85%, 90%, 91%, 92%, 93%, 94%, 95% 96%, 97%, 98% or 99% identity or similarity to the sequence given in SEQ ID NO: 13, SEQ ID NO: 17 or SEQ ID NO: 21 and/or wherein the variable domain of the heavy chain comprises a sequence having at least 80%, 85%, 90%, 91%, 92%, 93%, 94%, 95% 96%, 97%, 98% or 99% identity or similarity to the sequence given in SEQ ID NO:25.

In one embodiment, the present invention provides an antibody or an antigen-binding fragment thereof which binds human alpha synuclein wherein the antibody or an antigen-binding fragment thereof has a light chain variable domain which is at least 90%, 91%, 92%, 93%, 94%, 95% 96%, 97%, 98% or 99% similar or identical to the sequence given in SEQ ID NO:13, SEQ ID NO: 17 or SEQ ID NO: 21 but wherein the antibody or an antigen-binding fragment thereof has the sequence given in SEQ ID NO: 1 for CDR-L1, the sequence given in SEQ ID NO: 2 for CDR-L2 and the sequence given in SEQ ID NO: 3 or SEQ ID NO: 7 for CDR-L3.

In one embodiment, the present invention provides an antibody or an antigen-binding fragment thereof which binds human alpha synuclein wherein the antibody or an antigen-binding fragment thereof has a heavy chain variable domain which is at least 90%, 91%, 92%, 93%, 94%, 95% 96%, 97%, 98% or 99% similar or identical to the sequence given in SEQ ID NO: 25 but wherein the antibody or an antigen-binding fragment thereof has the sequence given in SEQ ID NO: 4 for CDR-H1, the sequence given in SEQ ID NO: 5 for CDR-H2 and the sequence given in SEQ ID NO: 6 for CDR-H3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
 lysine, arginine and histidine (amino acids having basic side chains);
 aspartate and glutamate (amino acids having acidic side chains);
 asparagine and glutamine (amino acids having amide side chains); and
 cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In one embodiment the antigen-binding fragment may be, but is not limited to, a Fab, modified Fab, Fab', modified Fab', F(ab')2, Fv, single domain antibodies (e.g. VH or VL or VHH), scFv, dsscFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in WO2005/003169, WO2005/003170 and WO2005/003171. Multi-valent antibodies may comprise multiple specificities e.g. bispecific or may be monospecific (see for example WO 92/22853, WO05/113605, WO2009/040562 and WO2010/035012).

An alternative antigen-binding fragment comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in International Patent Application Publication No, WO2015/197772, which is hereby incorporated by reference in its entirety and particularly with respect to the discussion of antibody fragments.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required. It will be appreciated that sequence variants of these constant region domains may also be used. For example, IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment a C-terminal amino acid from the antibody is cleaved during post-translation modifications.

In one embodiment an N-terminal amino acid from the antibody is cleaved during post-translation modifications.

In another embodiment, the antibody of the present invention may comprise a complete antibody having full length heavy and light chains or an antigen-binding fragment thereof. For example, the full-length antibody is selected from an IgG1, IgG4 or an IgG4P.

In one embodiment the antibody or antigen-binding fragment thereof comprises:
 1. a light chain according to SEQ ID NO: 14 and a heavy chain according to SEQ ID NO: 26; or
 2. a light chain according to SEQ ID NO: 18 and a heavy chain according to SEQ ID NO: 26; or
 3. a light chain according to SEQ ID NO: 22 and a heavy chain according to SEQ ID NO: 26.

In one embodiment the antibody according to the present disclosure is provided as alpha synuclein binding antibody fusion protein which comprises an immunoglobulin moiety, for example a Fab or Fab' fragment, and one or two single domain antibodies (dAb) linked directly or indirectly thereto, for example as described in WO2009/040562, WO2010035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment, the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

In one embodiment, the antibody or an antigen-binding fragment thereof comprises a light variable region according to SEQ ID NO: 13 or 17 or 21 and a heavy variable region selected from SEQ ID NO: 25. For example, the antibody is a full length IgG4 antibody comprising a light variable region according to SEQ ID NO: 13 or 17 or 21 and a heavy variable region selected from SEQ ID NO: 25. In another example, the antibody is full length IgG4 antibody comprising a light chain according to SEQ ID NO: 14, 18 or 22 and a heavy chain according to SEQ ID NO: 26. In yet another example the antigen-binding fragment is a Fab' comprising a light variable region according to SEQ ID NO: 13, 17 or 21 and a heavy variable region selected from SEQ ID NO: 25.

In one preferred embodiment, the antibody or antigen-binding fragment thereof or the pharmaceutical composition comprising the antibody or antigen-binding fragment thereof for use in therapy is an antibody or antigen-binding fragment thereof comprising:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof binds to alpha synuclein to an epitope comprising, with reference to SEQ ID NO: 8, at least residues D119, N122 and Y125.

Even more preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the anti-alpha synuclein antibody or antigen-binding fragment thereof according to the present invention may be engineered to have an appropriate isoelectric point. This may lead to antibodies and/or fragments with more robust properties, in particular suitable solubility and/or stability profiles and/or improved purification characteristics.

Thus, in one aspect the invention provides a humanized anti alpha synuclein antibody or antigen-binding fragment thereof engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value, acidic residues may be introduced to lower the pI, as required. It is important that when manipulating the pI care must be taken to retain the desirable activity of the antibody or fragment. Thus, in one embodiment the engineered antibody or antigen-binding fragment thereof has the same or substantially the same activity as the "unmodified" antibody or fragment.

Programs such as ** ExPASY http://www.expasy.ch/tools/pi_tool.html, and http://www.iut-arles.up.univ-mrs.fr/w3bb/d_abim/compo-p.html, may be used to predict the isoelectric point of the antibody or fragment.

It will be appreciated that the affinity of antibodies provided by the present invention may be altered using any suitable method known in the art. The present invention therefore also relates to variants of the antibody molecules of the present invention, which have an improved affinity for alpha synuclein, in particular human alpha synuclein. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

If desired, the antibody or antigen-binding fragment thereof according to the present invention may be conjugated to one or more effector molecule(s). It will be appreciated that the effector molecule may comprise a single effector molecule or two or more such molecules so linked as to form a single moiety that can be attached to the antibodies or antigen-binding fragment thereof of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, AL, USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

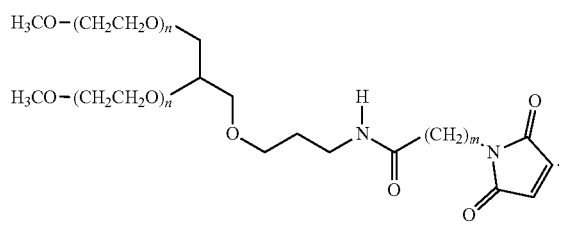

m is 2 or 5

That is to say each PEG is about 20,000 Da.

Thus, in one embodiment the PEG is 2,3-Bis(methylpolyoxyethylene-oxy)-1-{[3-(6-maleimido-1-oxohexyl) amino]propyloxy} hexane (the 2 arm branched PEG, —CH2) 3NHCO(CH2)5-MAL, Mw 40,000 known as SUNBRIGHT GL2-400MA3.

Further alternative PEG effector molecules of the following type:

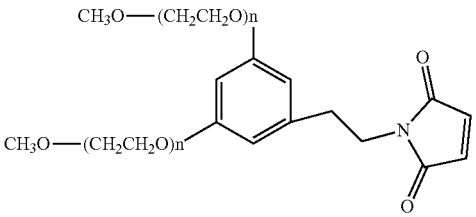

are available from Dr Reddy, NOF and Jenkem.

In one embodiment the Fab or Fab' according to the present invention is conjugated to a PEG molecule.

In one embodiment there is provided an antibody which is PEGylated (for example with a PEG described herein), attached through a cysteine amino acid residue at or about amino acid 226 in the chain, for example amino acid 226 of the heavy chain (by sequential numbering), for example amino acid 224 of SEQ ID NO:26.

In one embodiment the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one embodiment there is provided a Fab' conjugated to a polymer, such as a PEG molecule, a starch molecule or an albumin molecule. In one embodiment there is provided a scFv conjugated to a polymer, such as a PEG molecule, a starch molecule or an albumin molecule. In one embodiment the Fab or Fab' according to the present disclosure is conjugated to human serum albumin. In one embodiment the antibody or fragment is conjugated to a starch molecule, for example to increase the half-life. Methods of conjugating starch to a protein as described in U.S. Pat. No. 8,017,739 incorporated herein by reference.

The present invention also provides an isolated polynucleotide encoding the antibody or antigen-binding fragment thereof according to the present invention. The isolated polynucleotide according to the present invention may comprise synthetic DNA, for instance produced by chemical processing, cDNA, genomic DNA or any combination thereof.

Standard techniques of molecular biology may be used to prepare DNA sequences coding for the antibody or antigen-binding fragment thereof of the present invention. Desired DNA sequences may be synthesized completely or in part using oligonucleotide synthesis techniques. Site-directed mutagenesis and polymerase chain reaction (PCR) techniques may be used as appropriate.

In one embodiment, the isolated polynucleotide according to the invention encodes:
 a. a light chain variable region, wherein the polynucleotide:
  i. is at least 90% identical to SEQ ID NO: 15 or SEQ ID NO: 19 or SEQ ID NO: 23; or ii. comprises SEQ ID NO: 15 or SEQ ID NO: 19 or SEQ ID NO: 23; or
iii. consists essentially of SEQ ID NO: 15 or SEQ ID NO: 19 or SEQ ID NO: 23;
b. a heavy chain variable region, wherein the polynucleotide:
  i. is at least 90% identical to SEQ ID NO: 27; or
  ii. comprises SEQ ID NO: 27; or
  iii. consists essentially of SEQ ID NO: 27;
c. a light chain, wherein the polynucleotide:
  i. is at least 90% identical to SEQ ID NO: 16 or SEQ ID NO: 20 or SEQ ID NO: 24; or
  ii. comprises SEQ ID NO: 16 or SEQ ID NO: 20 or SEQ ID NO: 24; or
  iii. consists essentially of SEQ ID NO: 16 or SEQ ID NO: 20 or SEQ ID NO: 24;
d. a heavy chain, wherein the polynucleotide:
  i. is at least 90% identical to SEQ ID NO: 28; or
  ii. comprises SEQ ID NO: 28; or
  iii. consists essentially of SEQ ID NO: 28.

The present invention also provides for a cloning or expression vector comprising one or more polynucleotides described herein. In one example, the cloning or expression vector according to the present invention comprises one or more isolated polynucleotides comprising a sequence selected from SEQ ID NO: 15, 16, 19, 20, 23, 24, 27 or 28.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more isolated polynucleotide sequences according to the invention or one or more cloning or expression vectors comprising one or more isolated polynucleotide sequences encoding an antibody of the present invention. Any suitable host cell/vector system may be used for expression of the polynucleotide sequences encoding the antibody or antigen-binding fragment thereof of the present invention. Bacterial, for example E. coli, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr-CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NSO myeloma cells and SP2 cells, COS cells. The host cell may be stably transformed or transfected with the isolated polynucleotide sequences or the expression vectors according to the present invention.

In one embodiment the host cell according to the present invention is a CHO-DG44 cell stably transfected with an expression vector comprising the isolated polynucleotide sequences of the present invention, preferably comprising the isolated polynucleotide sequences according to SEQ ID NO: 15 and 27 or SEQ ID NO: 19 and 27 or SEQ ID NO: 23 and 27 or SEQ ID NO: 16 and 28 or SEQ ID NO: 20 and 28 or SEQ ID NO: 24 and 28.

The present invention also provides a process for the production of an antibody or an antigen-binding fragment thereof according to the present invention comprising culturing a host cell according to the present invention under conditions suitable for producing the antibody or antigen-binding fragment thereof according to the invention, and isolating the antibody or antigen-binding fragment thereof.

The antibody or antigen-binding fragment thereof may comprise only a heavy or light chain polypeptide, in which case only a heavy chain or light chain polypeptide coding sequence needs to be used to transfect the host cells. For production of antibodies or antigen-binding fragments thereof comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Thus, there is provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

Thus in one embodiment there is provided a purified anti-alpha synuclein antibody or fragment thereof, for example a humanized antibody or fragment thereof, in particular an antibody or fragment thereof according to the invention, in substantially purified from, in particular free or substantially free of endotoxin and/or host cell protein or DNA.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

As the antibodies of the present invention are useful in the treatment, diagnosis and/or prophylaxis of a pathological condition such as an alpha synucleinopathy, the present invention also provides for a pharmaceutical or diagnostic composition comprising an antibody or antigen-binding fragment thereof according to the present invention in combination with one or more of a pharmaceutically acceptable carrier, excipient or diluent. In one embodiment the antibody or antigen-binding fragment thereof according to the present invention is the sole active ingredient. In another embodiment, the antibody or antigen-binding fragment thereof according to the present invention is in combination with one or more additional active ingredients. Alternatively, the pharmaceutical compositions comprise the antibody or antigen-binding fragment thereof according to the present invention which is the sole active ingredient and it may be administered individually to a patient in combination (e.g. simultaneously, sequentially or separately) with other agents, drugs or hormones.

In another embodiment, the pharmaceutical composition comprises an antibody or antigen-binding fragment thereof comprising a light chain variable region of SEQ ID NO: 13 or 17 or 21 and comprising a heavy chain variable region of SEQ ID NO: 25, for example SEQ ID NO: 13 and SEQ ID NO: 25 or SEQ ID NO: 17 and SEQ ID NO: 25 or SEQ ID NO: 21 and SEQ ID NO: 25.

The pharmaceutical compositions according to the invention may be administered suitably to a patient to identify the therapeutically effective amount required. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion, in intravenous, inhalable or sub-cutaneous form. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody or antigen-binding fragment thereof according to the invention may be in dry form, for reconstitution before use with an appropriate sterile liquid. Solid forms suitable for solution in, or suspension in, liquid vehicles prior to injection may also be prepared.

Once formulated, the compositions of the invention can be administered directly to the subject. Accordingly, provided herein is the use of an antibody or an antigen-binding fragment thereof according to the invention for the manufacture of a medicament.

The subjects to be treated can be animals. Preferably, the pharmaceutical compositions according to the present invention are adapted for administration to human subjects.

Hence, in another aspect the present invention provides for the antibody or antigen-binding fragment thereof or a pharmaceutical composition comprising the antibody or antigen-binding fragment thereof for use in therapy, and in particular for use in the treatment of one or more alpha synucleinopathies. In yet another aspect, the present invention provides for method of treating one or more synucleinopathies in a patient comprising administering to said patient a therapeutically effective amount of the antibody or antigen-binding fragment thereof according to the present invention or a pharmaceutical composition comprising the antibody or antigen-binding fragment thereof.

In one embodiment, the antibody or antigen-binding fragment thereof or the pharmaceutical composition comprising the antibody or antigen-binding fragment thereof for use in therapy is an antibody or antigen-binding fragment thereof comprising:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof is humanized and prevents alpha synuclein aggregation induced by alpha synuclein fibrils, wherein the antibody or antigen-binding fragment thereof binds to alpha synuclein to an epitope comprising, with reference to SEQ ID NO: 8, at least residues D119, N122 and Y125 and wherein the antibody or antigen-binding fragment thereof is for use in therapy. Preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

In another embodiment, the antibody or antigen-binding fragment thereof or the pharmaceutical composition comprising the antibody or antigen-binding fragment thereof is for use in treating one or more synucleinopathy is an antibody or antigen-binding fragment thereof comprising:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof is humanized and prevents alpha synuclein aggregation induced by alpha synuclein fibrils, wherein the antibody or antigen-binding fragment thereof binds to alpha synuclein to an epitope comprising, with reference to SEQ ID NO: 8, at least residues D119, N122 and Y125. Preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

In another embodiment, there is provided a method of treating one or more synucleinopathies in a patient comprises administering to said patient a therapeutically effective amount of an antibody or antigen-binding fragment thereof or a pharmaceutical composition comprising the antibody or antigen-binding fragment thereof, wherein the antibody or antigen-binding fragment thereof comprises:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof is humanized and prevents alpha synuclein aggregation induced by alpha synuclein fibrils, wherein the antibody or antigen-binding fragment thereof binds to alpha synuclein to an epitope comprising, with reference to SEQ ID NO: 8, at least residues D119, N122 and Y125. Preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

Alpha synucleinopathies according to the present invention comprise, but are not limited to, Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1). Preferably, the alpha synucleinopathy is Parkinson's disease (PD).

In another embodiment, the antibody or antigen-binding fragment thereof or the pharmaceutical composition comprising the antibody or antigen-binding fragment thereof is for use in treating Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease (PD) is an antibody or antigen-binding fragment thereof comprising:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof is humanized and prevents alpha synuclein aggregation induced by alpha synuclein fibrils, wherein, optionally, the antibody or antigen-binding fragment thereof binds to alpha synuclein to an epitope comprising, with reference to SEQ ID NO: 8, at least residues D119, N122 and Y125 and wherein the antibody or antigen-binding fragment thereof is for use in therapy. Preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

In another embodiment, there is provided a method of treating Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), preferably Parkinson's disease (PD), in a patient comprises administering to said patient a therapeutically effective amount of an antibody or antigen-binding fragment thereof or a pharmaceutical composition comprising the antibody or antigen-binding fragment thereof, wherein the antibody or antigen-binding fragment thereof comprises:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof is humanized and prevents alpha synuclein aggregation induced by alpha synuclein fibrils, wherein, optionally, the antibody or antigen-binding fragment thereof binds to alpha synuclein to an epitope comprising, with reference to SEQ ID NO: 8, at least residues D119, N122 and Y125 and wherein the antibody or antigen-binding fragment thereof is for use in therapy. Preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

Alternatively, the invention also provides for the use of an antibody or an antigen-binding fragment thereof for the manufacture of a medicament for treating an alpha synucleinopathy, wherein the alpha synucleinopathy is preferably Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1), more preferably Parkinson's disease (PD), wherein the antibody or antigen-binding fragment thereof comprises:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein the antibody or antigen-binding fragment thereof is humanized and prevents alpha synuclein aggregation induced by alpha synuclein fibrils, wherein, optionally, the antibody or antigen-binding fragment thereof binds to alpha synuclein to an epitope comprising, with reference to SEQ ID NO: 8, at least residues D119, N122 and Y125 and wherein the antibody or antigen-binding fragment thereof is for use in therapy. Preferably the antibody or antigen-binding fragment thereof does not cross-react with beta-synuclein and binds alpha synuclein with a constant of dissociation ($K_D$) at least 10-fold higher for monomeric alpha synuclein than for alpha synuclein in fibrils.

Also part of the present invention is the use of the anti-alpha synuclein antibodies or antigen-binding fragments for use as diagnostically active agents or in diagnostic assays, for example for diagnosing alpha synucleinopathies such as Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

The diagnosis may preferably be performed on biological samples. A "biological sample" encompasses a variety of sample types obtained from an individual and can be used in a diagnostic or monitoring assay. The definition encompasses cerebrospinal fluid, blood such as plasma and serum, and other liquid samples of biological origin such as urine and saliva, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides.

Diagnostic testing may preferably be performed on biological samples which are not in contact with the human or animal body. Such diagnostic testing is also referred to as in vitro testing. In vitro diagnostic testing may rely on an in vitro method of detecting alpha synuclein in a biological sample which has been obtained from an individual comprising the steps of i) contacting the biological sample with anti-alpha synuclein antibody or antigen-binding fragment thereof as described herein; and ii) detecting binding of the anti-alpha synuclein antibody or antigen-binding fragment thereof to alpha synuclein. By comparing the detected alpha synuclein level or the presence of a specific post-translationally modified form of alpha synuclein with a suitable control, one or more alpha synucleinopathies may be identified. Such a detection method can thus be used to determine whether a subject has, or is at risk of developing, an alpha synucleinopathy, including determining the stage (severity) of an alpha synucleinopathy.

Therefore, the present invention provides for an antibody or an antigen-binding fragment thereof for use in the diagnosis of an alpha synucleinopathies, preferably in the diagnosis of Parkinson's disease (PD), wherein the antibody or antigen-binding fragment thereof comprises:

a. a light chain variable region comprising a CDR-L1 according to SEQ ID NO: 1; a CDR-L2 according to SEQ ID NO: 2 and a CDR-L3 according to SEQ ID NO: 3 or SEQ ID NO: 7; and a heavy chain variable region comprising a CDR-H1 according to SEQ ID NO: 4; a CDR-H2 according to SEQ ID NO: 5 and a CDR-H3 according to SEQ ID NO: 6; or b. a light variable region according to SEQ ID NO: 13 or SEQ ID NO: 17 or SEQ ID NO: 21 and a heavy variable region selected from SEQ ID NO: 25; or c. a light chain according to SEQ ID NO: 14 or SEQ ID NO: 18 or SEQ ID NO: 22 and a heavy chain according SEQ ID NO: 26;

wherein, optionally, the antibody or antigen-binding fragment thereof binds to alpha synuclein to an epitope comprising, with reference to SEQ ID NO: 8, at least residues D119, N122 and Y125.

The sequences included in the present invention are shown in Table 1:

TABLE 1

| Name | SEQ ID NO: | SEQUENCE |
|---|---|---|
| CDR-L1 | 1 | KASQNINKNLD |
| CDR-L2 | 2 | YANNLQT |
| CDR-L3 | 3 | YQYKNGWT |
| CDR-H1 | 4 | GETFNNAAMY |
| CDR-H2 | 5 | RIRTKPNNYATSYADSVKG |
| CDR-H3 | 6 | DYSRGDR |
| CDR-L3 variant 1 | 7 | YQYKNAWT |
| Human alpha synuclein P37840 | 8 | MDVFMKGLSKAKEGVVAAAEKTKQGVAEAAGKTKEGVLYVGSKTKEGVVHGVATV AEKTKEQVTNVGGAVVTGVTAVAQKTVEGAGSIAAATGFVKKDQLGKNEEGAPQE GILEDMPVDPDNEAYEMPSEEGYQDYEPEA |
| Rat VL 5811 | 9 | NIQMTQSPPVLSASVGDRVTLSCKASQNINKNLDWYQQKHGEAPKLLMYYANNLQ TGIPSRFSGSGSGTDYTLTISSLQPEDVATYYCYQYKNGWTEGGGTKLELK |
| Rat VH 5811 | 10 | EMQLVESGGGLVQPKESLKISCAASGETFNNAAMYWVRQAPGKGLEWVARIRTKP NNYATSYADSVKGRFTISRDDSKSMVYLQMDNLKSEDTAMYYCTADYSRGDRWGQ GVMVTVSS |

TABLE 1-continued

| Name | SEQ ID NO: | SEQUENCE |
| --- | --- | --- |
| Rat VL nucleotide | 11 | aacatccagatgacccagtctcctccagtcctgtctgcatctgtgggagacagag tcactctcagctgcaaagcaagtcagaacattaataagaacttagactggtatca gcaaaagcatggagaagctccaaaactcctgatgtattatgcaaacaatttacaa acgggcatcccatcaaggttcagtggcagtggatctggaacagattacacgctca ccatcagcagcctgcagcctgaagatgttgccacatattactgctatcagtataa gaatgggtggacgttcggtggaggcaccaagctggaactgaaa |
| Rat VH nucleotide | 12 | Gaaatgcagctggtggagtctggtggaggattggtgcagcctaaggagtcattga aaatctcatgtgcagcctctggattcaccttcaataatgctgccatgtactgggt ccgccaggctccaggaaagggtctggaatgggttgctcgcataagaactaaacct aataattatgcaacatcttatgctgattcagtgaaaggcagattcaccatctcca gagatgattcaaaaagcatggtctacctacaaatggataacttgaaaagtgagga cacagccatgtattactgtacagcagattactccagaggtgacaggtggggccaa ggagtcatggtcacagtctcgagc |
| 5811 gL5 V-region | 13 | DIQMTQSPSSLSASVGDRVTITCKASQNINKNLDWYQQKPGKAPKLLIYYANNLQ TGVPSRFSGSGSGTDYTLTISSLQPEDFATYYCYQYKNGWTEGQGTKVEIK |
| 5811 gL5 Light chain | 14 | DIQMTQSPSSLSASVGDRVTITCKASQNINKNLDWYQQKPGKAPKLLIYYANNLQ TGVPSRFSGSGSGTDYTLTISSLQPEDFATYYCYQYKNGWTEGQGTKVEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| 5811 gL5 V-region nucleotide | 15 | Gacatccagatgacccagagcccgagctccctgtccgcatcagtgggggatcgcg tgactattacgtgcaaagcctcgcagaacatcaacaagaacctcgactggtatca gcagaagccaggaaaggcgcctaagctgctgatctactacgccaacaatctccag accggcgtgccctcgcggttctccggatctgggtccggtactgattacacccctga ccattagctcccttcaaccggaggacttcgccacctattactgctaccagtacaa gaacggctggacttttggacaaggcaccaaggtcgaaatcaag |
| 5811 gL5 Light chain nucleotide | 16 | Gacatccagatgacccagagcccgagctccctgtccgcatcagtgggggatcgcg tgactattacgtgcaaagcctcgcagaacatcaacaagaacctcgactggtatca gcagaagccaggaaaggcgcctaagctgctgatctactacgccaacaatctccag accggcgtgccctcgcggttctccggatctgggtccggtactgattacacccctga ccattagctcccttcaaccggaggacttcgccacctattactgctaccagtacaa gaacggctggacttttggacaaggcaccaaggtcgaaatcaagcgtacggtggcc gctcccctccgtgttcatcttcccaccctcgacgagcagctgaagtccggcaccg cctccgtcgtgtgcctgctgaacaacttctaccccgcgaggccaaggtgcagtg gaaggtggacaacgccctgcagtccggcaactcccaggaatccgtcaccgagcag gactccaaggacagcacctactccctgtcctccaccctgaccctgtccaaggccg actacgagaagcacaaggtgtacgcctgcgaagtgacccaccagggcctgtccag ccccgtgaccaagtccttcaaccggggcgagtgc |
| 5811 gL8 V-region | 17 | DIQMTQSPSSLSASVGDRVTITCKASQNINKNLDWYQQKPGKAPKLLIYYANNLQ TGVPSRFSGSGSGTDFTLTISSLQPEDFATYYCYQYKNGWTFGQGTKVEIK |
| 5811 gL8 Light chain | 18 | DIQMTQSPSSLSASVGDRVTITCKASQNINKNLDWYQQKPGKAPKLLIYYANNLQ TGVPSRFSGSGSGTDFTLTISSLQPEDFATYYCYQYKNGWTFGQGTKVEIKRTVA APSVFIFPPSDEQLKSGTASVVCLLNNFYPREAKVQWKVDNALQSGNSQESVTEQ DSKDSTYSLSSTLTLSKADYEKHKVYACEVTHQGLSSPVTKSFNRGEC |
| 5811 gL8 V-region nucleotide | 19 | Gacatccagatgacccagagcccgagctccctgtccgcatcagtgggggatcgcg tgactattacgtgcaaagcctcgcagaacatcaacaagaacctcgactggtatca gcagaagccaggaaaggcgcctaagctgctgatctactacgccaacaatctccag accggcgtgccctcgcggttctccggatctgggtccggtactgattcacccctga ccattagctcccttcaaccggaggacttcgccacctattactgctaccagtacaa gaacggctggacttttggacaaggcaccaaggtcgaaatcaag |
| 5811 gL8 Light chain nucleotide | 20 | Gacatccagatgacccagagcccgagctccctgtccgcatcagtgggggatcgcg tgactattacgtgcaaagcctcgcagaacatcaacaagaacctcgactggtatca gcagaagccaggaaaggcgcctaagctgctgatctactacgccaacaatctccag accggcgtgccctcgcggttctccggatctgggtccggtactgattcacccctga ccattagctcccttcaaccggaggacttcgccacctattactgctaccagtacaa gaacggctggacttttggacaaggcaccaaggtcgaaatcaagcgtacggtggcc gctcccctccgtgttcatcttcccaccctcgacgagcagctgaagtccggcaccg cctccgtcgtgtgcctgctgaacaacttctaccccgcgaggccaaggtgcagtg gaaggtggacaacgccctgcagtccggcaactcccaggaatccgtcaccgagcag gactccaaggacagcacctactccctgtcctccaccctgaccctgtccaaggccg actacgagaagcacaaggtgtacgcctgcgaagtgacccaccagggcctgtccag ccccgtgaccaagtccttcaaccggggcgagtgc |
| 5811 gL14 V-region | 21 | DIQMTQSPSSLSASVGDRVTITCKASQNINKNLDWYQQKPGKAPKLLIYYANNLQ TGVPSRFSGSGSGTDFTLTISSLQPEDFATYYCYQYKNAWTFGQGTKVEIK |

TABLE 1-continued

| Name | SEQ ID NO: | SEQUENCE |
|---|---|---|
| 5811 gL14 Light chain | 22 | DIQMTQSPSSLSASVGDRVTITCKASQNINKNLDWYQQKPGKAPKLLIYYANNLQ<br>TGVPSRFSGSGSGTDFTLTISSLQPEDFATYYCYQYKNAWTFGQGTKVEIKRTVA<br>APSVFIFPPSDEQLKSGTASVVCLLNNFYPREAKVQWKVDNALQSGNSQESVTEQ<br>DSKDSTYSLSSTLTLSKADYEKHKVYACEVTHQGLSSPVTKSFNRGEC |
| 5811 gL14 V-region nucleotide | 23 | Gacatccagatgacccagagcccgagctcccctgtccgcatcagtgggggatcgcg<br>tgactattacgtgcaaagcctcgcagaacatcaacaagaacctcgactggtatca<br>gcagaagccaggaaaggcgcctaagctgctgatctactacgccaacaatctccag<br>accggcgtgccctcgcggttctccggatctgggtccggtactgatttcaccctga<br>ccattagctcccttcaaccggaggacttcgccacctattactgctaccagtacaa<br>gaacgcttggacttttggacaaggcaccaaggtcgaaatcaag |
| 5811 gL14 Light chain nucleotide | 24 | Gacatccagatgacccagagcccgagctcccctgtccgcatcagtgggggatcgcg<br>tgactattacgtgcaaagcctcgcagaacatcaacaagaacctcgactggtatca<br>gcagaagccaggaaaggcgcctaagctgctgatctactacgccaacaatctccag<br>accggcgtgccctcgcggttctccggatctgggtccggtactgatttcaccctga<br>ccattagctcccttcaaccggaggacttcgccacctattactgctaccagtacaa<br>gaacgcttggacttttggacaaggcaccaaggtcgaaatcaagcgtacggtggcc<br>gctcccctcgtgttcatcttcccaccctcgacgagcagctgaagtccggcaccg<br>cctcgtcgtgtgcctgctgaacaacttctaccccgcgaggccaaggtgcagtg<br>gaaggtggacaacgccctgcagtccggcaactcccaggaatccgtcaccgagcag<br>gactccaaggacagcacctactccctgtcctccaccctgaccctgtccaaggccg<br>actacgagaagcacaaggtgtacgcctgcgaagtgacccaccagggcctgtccag<br>ccccgtgaccaagtccttcaaccggggcgagtgc |
| 5811 gH4 V-region | 25 | EVQLVESGGGLVKPGGSLRLSCAASGETFNNAAMYWVRQAPGKGLEWVARIRTKP<br>NNYATSYADSVKGRFTISRDDSKNTLYLQMNSLKTEDTAVYYCTADYSRGDRWGQ<br>GTMVTVSS |
| 5811 gH4 Heavy chain | 26 | EVQLVESGGGLVKPGGSLRLSCAASGETFNNAAMYWVRQAPGKGLEWVARIRTKP<br>NNYATSYADSVKGRFTISRDDSKNTLYLQMNSLKTEDTAVYYCTADYSRGDRWGQ<br>GTMVTVSSASTKGPSVFPLAPCSRSTSESTAALGCLVKDYFPEPVTVSWNSGALT<br>SGVHTFPAVLQSSGLYSLSSVVTVPSSSLGTKTYTCNVDHKPSNTKVDKRVESKY<br>GPPCPPCPAPEFLGGPSVFLEPPKPKDTLMISRTPEVTCVVVDVSQEDPEVQFNW<br>YVDGVEVHNAKTKPREEQFNSTYRVVSVLTVLHQDWLNGKEYKCKVSNKGLPSSI<br>EKTISKAKGQPREPQVYTLPPSQEEMTKNQVSLTCLVKGFYPSDIAVEWESNGQP<br>ENNYKTTPPVLDSDGSFELYSRLTVDKSRWQEGNVFSCSVMHEALHNHYTQKSLS<br>LSLGK |
| 5811 gH4 V-region nucleotide | 27 | Gaagtgcagcttgtggagagcggaggtggactcgtgaagcctggcggatctctgc<br>gcctgtcctgcgccgcctcgggggttcacctttaacaatgccgcaatgtattgggt<br>cagacaggcccgggaaagggtttggaatgggtggctaggattcggactaagccc<br>aacaactacgcgacctcctacgccgatagcgtgaagggcagattcaccatctccc<br>gggacgactcaaagaacacgctgtacctccaaatgaactccctgaaaaccgagga<br>caccgccgtgtactactgcaccgcggactactccggggcgatcgctggggacag<br>gggactatggtcactgtctcgagt |
| 5811 gH4 Heavy chain nucleotide | 28 | gaagtgcagcttgtggagagcggaggtggactcgtgaagcctggcggatctctgc<br>gcctgtcctgcgccgcctcgggggttcacctttaacaatgccgcaatgtattgggt<br>cagacaggcccgggaaagggtttggaatgggtggctaggattcggactaagccc<br>aacaactacgcgacctcctacgccgatagcgtgaagggcagattcaccatctccc<br>gggacgactcaaagaacacgctgtacctccaaatgaactccctgaaaaccgagga<br>caccgccgtgtactactgcaccgcggactactccggggcgatcgctggggacag<br>gggactatggtcactgtctcgagtgcctccaccaagggcccctccgtgttccctc<br>tggccccttgctccggtccacctccgagtctaccgcgctctgggctgcctggt<br>caaggactacttccccgagcccgtgacagtgtcctggaactctggcgccctgacc<br>tccggcgtgcacaccttccctgccgtgctgcagtcctccgggctgtactcctgt<br>cctccgtcgtgaccgtgccctcctcagcctgggcaccaagacctacacctgtaa<br>cgtggaccacaagccttccaacaccaaggtggacaagcgggtggaatctaagtac<br>ggccctccctgccccccctgccctgccctgaatttctggggcgaccttccgtgt<br>tcctgttccccccaaagcccaaggacaccctgatgatctcccggaccccgaagt<br>gacctgcgtggtggtggacgtgtcccaggaagatcccgaggtccagttcaattgg<br>tacgtggacggcgtggaagtgcacaatgccaagaccaagcccagagaggaacagt<br>tcaactccacctaccgggtggtgtccgtgctgaccgtgctgcaccaggactggct<br>gaacggcaaagagtacaagtgcaaggtgtccaacaagggcctgccctccagcatc<br>gaaaagaccatctccaaggccaagggccagccccgcgagccccaggtgtacaccc<br>tgccccctagccaggaagagatgaccaagaaccaggtgtccctgacctgtctggt<br>caagggcttctacccctccgacattgccgtggaatggagtccaacggccagccc<br>gagaacaactacaagaccaccccccctgtgctggacagcgacggctccttcttcc<br>tgtactctcggctgaccgtggacaagtccgtggcaggaaggcaacgtcttctc<br>tgctccgtgatgcacgaggccctgcacaaccactacacccagaagtccctgtcc<br>ctgagcctgggcaag |

TABLE 1-continued

| Name | SEQ ID NO: | SEQUENCE |
|---|---|---|
| Human IGKV1-39 JK1 acceptor framework | 29 | DIQMTQSPSSLSASVGDRVTITCRASQSISSYLNWYQQKPGKAPKLLIYAASSLQ SGVPSRFSGSGSGTDFTLTISSLQPEDFATYYCQQSYSTPWTEGQGTKVEIK |
| Human IGHV3-15 JH3 acceptor framework | 30 | EVQLVESGGGLVKPGGSLRLSCAASGFTFSNAWMSWVRQAPGKGLEWVGRIKSKT DGGTTDYAAPVKGRFTISRDDSKNTLYLQMNSLKTEDTAVYYCTTDAFDVWGQGT MVTVSS |
| Human IGKV1-39 JK1 acceptor framework nucleotide | 31 | gacatccagatgacccagtctccatcctccctgtctgcatctgtaggagacagag tcaccatcacttgccgggcaagtcagagcattagcagctatttaaattggtatca gcagaaaccagggaaagcccctaagctcctgatctatgctgcatccagtttgcaa agtggggtcccatcaaggttcagtggcagtggatctgggacagatttcactctca ccatcagcagtctgcaacctgaagattttgcaacttactactgtcaacagagtta cagtaccccttggacgttcggccaagggaccaaggtggaaatcaaa |
| Human IGHV3-15 JH3 acceptor framework nucleotide | 32 | Gaggtgcagctggtggagtctgggggaggcttggtaaagcctggggggtcccttagactctcctgtgcagcctctggattcactttcagtaacgcctggatgagctgggtccgccaggctccagggaaggggctggagtgggttggccgtattaaaagcaaaactgatggtgggacaacagactacgctgcaccegtgaaaggcagattcaccatctcaagagatgattcaaaaaacacgctgtatctgcaaatgaacagcctgaaaaccgaggacacagccgtgtattactgtaccacagatgcttttgatgtctggggccaagggacaatggtcaccgtctcttca |
| Rabbit Fc human 68-140 a-syn | 33 | GAVVTGVTAVAQKTVEGAGSIAAATGFVKKDQLGKNEEGAPQEGILEDMPVDPDN EAYEMPSEEGYQDYEPEAVEKTVAPSTCSKPTCPPPELLGGPSVFIFPPKPKDTL MISRTPEVTCVVVDVSQDDPEVQFTWYINNEQVRTARPPLREQQFNSTIRVVSTL PIAHQDWLRGKEEKCKVHNKALPAPIEKTISKARGQPLEPKVYTMGPPREELSSR SVSLTCMINGFYPSDISVEWEKNGKAEDNYKTTPAVLDSDGSYFLYSKLSVPTSE WQRGDVFTCSVMHEALHNHYTQKSISRSPGK |
| 5811 rat-mouse chimeric light chain | 34 | NIQMTQSPPVLSASVGDRVTLSCKASQNINKNLDWYQQKHGEAPKLLMYYANNLQ TGIPSRFSGSGSGTDYTLTISSLQPEDVATYYCYQYKNGWTEGGGTKLELKRTDA APTVSIFPPSSEQLTSGGASVVCFLNNEYPKDINVKWKIDGSERQNGVLNSWTDQ DSKDSTYSMSSTLTLTKDEYERHNSYTCEATHKTSTSPIVKSFNRNEC |
| 5811 rat-mouse chimeric heavy chain | 35 | EMQLVESGGGLVQPKESLKISCAASGETFNNAAMYWVRQAPGKGLEWVARIRTKP NNYATSYADSVKGRFTISRDDSKSMVYLQMDNLKSEDTAMYYCTADYSRGDRWGQ GVMVTVSSAKTTPPSVYPLAPGSAAQTNSMVTLGCLVKGYFPEPVTVTWNSGSLS SGVHTFPAVLQSDLYTLSSSVTVPSSTWPSETVTCNVAHPASSTKVDKKIVPRDC GCKPCICTVPEVSSVFIFPPKPKDVLTITLTPKVTCVVVDISKDDPEVQFSWFVD DVEVHTAQTQPREEQFNSTERSVSELPIMHQDWLNGKEEKCRVNSAAFPAPIEKT ISKTKGRPKAPQVYTIPPPKEQMAKDKVSLTCMITDFFPEDITVEWQWNGQPAEN YKNTQPIMDTDGSYFVYSKLNVQKSNWEAGNTFTCSVLHEGLHNHHTEKSLSHSP GK |
| 5811 rat-mouse chimeric Fab-HIS heavy chain | 36 | EMQLVESGGGLVQPKESLKISCAASGETFNNAAMYWVRQAPGKGLEWVARIRTKP NNYATSYADSVKGRFTISRDDSKSMVYLQMDNLKSEDTAMYYCTADYSRGDRWGQ GVMVTVSSAKTTPPSVYPLAPGSAAQTNSMVTLGCLVKGYFPEPVTVTWNSGSLS SGVHTFPAVLQSDLYTLSSSVTVPSSTWPSETVTCNVAHPASSTKVDKKIVPRDC HHHHHHHHHH |

The invention will now be further described by way of examples with references to embodiments illustrated in the accompanying drawings.

EXAMPLES

Example 1: Expression of Human Alpha Synuclein Monomer and Fibrils

A gene encoding human alpha-synuclein was generated synthetically and sub-cloned into vector pMH 10His TEV ("10His" disclosed as SEQ ID NO: 48) (containing a CMV promoter) using standard molecular biology techniques, to create a vector engineered to produce alpha synuclein with an N-terminal 10His-TEV tag ("10His" disclosed as SEQ ID NO: 48). The resulting vector was transfected into Expi293F cells using the Expi293™ Expression System (Invitrogen), following manufacturer's protocols. Alpha synuclein protein accumulated in the culture media from where it was recovered using an immobilized metal ion affinity chromatography HisTrap excel column (GE Healthcare). The column was washed with 25 mM TrisHCl, 300 mM NaCl, pH8.0, and the protein eluted with a stepped gradient of 500 mM imidazole in the same buffer. The 10His tag (SEQ ID NO: 48) was removed using TEV protease. The sample was then concentrated and desalted before reapplying the cleaved protein to the HisTrap excel column and collecting the cleaved alpha synuclein in the flow through. The alpha synuclein was further purified by gel filtration on a HiLoad 26/600 Superdex 75 column (GE Healthcare), and endotoxin removed by passage over a Proteus NoEndo cartridge (Generon). The purified alpha synuclein was confirmed to be monomeric by SEC MALS (FIG. 1A).

Figure 1B:
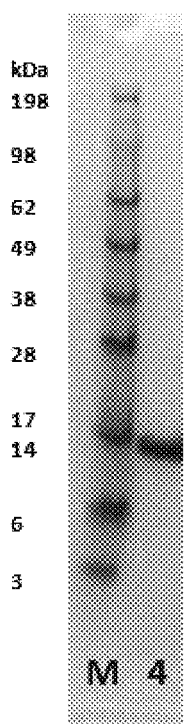
FIG. 1B SDS-PAGE of human alpha-synuclein purified from Expi293 supernatant as wildtype untagged protein. (4) Protein molecular weight marker SeeBluePlus2 (Invitrogen) (M).

Wild type (un-tagged) human alpha synuclein was also expressed in Expi293F cells. The protein was recovered from the culture media via anion exchange using a HiTrap Q column (GE Healthcare). The column was washed with 20 mM TrisHCl pH 8.0, and protein eluted using a sodium chloride gradient to 400 mM. Fractions were concentrated and desalted by passing over a HiPrep 26/10 column (GE Healthcare) and eluted with 20 mM TrisHCl pH 8.0. The protein was further purified using a MonoQ 10/100GL column, eluted with a sodium chloride gradient to 400 mM in 20 mM TrisHCl pH 8.0, followed by gel filtration on a HiLoad 26/600 Superdex 75 column (GE Healthcare), with elution in PBS pH 7.4 (FIG. 1B).

Figure 2A:
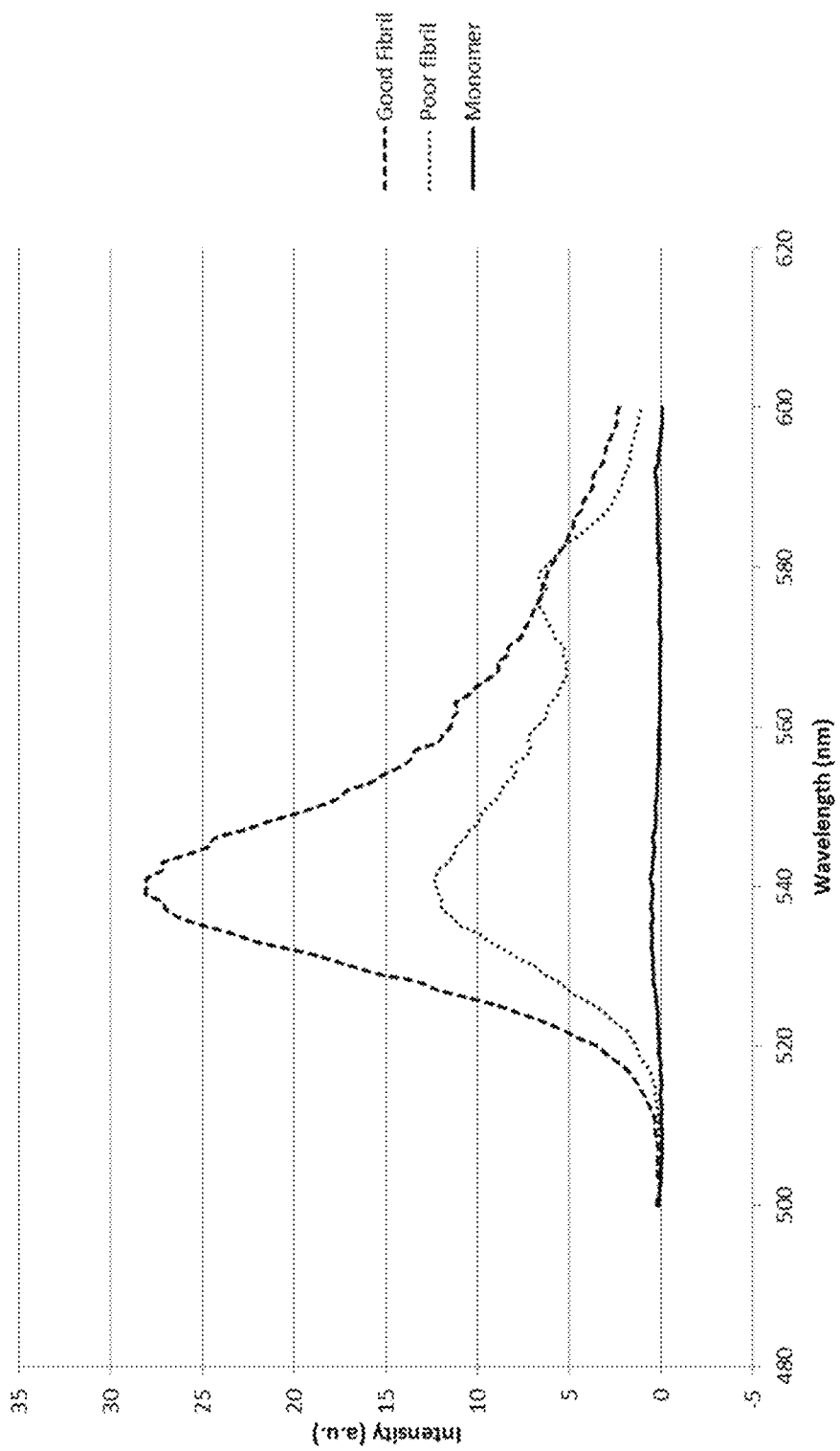
FIG. 2A Fibril analysis by JC-1 assay of a monomer with no fluorescence and of fibrils with a maximum fluorescence at 540 nm.
Figure 2B:
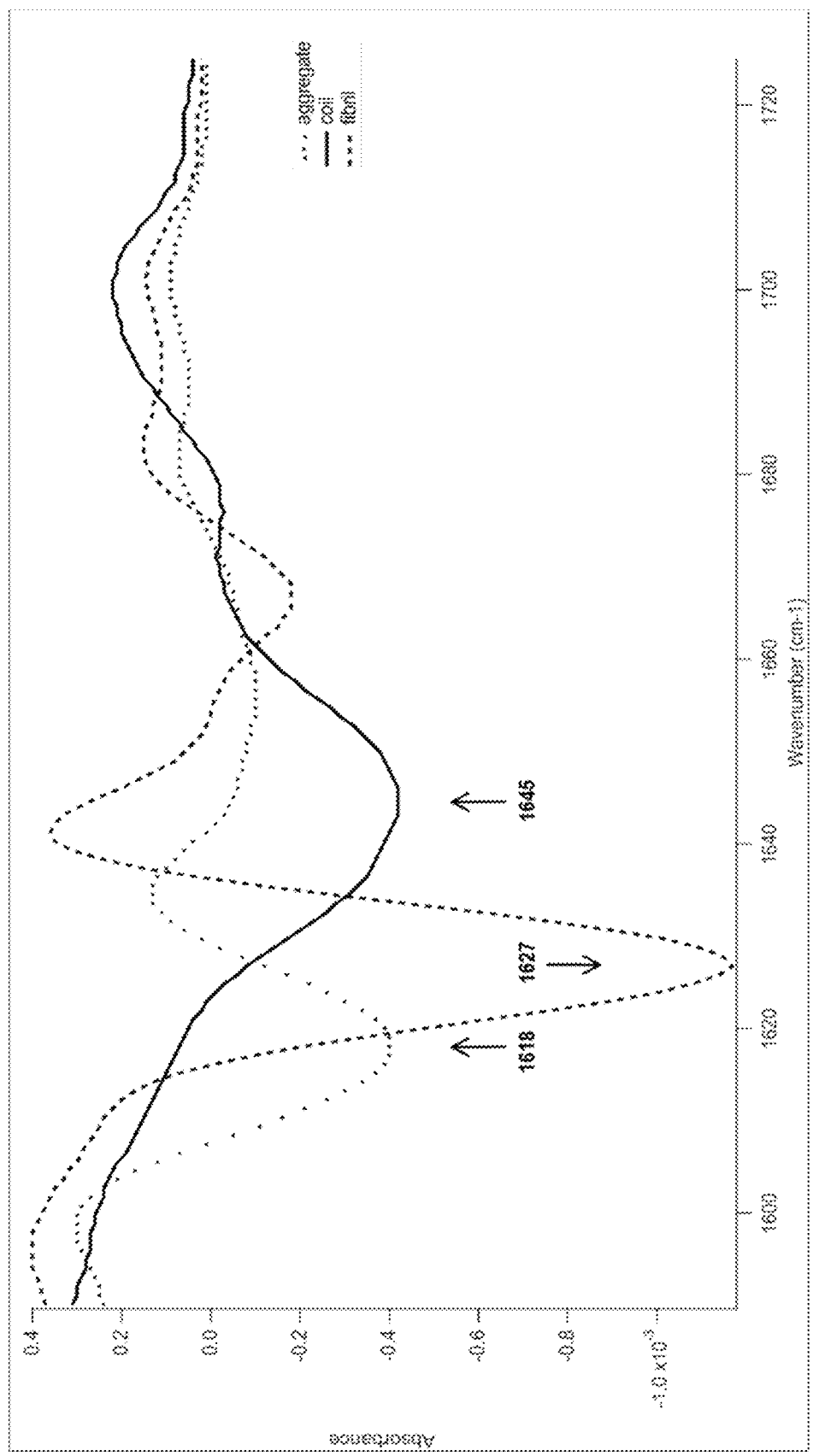
FIG. 2B Typical example for the random coil spectrum of monomeric human alpha-synuclein (wavelength 1646 $cm^{-1}$) and inter β-sheet formation in recombinant human alpha-synuclein fibrils (wavelength 1625-1630 $cm^{-1}$).

This wild type un-tagged alpha synuclein monomer was used to prepare alpha-synuclein fibrils were obtained by agitating purified, monomer (9-10 mg/mL in PBS pH7.4) at 1200 rpm, 37° C. in a Vortemp56 shaking incubator (Labnet) continuously for 10 days. Fibril formation was assessed by JC-1 assay (Lee et al., Biochem. J. 2009, 418, 311-323), and C Fourier Transform Infrared spectroscopy of the solution. Unincorporated monomer in the fibril solutions was assessed by ultracentrifugation and by passage through a 100 KDa cut-off membrane followed by gel electrophoresis. Only fibrils with a JC-1 response >15, low amount of soluble monomer (<5%) and a FTIR spectrum with the main absorption between 1625 and 1630 cm-1 were used in further studies (FIG. 2). The prepared fibrils were stored at −80° C.

Example 2: Immunization and Antibodies Isolation

Numerous immunization strategies using various species and immunogens were performed. Antibody 5811 was derived from a female Sprague Dawley rat (>180 g) which had received sub-cutaneous immunization with 50 μg of wild type un-tagged alpha synuclein monomer expressed as described above (SEQ ID NO: 8).

Rats were given 3 booster injections at 21-day intervals using incomplete Freund's adjuvant (IFA) with bleeds taken, from the tail vein, 14 days post immunization. Termination occurred 14 days after the final boost with single cell suspensions of spleen, lymph node, bone marrow and peripheral blood mononuclear cells prepared and frozen in 10% DMSO/FCS at −80° C.

B Cell Culture

B cell cultures were prepared using a method similar to that described by Tickle et al., 2015. J Biomol Screen: 20 (4), 492-497. Briefly, lymph node or splenocyte derived B cells from immunized animals were cultured at a density of approximately 2000-5000 cells per well in bar-coded 96-well tissue culture plates with 200 μl/well RPMI 1640 medium (Gibco BRL) supplemented with 10% FCS (Sigma Aldrich), 2% HEPES (Sigma Aldrich), 1% L-Glutamine (Gibco BRL), 1% penicillin/streptomycin solution (Gibco BRL), 0.1% β-mercaptoethanol (Gibco BRL), 1% activated human PBMC supernatant (BSS) and X-ray irradiated mutant EL4 murine thymoma cells ($5 \times 10^4$/well) for seven days at 37° C. in an atmosphere of 5% $CO_2$. Cultures were set up using B cells from all animals immunized, and in total, approximately $1.7 \times 10^9$ B cells were sampled.

5811, an antibody according to the present invention, was generated from activated lymph node-derived B cells which were cultured at a density of approximately 2000 cells per well. Lymph node was used in addition to splenocytes for antibody discovery to give us an alternative source of B cells from which to sample and identify novel antibodies. Approximately $3.3 \times 10^8$ cells were sampled from the full-length monomeric human alpha synuclein immunized rats.

Primary Screening

The presence of human alpha synuclein-specific antibodies in B cell culture supernatants was determined using a homogeneous fluorescence-based binding assay using Superavidin™ beads (Bangs Laboratories) coated with biotinylated recombinant human alpha synuclein full length monomer as a source of target antigen. Recombinant human alpha synuclein as described herein was biotinylated using a 3-fold molar excess of biotin. A low molar excess of biotin was used in order to avoid complete modification of all seven lysine residues that reside within the alpha synuclein molecule. Alpha synuclein monomer was incubated overnight at 40° C. with the biotin and free biotin was removed the following day using a Zeba™ spin desalting column. Screening involved the transfer of 10 μl of supernatant from barcoded 96-well tissue culture plates into barcoded 384-well black-walled assay plates containing biotinylated recombinant human alpha synuclein monomer immobilized on Superavidin beads (10 ul/well) using an Agilent Bravo liquid handler. Binding was revealed with a goat anti-rat IgG Fcγ fragment specific Alexafluor647 conjugate (Jackson). Plates were read on a TTP Labtech Mirrorball in order to identify wells containing alpha synuclein-specific IgG.

Secondary Screening

Following primary screening, positive supernatants were consolidated on 96-well bar-coded master plates using a Beckman Coulter BiomekNXP hit-picking robot and B cells in cell culture plates frozen at −80° C. Master plates were then screened in a streptavidin-capture ELISA assay using biotinylated recombinant human alpha synuclein monomer or biotinylated recombinant human alpha synuclein fibrils. This was carried out to identify wells which gave binding to both monomeric and fibrillar recombinant human alpha synuclein, and to exclude any false positive wells showing off-target binding to the Superavidin™ beads. Given the insoluble nature of the fibrils, conventional ELISA coating protocols, that are used with proteins in solution, were not favored. It was decided that a minimal biotinylation protocol be employed to preserve the fibrillar structure and to facilitate efficient coating of the fibrils on an ELISA plate pre-coated with streptavidin.

Biotinylated alpha synuclein total fibrils were generated, as described herein, by combining biotinylated recombinant alpha synuclein monomer (as described above) with a 50-fold excess of unlabeled recombinant alpha synuclein in PBS. Fibril formation was confirmed by JC1 assay (Lee et al., Biochem. J. 2009, 418, 311-323).

Biotinylated monomer or biotinylated fibrils in PBS were captured onto 384-well Maxisorp plates coated with streptavidin in a carbonate coating buffer ($dH_2O+0.16\%$ $Na_2CO_3+$ 0.3% $NaHCO_3$.) Plates were blocked with 1% w/v PEG/PBS and then incubated with 10 μl/well of B cell culture supernatant (diluted 1:1 with blocking buffer.) Secondary HRP-conjugated goat anti-rat IgG Fcγ fragment specific HRP conjugate (Jackson) was added to plates, followed by visualization of binding with TMB substrate (3,3',5,5'-Tetramethylbenzidine, from EMD Millipore; 10 μl/well). The optical density was measured at 630 nM using BioTek Synergy 2 microplate reader. The primary binding assay identified 83 hits and following ELISA screening, 29 of those were shown to bind to both monomeric and fibrillar recombinant human alpha synuclein.

B cell supernatants demonstrating strongest ELISA binding signals to recombinant fibrils were selected for further analysis by surface plasmon resonance to identify those with the best off-rate on recombinant human alpha synuclein monomer, recombinant human alpha synuclein fibrils and recombinant mouse alpha synuclein fibrils. The supernatants from 26 different B cells were tested, 19 wells gave off-rates (kd)<1×10$^{-5}$ on recombinant human alpha synuclein monomer. Of these, 6 gave off-rates (kd) of less than 1×10$^{-5}$ on recombinant mouse alpha synuclein. All 19 supernatants were selected for variable region recovery.

Variable Region Recovery

To allow recovery of antibody variable region genes from a selection of supernatants of interest, a deconvolution step had to be performed to enable identification of the antigen-specific B cells in a given well that contained a heterogeneous population of B cells. This was achieved using the Fluorescent foci method (Clargo et al., 2014. MAbs: 6(1), 143-159). Briefly, Immunoglobulin-secreting B cells from a positive well were mixed with streptavidin beads (New England Biolabs) coated with biotinylated recombinant human alpha synuclein fibrils (generated using the 1:50 mix as described above) and a 1:1200 final dilution of a goat anti-rat IgG Fcγ fragment specific FITC conjugate (Jackson). After static incubation at 37° C. for 1 hour, antigen-specific B cells could be identified due to the presence of a fluorescent halo surrounding that B cell. A number of these individual B cell clones, identified using an Olympus microscope, were then picked with an Eppendorf micromanipulator and deposited into a PCR tube.

Antibody variable region genes were recovered from single cells by reverse transcription (RT)-PCR using heavy and light chain variable region-specific primers. Two rounds of PCR were performed with the nested 2° PCR incorporating restriction sites at the 3' and 5' ends allowing cloning of the variable region into a mouse IgG Fcγ1 or Fab-10HIS (VH) or mouse kappa (VL) mammalian expression vector. Anti-alpha synuclein antibody genes from 9 different supernatants were successfully cloned into expression vectors. Heavy and light chain constructs were co-transfected into Expi-293 cells using ExpiFectamine 293 (Invitrogen) and rat-mouse chimeric recombinant antibodies 5811 mFab or 5811 mIgG1 (comprising the rat 5811 variable regions and the mouse constant regions (according to SEQ ID NO: 34 and 35 for the IgG and SEQ ID NO: 34 and 36 for the Fab) expressed in 125 ml Erlenmeyer flask in a volume of 30 ml. After 5-7 days expression, supernatants were harvested and purified using affinity chromatography.

ELISA Screening of Transient Supernatants

Figure 3A:
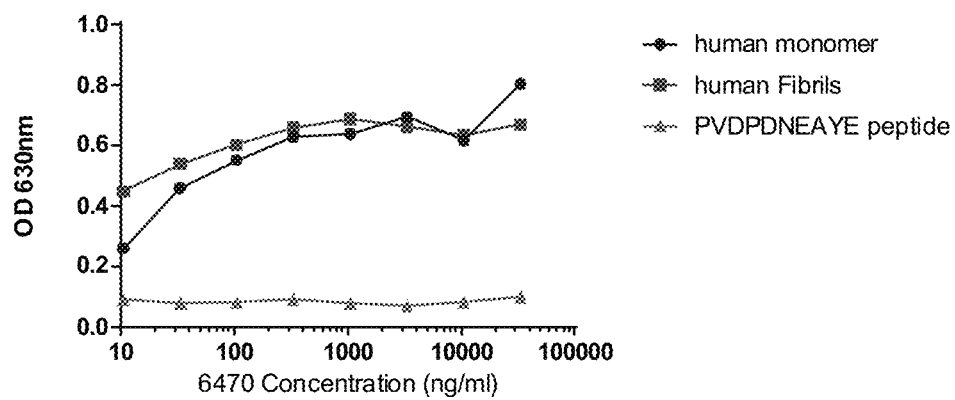
FIG. 3. ELISA binding assay. ELISA binding of FIG. 3A mouse 5811 Fab10HIS to recombinant human alpha synuclein monomer and fibrils and peptide PVDPDNEAYE (SEQ ID NO:42) of human alpha synuclein and FIG. 3B of mouse 5811 IgG1 to recombinant human alpha synuclein monomer and fibrils.
Figure 3B:
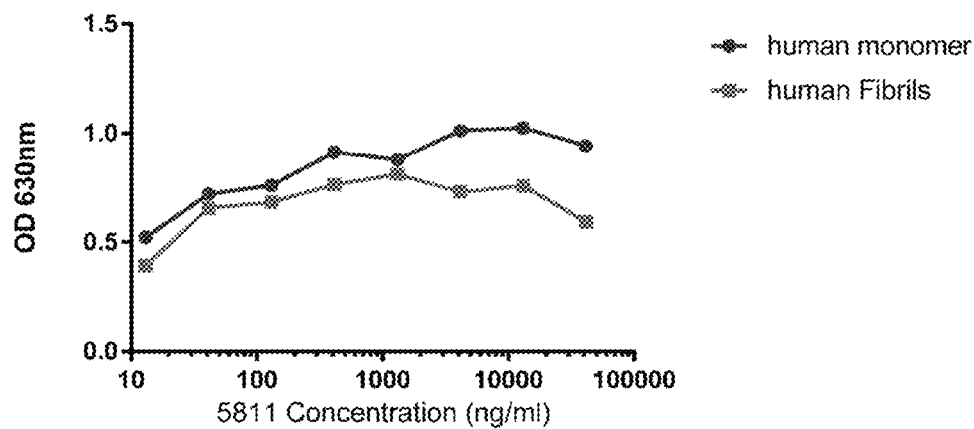

Purified rat-mouse chimeric antibodies were then subject to further screening by ELISA. Biotinylated recombinant human alpha synuclein monomer and fibrils were captured onto 384-well Maxisorp plates (ThermoScientific/Nunc) coated with streptavidin in carbonate coating buffer (dH$_2$O+ 0.16% Na$_2$CO$_3$+0.3% NaHCO$_3$). Separate plates were also coated with a biotinylated peptide corresponding to residues 117 to 126 of human alpha synuclein according to SEQ ID NO: 8 (peptide PVDPDNEAYE (SEQ ID NO:42)) to check if transients bound to this or a different region on the molecule. Plates were blocked with 1% w/v PEG/PBS and then incubated with several dilutions of purified transient supernatant. Secondary HRP-conjugated goat anti-mouse IgG Fc antibody (Stratech Scientific Ltd/Jackson ImmunoResearch) was added to plates, followed by visualization of binding with TMB substrate (3,3',5,5'-Tetramethylbenzidine, from EMD Millipore; 10 µl/well). The optical density was measured at 630 nM using BioTek Synergy 2 microplate reader. Data for antibody 5811, as IgG Fcγ1 (comprising SEQ ID NOs: 34 and 35) and as a Fab (comprising SEQ ID NOs: 34 and 36), is shown in FIGS. 3A and 3B. As can be seen, 5811 antibodies show binding to both monomeric and fibrillar recombinant human alpha synuclein, and also shows binding to the PVDPDNEAYE (SEQ ID NO:42) peptide.

Further characterization was carried out to determine the activity, affinity and avidity, epitope binding and biophysical properties of such antibodies. Unless explicitly mentioned that a humanized version was used, the experiments were carried out with the rat-mouse chimeric antibodies (5811 mFab or 5811 mIgG1).

Example 3: Antibodies Characterization

Biacore Kinetics

Interaction kinetics were determined by using surface plasmon resonance technology on a Biacore T200 instrument. Three different ligands including recombinant full-length human alpha synuclein monomer, purified recombinant human alpha synuclein fibrils, and purified recombinant mouse alpha synuclein fibrils, prepared as described herein, were each immobilized on three different flow cells of a CM5 chip surface using amine-coupling chemistry. The three ligands were prepared in 10 mM NaAc, pH 3.5, and immobilized onto separate flow cell surfaces to reach an immobilization level of about 30 response units (RU) for alpha synuclein monomer, about 40 RU for human alpha synuclein fibrils, and about 300 RU for mouse alpha synuclein fibrils respectively, at a flow rate of 10 µl/min. The buffer HBS-EP+ (GE healthcare Bio-Sciences AB) was used as running buffer for both ligand immobilization and kinetics assay. The binding of anti-alpha synuclein monoclonal 5811 mIgG1 antibody and monoclonal 5811 mFab antibody against the three ligands was then measured. The monoclonal mIgG1 or mFab antibodies were injected at 7 different concentrations from 800 nM to 0.195 nM over the 3 flow cells with a contact time of 3 mins and a disassociation time of 30 mins, at a flow rate of 100 µl/min. The surface was regenerated by one injection of 50 mM HCl for 90 s at 10 µl/min, and another injection of 50 mM HCl for 60 s at 10 µl/min. The data were analyzed using the Biacore T200 evaluation software (version 3.0) using the bivalent analyte model with assumed no bulk contribution (RI=0) and global Rmax for mIgG1 format, and 1:1 model with flexible bulk contribution (local RI) and global Rmax.

The kinetic values for both mIgG1 and mFab binding to the immobilized targets are shown in Table 2. The mIgG1 format showed apparent selective affinity toward human alpha synuclein fibrils comparing to the affinity to human alpha synuclein monomer, as disassociation constant KD is more than 10 times lower for human fibrils.

TABLE 2

| sample | human monomer | | | human fibril | | | mouse fibril | | |
|---|---|---|---|---|---|---|---|---|---|
| | ka1 (1/Ms) | kd1 (1/s) | KD1 (nM) | ka1 (1/Ms) | kd1 (1/s) | KD1 (nM) | ka1 (1/Ms) | kd1 (1/s) | KD1 (nM) |
| 5811 mFab | 1.26E+06 | 3.69E−04 | 0.29 | 1.04E+06 | 6.28E−04 | 0.60 | 3.12E+04 | 1.34E−03 | 42.92 |
| 5811 mIgG1 | 4.21E+05 | 2.25E−04 | 0.53 | 1.05E+06 | 2.87E−05 | 0.03 | 6.94E+05 | 8.27E−02 | 119.07 |

Binding to Beta Synuclein

Figure 4A:
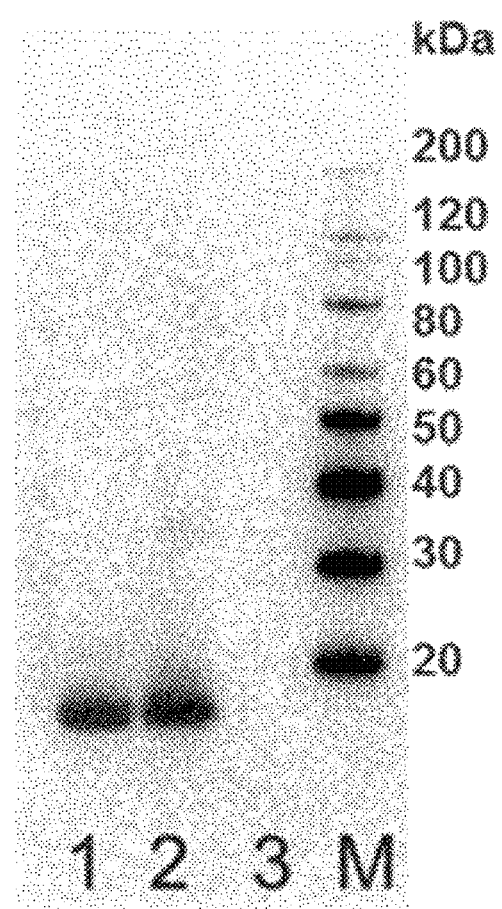
FIG. 4A Western blot showing binding of mouse 5811 IgG1 to human alpha-synuclein and human beta-synuclein. 1, Human alpha-synuclein; 2, Human alpha-synuclein (rPeptide); 3, Human beta-synuclein (rPeptide); Marker, MagicMark XP.

The binding of antibodies raised against human alpha synuclein to human beta synuclein were tested by Western blot using rPeptide beta synuclein. 1 micro gram of synuclein was run on a 4-12% Bis/Tris gel and blotted onto PVDF membrane. The membrane was blocked in PBS with 3% BSA and 0.1% Tween20. Antibody 5811 mIgG1 was added to the blocked blot and incubated for 1 hour at room temperature, washed with PBS, 0.1% Tween20 and incubated for 1 hour with a secondary antibody-HRP conjugate (anti rabbit H+L HRP conjugate, Bethyl, A120-101P). The blot was washed extensively in PBS with 0.1% Tween20, PBS and water. Chemi-luminescence was measured after addition of ECL Western blot substrate (Pierce). As shown in FIG. 4(A) lane 3, antibody 5811 mIgG1 does not bind to human beta-synuclein.

Epitope Mapping

NMR

Human alpha-synuclein was cloned into pET28a expression vector, such that the protein was expressed without any tags. The construct was transformed into $E.$ $coli$ BL21(DE3) cells (Stratagene), and cells were grown in defined medium with $C^{13}$ labelled DL-glucose and $N^{15}$ labelled ammonium sulphate in the presence and absence of deuterium oxide ($D_2O$). Expression was induced at OD600 nm=1 with 300 mM IPTG and the culture incubated at 30° C. for 4 hours. Cells were pelleted and lysed by three freeze-thaw cycles in 100 ml lysis buffer (20 mM Tris/HCl pH 8.0, 25 units benzonase (Merck Millipore), complete EDTA free protease inhibitor cocktail (2 tablets, Roche) and 10 mg lysozyme (Sigma)). The lysate was clarified by centrifugation at 18 000 rpm, and the cleared lysate passed through a 0.22 μm filter (Stericup, Millipore). The sterile lysate was loaded onto a MonoQ 10/100GL (GE Healthcare) equilibrated with 20 mM Tris/HCl pH 8.0, 5CV and protein was eluted with a gradient to 500 mM NaCl in the same buffer. Further purification of the purest fractions was repeated on the MonoQ 10/100GL column, following a 5-fold dilution in 20 mM Tris/HCl pH 8.0. The purest fractions were pooled, concentrated with a 10 kDa MWCO centrifugal concentrator (Centriprep, Millipore), purified by size exclusion on a HiLoad 26/600 Superdex 75 column (GE Healthcare), and eluted in 25 mM sodium phosphate buffer, 100 mM NaCl (pH 6.4). Fractions from the Superdex 75 column were pooled and Sodium azide (0.02% final concentration) and AEBSF (10 μM final concentration) were added. The final protein concentration was approximately 5 mg/ml.

Rat-mouse 5811 Fab antibody were expressed in CHO SXE as His tagged entities and purified from the supernatant by His-tag affinity chromatography, binding the protein to HisTrap Excel (GE Healthcare) from supernatant and eluting it with 250 mM imidazole in PBS. The elution pool was loaded onto HiTrap GammaBind Plus Sepharose (GE Healthcare), the column washed with PBS and protein eluted with 0.1M Glycine-HCl pH 2.6, and pH was adjusted to pH 6 with 0.75M Sodium Phosphate pH 9. Eluted Fab-His protein was buffer exchanged into NMR buffer (25 mM Sodium Phosphate pH 6.4, 100 mM NaCl) on a HiPrep 26/10 desalting column. Fab-His protein fractions were concentrated and protease inhibitors AEBSF (10 μM final concentration) and Sodium azide (0.02% final concentration) were added before filter sterilization over a Millex GV 0.22 μm filter.

Epitope binding of antibody 5811 having a VL of SEQ ID No.: 9 and a VH of SEQ ID No.: 10 was determined using heteronuclear magnetic resonance (NMR) spectroscopy using a Fab fragment of the antibody.

Backbone Assignment of α-Synuclein

NMR samples were typically 350 μl in volume with a protein concentration of 360 μM $^{13}C/^{15}N$ labelled or 430 μM $^2H/^{13}C/^{15}N$ labelled human alpha synuclein in 5 mm Shigemi tubes. Buffer conditions were 100 mM NaCl, 25 mM Sodium Phosphate pH 6.4, 10 μM AEBSF, 0.02% $NaN_3$. All experiments were recorded at 20° C. on either a 600 MHz Bruker AVIII or a 800 MHz Bruker AVII spectrometer fitted with cryogenically cooled probes. Sequential connections between backbone NMR signals of residues in the protein, $H_N(i)$-N(i)-N(i±1), were made using a 3D (H)N (CA)NNH experiment (Weisemann et al., 1993 3D Triple-resonance NMR techniques for the sequential assignment of NH and 15N resonances in 15N- and 13O-labelled proteins. J. Biomol. NMR 3) recorded with spectral widths of 28, 28 and 10 ppm and acquisition times of 117 (F1), 117 (F2) and 140 (F3) ms in the $^{15}N$, $^{15}N$ and $^1H$ dimensions, respectively, with 8 scans per increment and a 1.5 s relaxation delay. Non-uniform sampling was employed with a sampling density of 10% (4000 out of 40000 hyper-complex points) giving a total acquisition time of 2.75 days. Sequential connections were confirmed and residue types identified using TROSY-HNCA (Grzesiek and Bax, 1992 Improved 3D triple-resonance NMR techniques applied to a 31 kDa protein. J. Magn. Reson. 96, 432-440; Salzmann et. al., 1998. TROSY in triple-resonance experiments: new perspectives for sequential NMR assignment of large proteins. Proc. Natl. Acad. Sci. USA. 95, 13585-90) and TROSY-HNCACB (Wittekind and Mueller, 1993 HNCACB, a High-Sensitivity 3D NMR Experiment to Correlate Amide-Proton and Nitrogen Resonances with the Alpha- and Beta-Carbon Resonances in Proteins. J. Magn. Reson. Ser. B 101, 201-205; Salzmann et. al., 1999. TROSY-type Triple Resonance Experiments for Sequential NMR Assignment of Large Proteins. J. Am. Chem. Soc. 121, 844-848) experiments. The TROSY-HNCA experiment was recorded with spectral widths of 23, 28, 10 ppm and acquisition times of 12.1 (F1), 21.7 (F2) and 100 (F3) ms in the $^{13}C$, $^{15}N$ and $^1H$ dimensions respectively (8 scans per increment, 1.5 s relaxation delay, 1 day total acquisition time) whilst the TROSY-HNCACB was recorded with spectral widths of 56, 28 and 10 ppm and acquisition times of 8.2 (F1), 21.7 (F2) and 100 (F3) ms in the $^{13}C$, $^{15}N$ and $^1H$ dimensions respectively (8 scans per increment, 1.5 s relaxation delay, 1.7 days total acquisition time). Backbone carbonyl assignments were obtained from a TROSY-HNCO spectrum (Grzesiek and Bax, 1992 Improved 3D triple-resonance NMR techniques applied to a 31 kDa protein. J. Magn. Reson. 96, 432-440; Salzmann et. al., 1998. TROSY in triple-resonance experiments: new perspectives for sequential NMR assignment of large proteins. Proc. Natl. Acad. Sci. USA. 95, 13585-90) recorded with spectral widths of 10, 29, 10 ppm and acquisition times of 80 (F1), 21.7 (F2) and 150 (F3) ms in the $^{13}C$, $^{15}N$ and $^1H$ dimensions respectively (8 scans per increment and a 1.5 s relaxation delay). Non-uniform sampling was employed with a sampling density of 15% (1208 out of 8050 hyper-complex points) giving a total acquisition time of 19 hours. NMR spectra were processed using NMRPipe (Delaglio et al., 1995 NMRPipe: a multidimensional spectral processing system based on UNIX pipes. J. Biomol. NMR 6, 277-93), with linear prediction used to extend the effective acquisition time in nitrogen by up to 1-fold. The non-uniform sampled data was reconstructed using the Harvard iterative soft thresholding method (Hyberts et al., 2012 Application of iterative soft thresholding for fast reconstruction of NMR data non-uniformly sampled with multidimensional Poisson Gap scheduling. J Biomol NMR 52, 315-27), with the data reconstructed to the next Fourier number, increasing the indirect acquisition times by up to 60%. Data analysis was carried out using Sparky (Goddard and Kneller, D. G. SPARKY 3. In., University of California, San Francisco), resulting in the assignment of the amide proton and nitrogen resonances of 133 residues, corresponding to 99% of residues excluding Proline residues and the N-terminal Methionine. The only other residue of alpha synuclein that was not assigned was the Aspartic acid at position 2.

Mapping the Binding Site of Antibody 5811Fab Fragment

Mapping of the binding site of 5811 was carried out using a 150 μM sample of $^2H/^{13}C/^{15}N$ labelled human α-Synuclein containing a 10% molar excess of the unlabelled 5811 Fab. Samples were prepared in the same buffer as described above for the backbone assignment of the α-Synuclein. $^1H$, $^{15}N$ and $^{13}C$ chemical shift changes were determined by comparison of the TROSY-HNCO (Grzesiek and Bax, 1992 Improved 3D triple-resonance NMR techniques applied to a 31 kDa protein. J. Magn. Reson. 96, 432-440; Salzmann et. al., 1998. TROSY in triple-resonance experiments: new perspectives for sequential NMR assignment of large proteins. Proc. Natl. Acad. Sci. USA. 95, 13585-90) spectrum recorded on the alpha synuclein/Fab complex with an equivalent control spectrum recorded on the free alpha synuclein. The control TROSY-HNCO experiment of the free alpha synuclein was recorded with spectral widths of 10, 28 and 10 ppm and acquisition times of 80 (F1), 21.7 (F2) and 150 (F3) ms in the $^{13}C$, $^{15}N$, and $^1H$ dimensions respectively (16 scans per increment, 1.4 s relaxation delay). Non-uniform sampling (NUS) was employed with a sampling density of 25% (2013 out of 8050 hyper-complex points) giving a total acquisition time of 2.5 days. The TROSY-HNCO experiment of the α-Synuclein/Fab complex was recorded with spectral widths of 10, 28 and 10 ppm and acquisition times of 80 (F1), 21.7 (F2) and 80 (F3) ms in the $^{13}C$, $^{15}N$, and $^1H$ dimensions respectively (32 scans per increment, 1.5 s relaxation delay). Non-uniform sampling was employed with a sampling density of 25% (1119 out of 4477 hyper-complex points) giving a total acquisition time of 2.8 days. NMR spectra were processed using NMRPipe (Delaglio et al., 1995 NMRPipe: a multidimensional spectral processing system based on UNIX pipes. J. Biomol. NMR 6, 277-93) with reconstruction of the NUS data performed using mddnmr (Orekhov and Jaravine, 2011. Analysis of non-uniformly sampled spectra with Multi-Dimensional Decomposition. Prog. Nucl. Magn. Reson. Spectrosc., 59, p 271-292). The effective acquisition time of the nitrogen dimension was increased by up to 1-fold during the data reconstruction.

Chemical shift changes were analysed using the minimal shift approach (Williamson et al., 1997 Mapping the binding site for matrix metalloproteinase on the N-terminal domain of the tissue inhibitor of metalloproteinases-2 by NMR chemical shift perturbation. Biochemistry 36, 13882-9), essentially as described previously (Veverka et al., 2008 Structural characterization of the interaction of mTOR with phosphatidic acid and a novel class of inhibitor: compelling evidence for a central role of the FRB domain in small molecule-mediated regulation of mTOR. Oncogene 27, 585-95), with the exception of a modification to the equation used to calculate the combined chemical shift change (Δδ) to include the carbonyl chemical shift, resulting in the following equation:

$$\Delta\delta = \frac{\sqrt{(\Delta\delta HN)^2 + (\Delta\delta N\alpha N)^2 + (\Delta\delta C\alpha C)^2}}{3}$$

where $\Delta\delta_{HN}$, $\Delta\delta_N$ and $\Delta\delta_C$ are the differences in the $^1H$, $^{15}N$ and $^{13}C$ chemical shifts respectively. αN and αC correspond to scaling factors of 0.2 and 0.35, respectively, used to account for differences in the chemical shift ranges of the amide proton, nitrogen and carbonyl chemical shifts.

To identify the Fab binding sites (epitopes) on alpha synuclein, a histogram of combined minimal shift versus protein sequence was used to reveal regions of alpha synuclein containing significantly perturbed signals. If the size of the combined chemical shift change for individual amino acids exceeded a threshold value of the mean of the combined chemical shift change for all the amino acids plus one standard deviation from that mean, these residues were selected for further evaluation as possible contact residues in the Fab binding site.

Significantly perturbed residues were identified as those whose minimal shift was at least greater than the mean plus one standard deviation of all calculated shifts. Four different thresholds were applied to identify residues bound by the Fab. Residues that are involved in the binding site are scored with increasing stringency as: those whose minimal shift exceeds mean plus one standard deviations of all calculated shifts (being >0.025574); those whose minimal shift exceeds mean plus two standard deviations of all calculated shifts (being >0.042552); those whose minimal shift exceeds mean plus three standard deviations of all calculated shifts (being >0.059530); those whose minimal shift exceeds mean plus four standard deviations of all calculated shifts (being >0.076508). In this analysis Proline residues cannot be identified as they contain no amide proton.

The alpha synuclein epitope for 5811 Fab is therefore defined with increasing stringency as mean plus one standard deviation of all calculated shifts: E114, D115, V118, D119, D121, N122, E123, A124, Y125, E126, M127, S129, Q134, D135 and Y136; mean plus two standard deviation of all calculated shifts: V118, D119, D121, N122, Y125, M127, D135 and Y136; mean plus three standard deviation of all calculated shifts: V118, D119, D121, N122, M127, D135 and Y136; no residues were shifted by over the mean plus four standard deviation of all calculated shifts.

Using the amino acid numbering used in NCBI Reference Sequence NP_000336.1, 5811 Fab was found to bind at least the following alpha synuclein residues (mean+3 SD) V118, D119, D121, N122, Y125, M127, D135 and Y136. The antibody may also bind all the following residues (mean+1 SD) E114, D115, V118, D119, D121, N122, E123, A124, Y125, E126, M127, S129, Q134, D135 and Y136.

Figure 4B:
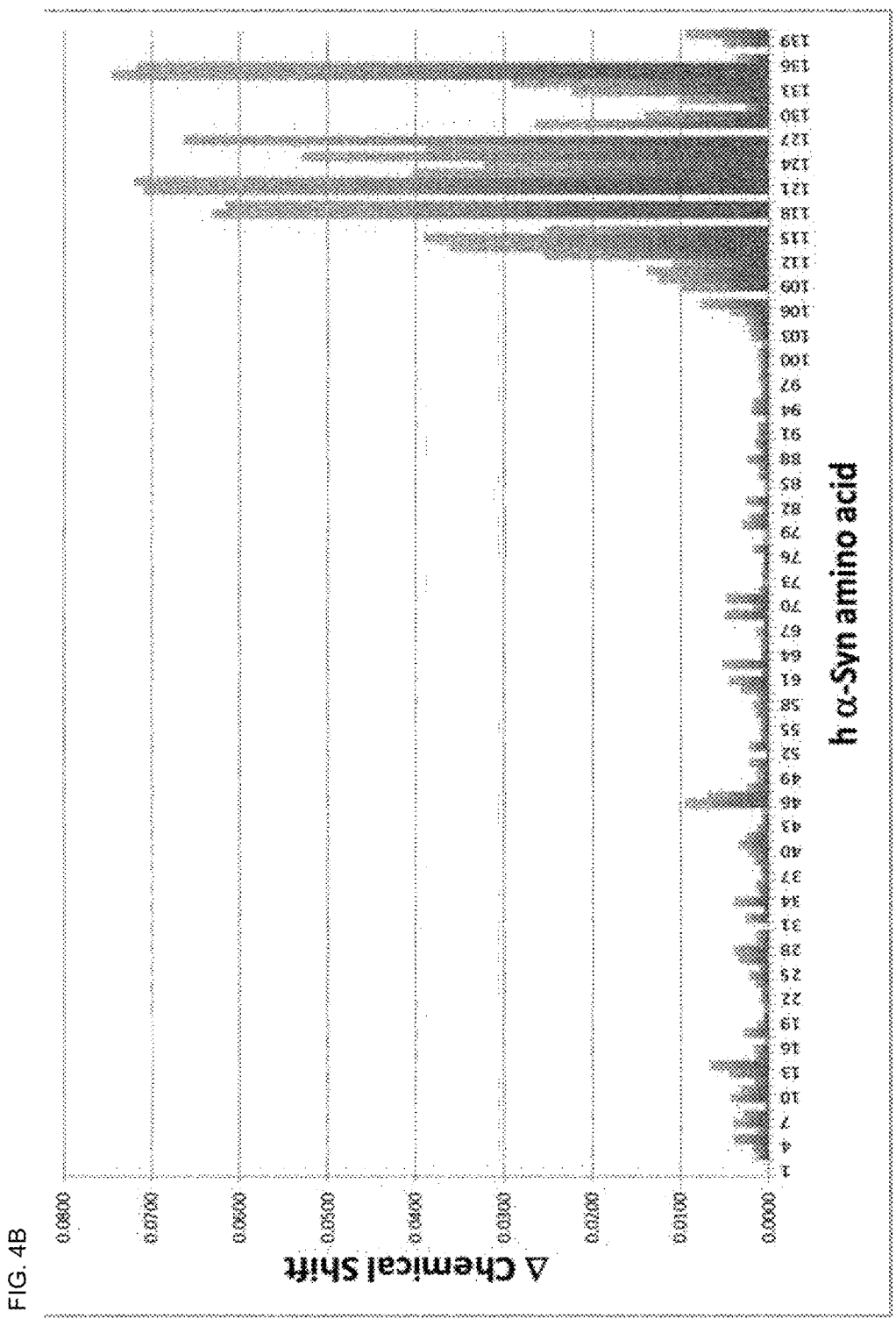
FIG. 4B NMR chemical shift changes showing the predicted epitope of mouse 5811 Fab on human alpha synuclein.

As shown in FIG. 4B, the NMR chemical shift changed on dCN human alpha synuclein upon binding with 5811 mFab. The predicted epitope of 5811 mFab appears to comprise residues within amino acids 114 and 136 of human alpha-synuclein (SEQ ID NO: 8)

Peptide Mapping

Further characterization of the epitope bound by antibody 5811 mFab was performed by using short (typically 9-mer or 10-mer) peptides representative of and covering the C-terminal region of human alpha synuclein. These were used in a competitive surface plasmon resonance assay to test whether any were capable of inhibiting binding of the antibody to either monomeric alpha synuclein or pre-formed alpha synuclein fibrils immobilized on a Biacore chip. A peptide showing the maximum level of inhibition was then selected for co-crystallization studies with the antibody in order to confirm the exact epitope.

Peptides were supplied by Peptide Protein Research Ltd., Bishop's Waltham, U.K., and were synthesized by Fmoc solid phase peptide chemistry according to the method of Atherton and Sheppard. (Ref: Atherton, E.; Sheppard, R. C. (1989). Solid Phase peptide synthesis: a practical approach. Oxford, England: IRL Press). N and C peptide termini were capped with acetyl and amide groups respectively except in the case of the peptides representing the N-terminus and C-terminus of α-synuclein where the amino and carboxyl groups respectively remained free. Peptide stock solutions were prepared in DMSO at 10 mM. The full list of peptides is shown in Table 3.

TABLE 3

| Peptide ID | Sequence | SEQ ID NO: |
|---|---|---|
| AS104-113 | EEGAPQEGIL | 37 |
| AS109-118 | QEGILEDMPV | 38 |
| AS111-120 | GILEDMPVDP | 39 |
| AS113-122 | LEDMPVDPDN | 40 |
| AS115-124 | DMPVDPDNEA | 41 |
| AS117-126 | PVDPDNEAYE | 42 |
| AS119-128 | DPDNEAYEMP | 43 |
| AS121-130 | DNEAYEMPSE | 44 |
| AS123-132 | EAYEMPSEEG | 45 |
| AS125-134 | YEMPSEEGYQ | 46 |
| AS127-136 | MPSEEGYQDY | 47 |

Recombinant human alpha synuclein monomer and preformed alpha synuclein fibrils were immobilized on a CM5 chip using a Biacore 3000 instrument (GE Healthcare). Following activation of the carboxymethyl dextran surface by injection of 100 µl of a fresh 1:1 (v/v) mixture of 50 mM N-hydroxysuccimide and 200 mM 1-ethyl-3-(3-dimethyl-aminopropyl)-carbodiimide at a flow rate of 10 µl/min HBS-EP (GE Healthcare) as running buffer, coupling was achieved by injecting 100 µl of monomer and fibrils, at 5 µM in 10 mM acetate pH 5.0, over separate flow cells. A reference flow cell was activated in the same manner and then all flow cell surfaces were deactivated with a 50 µl pulse of 1 M ethanolamine.HCl pH 8.5.

Peptide solutions were prepared in running buffer at 100 µM and a peptide blank control prepared as a 1 in 100 dilution of DMSO in running buffer. A solution of 5811 mFab was prepared at 50.5 nM in running buffer prior to pre-incubating 198 µl with 2 µl of either blank control or diluted peptide to yield a final mixture of 50 nM Fab and 1 µM peptide or control. Sensograms were recorded for each sample by injecting 30 µl of the mixture at 10 µl/min and recording a report point 5 seconds before the end of the injection. The chip was regenerated at the end of each cycle by two 10 µl injections of 40 mM HCl and one injection of 5 mM NaOH. Control cycles were alternated with peptide cycles.

The degree of inhibition of each peptide were calculated as the percentage change in response units measured at the report point compared to that of the mean of adjacent control cycles.

Figure 5:
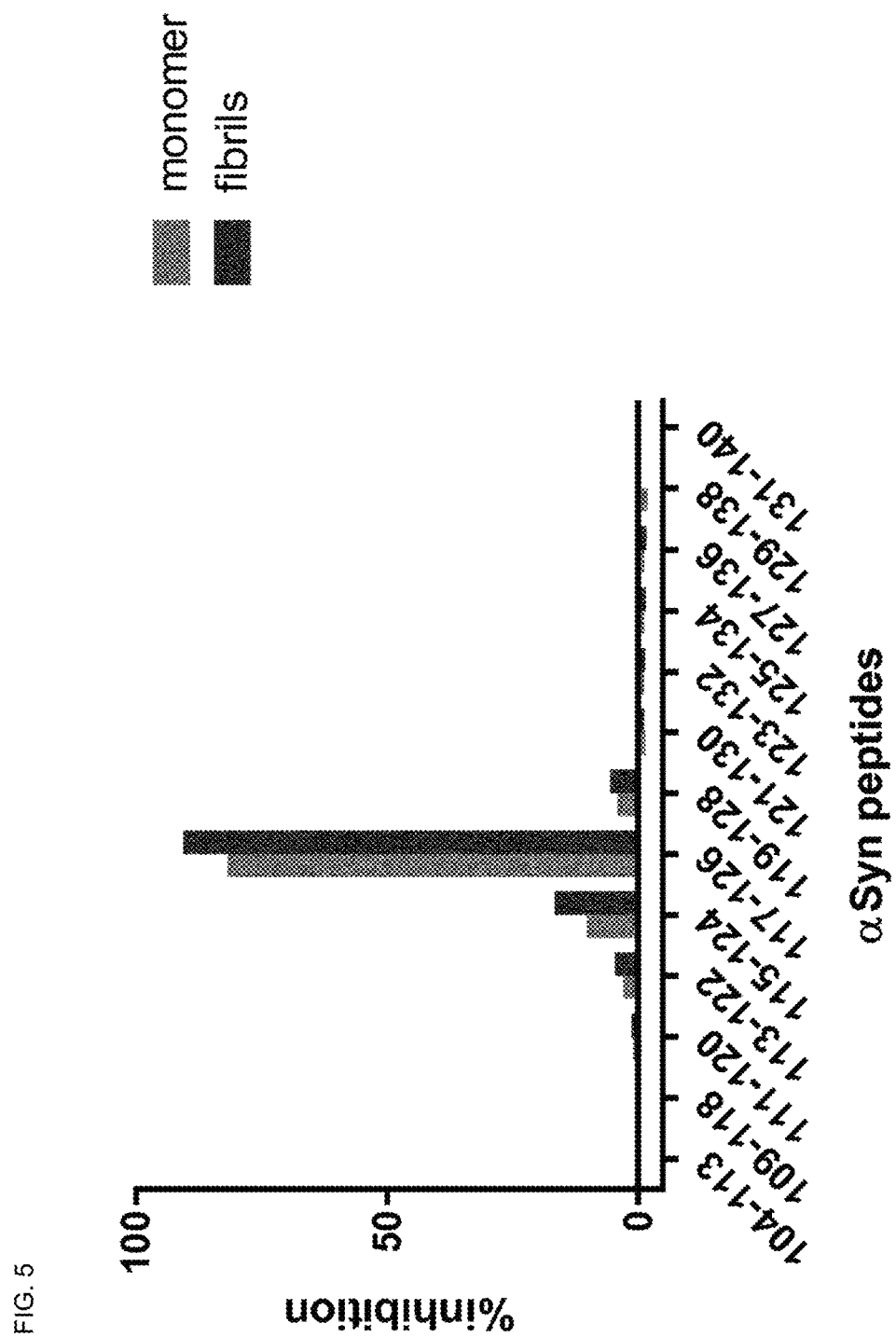
FIG. 5. Inhibition of binding of 5811 Fab to immobilized alpha synuclein (bars at the left, monomer and right fibrils, respectively, for each of the peptides tested).

The level of inhibition of each alpha synuclein peptide is shown in FIG. 5. Significant inhibition of 5811 mFab to either alpha synuclein monomer or fibrils was only observed for the C-terminal peptides AS113-122, AS115-124, AS117-126 and AS119-128, where the levels of inhibition to either form of α-synuclein were very similar. The strongest level of inhibition was observed for peptide AS117-126 at 81% and 90% for binding to monomer and fibril, respectively. Residues in common across the above the four peptides are 119 to 122 that thus comprise part of the epitope. Since the level of inhibition falls to between only 2 to 5% for peptides AS113-122 and AS119-128, residues 115 to 118 and 123 to 124 must also comprise part of the epitope.

The result of this study suggested that the epitope of antibody 5811 comprises residues 115 to 124 (DMPVDPD-NEA (SEQ ID NO:41)).

Alanine Scanning

Single amino acid mutants of human alpha synuclein (His-tagged) were prepared and expressed in the Expi293 System (Thermo Fisher Scientific) according to the manufacturer instruction. Alanine residues were placed at positions 118 to 128, with the exception of residue 124 which is already an alanine and which was changed to a serine (Table 4). The mutant proteins were purified from supernatants obtained after centrifugation (4200 rpm, 2 hours) followed by sterile filtration (Stericup, Millipore). The supernatants were loaded onto a HisTrap Excel column (GE Healthcare) pre-equilibrated and washed with 25 mM Sodium phosphate and 500 mM NaCl. Bound protein was eluted with a gradient of imidazole up to 500 mM in the same buffer. Fractions with protein of interest were identified by NuPage gel electrophoresis, pooled, concentrated using a Centriprep 10 kDa MWCO (Millipore) and buffer exchanged on a PD-10 column into PBS. Protein fractions were concentrated using an Ultracel 3 KDa MWCO centrifugal spin concentrator (Millipore). The concentrate was pass through a 0.22 mM sterilization filter (Millex GV, Millipore) and stored at −20° C. All mutants were expressed in similar amount to wild type human alpha synuclein (FIG. 6A).

TABLE 4

| Mutant alpha-synuclein |
|---|
| V118A |
| D119A |
| P120A |
| D121A |
| N122A |
| E123A |
| A124S |
| Y125A |
| E126A |
| M127A |
| P128A |

The mutants of human alpha synuclein were analyzed on a 4-12% Bis/Tris NuPage gel using 1 microgram per protein per lane and blotted onto PVDF membrane (iBlot mini stack, Thermo Fisher Scientific). The blot was blocked in block buffer (3% bovine serum albumin, 0.1% Tween20 in Phosphate Buffered Saline, PBS) and was incubated with either antibody 5811 mFab or antibody 5811 mIgG1. The blot was washed after 1-hour incubation at room temperature with 0.1% Tween in PBS. The blot was incubated for 1 hour with secondary detection antibody anti-mouse IgG Fc HRP conjugate (AB5879, Abcam) in block buffer, washed and chemo-luminescence detected after addition of ECL Western Blotting Substrate (Pierce).

As shown in FIGS. 6B and 6C, 3 mutants corresponding to human alpha synuclein D119A, N122A and Y125A were not recognized by antibodies 5811 mFab and 5811 mIgG1. This analysis suggests that these amino acids in human alpha-synuclein may be essential for the binding of antibodies 5811 mFab and 5811 mIgG1 to human alpha synuclein.

Example 4: Antibody Humanization

Figure 8:
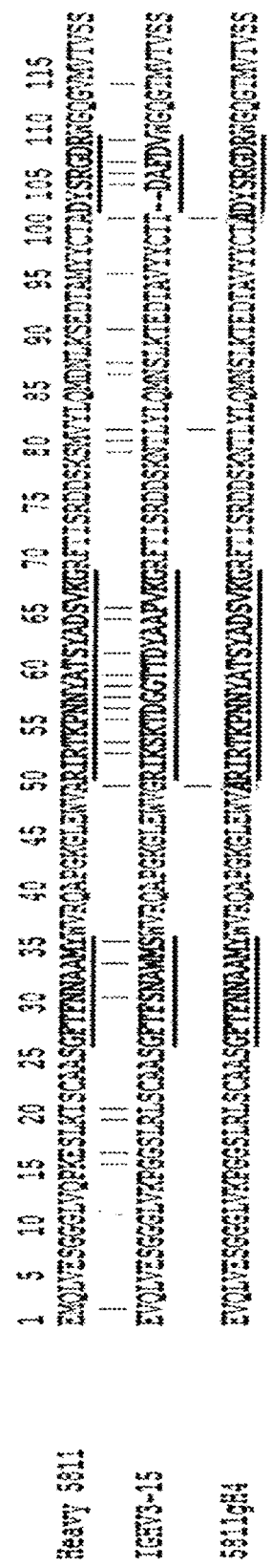
FIG. 8. Heavy Chain Humanization. 5811 is for rat variable heavy chain sequence. 5811gH4 is for the humanized graft of antibody 5811 variable heavy chain using IGHV3-15 human germline as the acceptor framework. CDRs are shown in bold/underlined. Donor residues are shown in bold/italic and are shaded: A49 and A100. Figure discloses SEQ ID NOS 10, 30, and 25, respectively, in order of appearance.

Rat antibody 5811 was humanized by grafting the CDRs from the rat V-region onto human germline antibody V-region frameworks. In order to recover the activity of the antibody, a number of framework residues from the rat V-region were also retained in the humanized sequence. These residues were selected using the protocol outlined by Adair et al. (WO91/09967). Alignments of the rat antibody (donor) V-region sequences with the human germline (acceptor) V-region sequences are shown in FIGS. 7 and 8, together with the designed humanized sequences. The CDRs grafted from the donor to the acceptor sequence are as defined by Kabat (Kabat et al., 1987), with the exception of CDR-H1 where the combined Chothia/Kabat definition is used (see Adair et al., 1991 Humanized antibodies. WO91/09967).

Genes encoding a number of variant heavy and light chain V-region sequences were designed and constructed by an automated synthesis approach by DNA2.0 Inc. Further variants of heavy and light chain V-regions were created by modifying the VH and VK genes by oligonucleotide-directed mutagenesis, including, in some cases, mutations within CDRs. For transient expression in mammalian cells, the humanized light chain V-region genes were cloned into the UCB light chain expression vector pMhCK, which contains DNA encoding the human Kappa chain constant region (Km3 allotype). The humanized heavy chain V-region genes were cloned into the UCB human gamma-4 heavy chain expression vector pMhγ4PFL, which contains DNA encoding the human gamma-4 heavy chain constant region with the hinge stabilizing mutation S241P (Angal et al., Mol. Immunol. 1993, 30 (1):105-8). Chimeric rat-human 5811 antibody (comprising SEQ ID NOs: 9 and 10) was also similarly prepared. Co-transfection of the resulting heavy and light chain vectors into Expi293™ suspension cells was achieved using ExpiFectamine™ 293 transfection reagent (A14525, ThermoFisher Scientific), and gave expression of the humanized, recombinant antibodies in either the human IgG4P or Fab-HIS formats.

Human V-region IGKV1-39 plus JK1 J-region (IMGT, http://www.imgt.org/) was chosen as the acceptor for antibody 5811 light chain CDRs. The light chain framework residues in grafts gL5, gL8 and gL14 are all from the human germline gene, with the exception of residue 71 (with reference to SEQ ID No: 13), where the donor residue Tyrosine (Y71) was retained. Residue 94 in CDRL3 of graft gL14 was mutated from a Glycine (G) to an Alanine (A) residue, thus modifying a potential Asparagine deamidation site.

Human V-region IGHV3-15 plus JH3 J-region (IMGT, http://www.imgt.org/) was chosen as the acceptor for the heavy chain CDRs of antibody 5811. The heavy chain framework residues in graft gH4 are all from the human germline gene, with the exception of residues 49 and 100 (with reference to SEQ ID No: 25), where the donor residues Alanine (A49) and Alanine (A100) were retained, respectively.

The variant humanized antibody chains, and combinations thereof, were expressed and assessed for their potency relative to the parent antibody, their biophysical properties and suitability for downstream processing.

As shown in Table 5, all grafts retained the same or similar affinity as the parental rat-human antibody to alpha synuclein in fibrils.

TABLE 5

| Antibody 5811 variant | Light Chain Donor Residues | Heavy Chain Donor Residues | ka1 (1/Ms) | kd1 (1/s) | Affinity (KD) pM |
|---|---|---|---|---|---|
| Chimeric rat-human 5811 | — | — | 1.56E+06 | 2.42E−05 | 15.6 |
| 5811gL5gH4 | Y71 | A49, A94 | 2.74E+06 | 4.10E−05 | 15.0 |
| 5811gL8gH4 | — | A49, A94 | 3.26E+06 | 5.17E−05 | 15.9 |
| 5811gL14gH4 | A100 | A49, A94 | 1.10E+06 | 2.04E−05 | 18.5 |

Example 5: Immunohistochemistry

Figure 9:
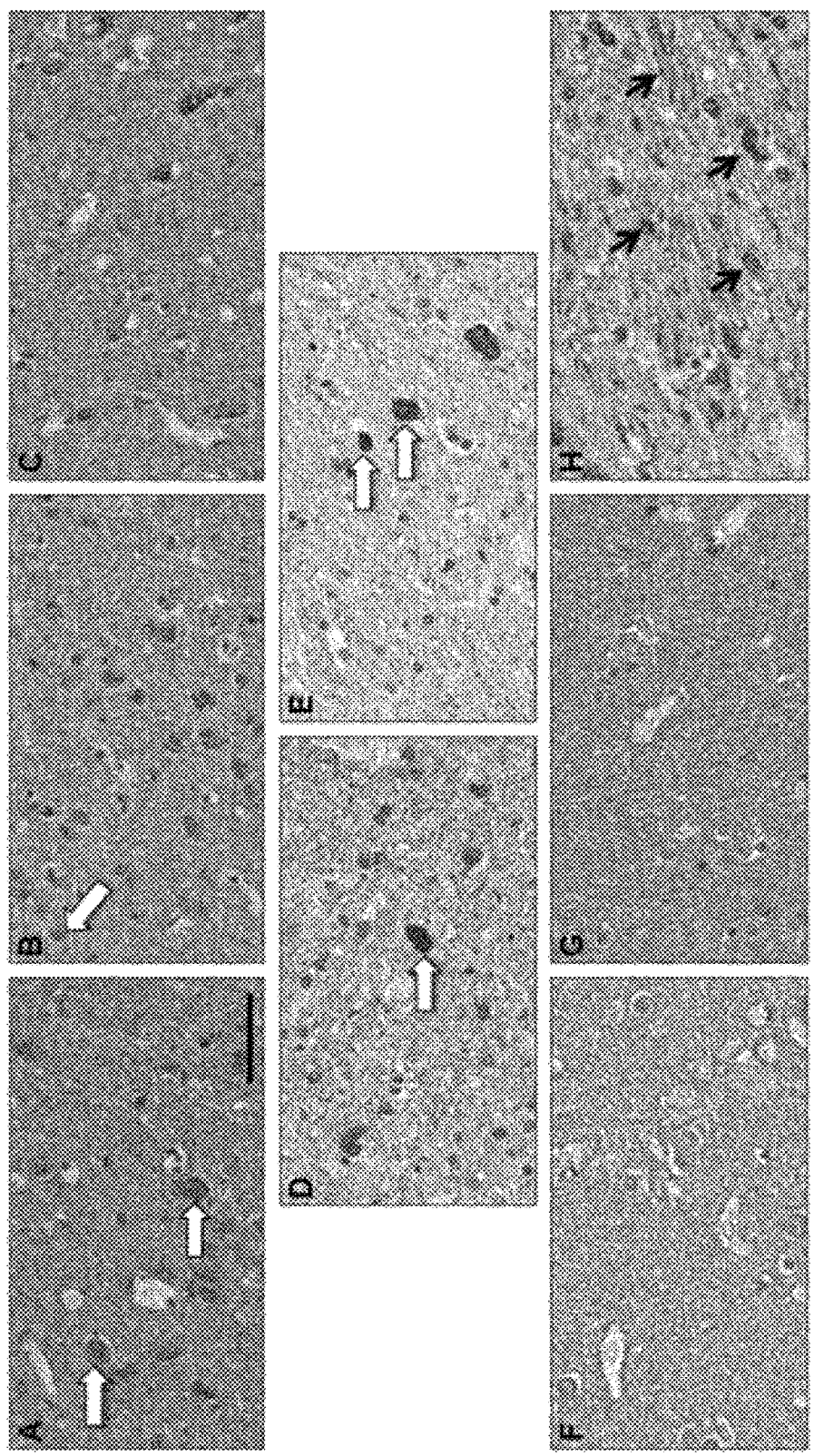
FIG. 9. Immunohistochemistry. Immunoreactivity in brain sections from (A-E) PD and (F-H) non-PD patients. (A-C) In the temporal cortex of PD patients, antibody 5811 mIgG1 labelled the neuropil and the cytoplasm of some cells; occasional Lewy Body-like structures were observed (white arrows). (D, E) antibody 5811 mIgG1 labelled Lewy body-like features (white arrows) in the substantia nigra of PD patients. (F, G) In the non-PD temporal cortical tissues, antibody 5811 mIgG1 labelled the neuropil as well, but no Lewy body-like structures were observed. (H) No Lewy body-like structures were observed in the substantia nigra of a non-PD individual; black arrows point to non-specific labelling corresponding to neuromelanin-containing neurons and neuronal fibers. Scale bar=50 µm.

Immunohistochemistry was performed by Asterand Bioscience (Royston, United Kingdoms). Cryosections (10 μm) were first submitted to antigen retrieval procedure using Dako PT Link and EnVision FLEX Target Retrieval Solutions (pH 6) at 97° C. for 20 min with automatic heating and cooling. All following incubation steps were carried out at room temperature. Cryosections were air dried for 30 minutes, fixed in 4% paraformaldehyde prepared in 1×PBS for 10 minutes, washed in Dako EnVision™ FLEX Wash Buffer (Dako) and then loaded into a Dako Autostainer Plus. Endogenous peroxidase activity was blocked by incubating the sections with Dako peroxidase block (Dako) for 5 minutes. The sections were then washed twice with 1×PBS before incubating with Dako CSA II protein block (Dako) for 10 minutes. The protein block solution was removed by air jet and the sections incubated for 30 minutes with 5811 rat-mouse IgG1 antibody (comprising SEQ ID NOs: 34 and 35) diluted (0.05 μg/ml) in Dako antibody diluent (Dako). Following incubation, the sections were washed twice with 1×PBS, then incubated with anti-mouse Dako Flex polymer-HRP substrate (Dako) for 20 minutes, washed twice and then incubated with diaminobenzidine substrate (Dako) for 10 minutes. The chromogenic reaction was stopped by rinsing the slides with distilled water. Following chromogenesis, the sections were removed from the Dako Autostainer Plus and manually counterstained with haematoxylin, dehydrated in an ascending series of ethanol, cleared in three changes of xylene and cover slipped under DPX mounting medium (Sigma-Aldrich). Digital images of stained sections were obtained using an Aperio ScanScope AT Turbo system (Leica Biosystems). Antibody 5811 mIgG1 was tested on brain sections derived from five different pS129-alpha synuclein-positive and three different pS129-alpha synuclein-negative donors (1 section/donor). Antibody 5811 mIgG1 labeled the neuropil and occasional Lewy body-like features in the temporal cortex and substantia nigra of PD patients (FIG. 9A-E). In the non-PD brain tissues, antibody 5811 mIgG1 labeled the neuropil in the temporal cortex, but no Lewy body-like structures were observed in the cortex or substantia nigra (FIG. 9F-H). These observations suggest that antibody 5811 mIgG1 binds to normal alpha synuclein in the neuropil of brain tissues from PD and non-PD patients, while it binds to pathological α-synuclein present in Lewy bodies in PD-patients only.

Example 6: Characterization of Humanized Antibodies

Three Ab5811 humanized IgG4P antibodies (5811gL5gH4; 5811gL8gH4 5811gL14gH4; sequences in Table 1) were tested to assess their biochemical and biophysical characteristics, including thermal stability ($T_m$), experimental pI, hydrophobicity, solubility (PEG precipitation assay), aggregation stability at an air/liquid interface and chemical stability with respect to the deamidation propensity of Asn93 on CDR-L3 (5811gL14gH4 has N(93)A motif and both 5811gL8gH4 and gL5gH4 have N(93)G motif).

Thermal Stability ($T_m$) Measurements

The melting temperature (Tm) or temperature at the midpoint of unfolding, was determined using the Thermofluor assay. In this method, the fluorescent dye SYPRO orange was used to monitor the protein unfolding process by binding to hydrophobic regions that become exposed as the temperature increases.

The reaction mix contained 5 μl of 30×SYPRO® Orange dye (Invitrogen™), diluted with PBS from 5000× stock solution and 45 μl of sample at 0.12 mg/ml, (in PBS pH 7.4). About 10 μl of the mix was dispensed in quadruplicate into a 384 PCR optical well plate and was run on a 7900HT Fast Real-Time PCR System (Applied Biosystems™). The PCR system heating device was set at 20° C. to 99° C. with an increase rate of 1.1° C./min. A charge-coupled device monitored fluorescence changes in the wells. Intensity increases were plotted, and the inflection point of the slope(s) was used to calculate the T, as described below. The T, for each antibody molecule was obtained in both PBS pH 7.4 and 50 mM sodium acetate/125 mM sodium chloride pH 5.0, being common pre-formulation buffers.

The thermal stability for all three humanized antibodies is shown in Table 6. One transition was observed in PBS pH 7.4 and this was attributed to both the $CH_2$ and Fab domain unfolding. In 50 mM sodium acetate/125 mM sodium chloride pH 5.0, two transitions were observed. The lower $T_m$ was attributed to the $CH_2$ unfolding domain and the second transition was attributed to the Fab domain. From this analysis, antibodies 5811gL8gH4 and 5811gL5gH4 have comparable thermal stability with antibody 5811gL14gH4 just slightly less thermally stable.

methylcellulose solution (Protein Simple), 4 μL pH 3-10 ampholytes (Pharmalyte), 0.5 μL of 4.65 and 0.5 μL 9.77 synthetic pI markers (ProteinSimple), 12.5 μL of 8M urea solution (Sigma-Aldrich®). HPLC grade water was used to make up the final volume to 100 μL. The mixture was vortexed briefly to ensure complete mixing and centrifuged at 10,000 rpm for 3 minutes to remove air bubbles before analysis. Samples were focused for 1 minute at 1.5 kV, followed by 5 minute at 3 kV, and A280 images of the capillary were taken using the ProteinSimple software. The resulting electropherograms were first analyzed using iCE3 software and pI values were assigned (linear relationship between the pI markers). The calibrated electropherograms were then integrated using Empower® software (Waters).

The experimental pI of all molecules was in the range of 8.80-9.23, with a main species at 9.09. There was no difference to the acidic/basic species distribution which was typical for IgG4P molecules. The experimental pIs were high and hence would aid in the manufacture process of the antibodies.

Hydrophobic Interaction Chromatography (HIC)

The humanized antibodies 5811gL14gH4, 5811gL8gH4 and 5811gL5gH4 were assessed for their hydrophobicity behaviors via Hydrophobic Interaction Chromatography (HIC). In HIC, the antibodies bind to the hydrophobic stationary phase in the presence of high concentrations of polar salts and desorb into the mobile phase as the concentration of salt decreases. A longer retention time equates to a greater hydrophobicity.

Antibody samples at 2 mg/mL were diluted 1:2 with 1.6 M ammonium sulphate and PBS (pH 7.4). 5 μg (10 μL) of sample was injected onto a Dionex ProPac™ HIC-10 column (100 mm×4.6 mm) connected in series to an Agilent 1200 binary HPLC with a fluorescence detector. The separation was monitored by intrinsic fluorescence (excitation and emission wavelengths, 280 nm and 340 nm respectively).

Using Buffer A (0.8 M ammonium sulphate 100 mM Phosphate pH7.4) and Buffer B (100 mM Phosphate pH7.4) the sample was analyzed using gradient elution as follows, (i) 2-minute hold at 0% B, (ii) linear gradient from 0 to 100% B in 30 minutes (0.8 mL/minute) (iii) the column was washed with 100% B for 2 minutes and re-equilibrated in 0% B for 10 minutes prior to next sample injection. The column temperature was maintained at 20° C. Standards exhibiting low and high hydrophobicity plus a control were also analyzed in the same run sequence to allow normaliza-

TABLE 6

| | Antibody | Mean $T_m$ (1) ° C. | Std. Error | Mean $T_m$ (2) ° C. | Std. Error |
|---|---|---|---|---|---|
| PBS pH 7.4 | 5811gL14gH4 | 65.3 | 0 | ND | ND |
| | 5811gL8gH4 | 67.6 | 0 | ND | ND |
| | 5811gL5gH4 | 67.6 | 0 | ND | ND |
| Acetate pH 5 | 5811gL14gH4 | 56.3 | 0.1 | 66.2 | 0 |
| | 5811gL8gH4 | 56.3 | 0 | 69 | 0 |
| | 5811gL5gH4 | 56.4 | 0 | 69.1 | 0.1 |

Experimental pI

The experimental pI of 5811gL14gH4, 5811gL8gH4 and 5811gL5gH4 was obtained using the whole-capillary imaged cIEF iCE3™ system (Protein Simple). Samples were prepared by mixing the following: 30 μL sample (from a 1 mg/mL stock in HPLC grade water), 35 μL of 1% tion of retention times. The retention time (RT) of the sample was normalized against the low and high hydrophobicity standards using the following equation:

[(Sample (RT)−low standard (RT)/High standard (RT)−low standard (RT)]×100

All three antibodies 5811gL14gH4, 5811gL8gH4 and 5811gL5gH4 showed similar normalized retention times and similar low hydrophobicity, that is, eluting from the column in less than 5 minutes (see Table 7). Low hydrophobicity aids stability (that is, reduces aggregation) during manufacture.

TABLE 7

| Antibody (Major Peak) | Retention Time (min) | Normalised Retention Time (min) |
|---|---|---|
| 5811gL14gH4 | 4.7 | 2.9 |
| 5811gL8gH4 | 4.7 | 2.9 |
| 5811gL5gH4 | 4.6 | 2.0 |

Solubility Measurement Using a Polyethylene Glycol (PEG) Precipitation Assay.

Colloidal stability of humanized antibodies 5811gL14gH4, 5811gL8gH4 and 5811gL5gH4 was analyzed using a polyethylene glycol (PEG) precipitation assay. PEG was used to reduce protein solubility in a quantitatively definable manner, by increasing the concentrations of PEG (w/v) and measuring the amount of protein remaining in solution. This assay served to mimic the effect of high concentration solubility without using conventional concentration methods.

PEG-induced precipitation of humanized antibodies 5811gL14gH4, 5811gL8gH4 and 5811gL5gH4 was investigated in the presence of 7-18% PEG-3350 in PBS pH 7.4 and 50 mM sodium acetate/125 mM sodium chloride pH 5.0. Antibody samples were buffer exchanged using dialysis and the concentration adjusted to 2 mg/mL. In order to minimize non-equilibrium precipitation, sample preparation consisted of mixing 2× protein and 2×PEG solutions at a 1:1 volume ratio. After mixing, samples were incubated at 37° C. for 30 minutes to re-dissolve non-equilibrium aggregates. Following an overnight incubation at 20° C. the samples were centrifuged for 60 min (4000 g). Aliquots of the supernatant were transferred to half volume 96 well optical plates and the absorbance at 280 nm was measured using a plate-reader BMG Labtech FLUOstar® Omega LVIS A280. The concentration data was plotted versus PEG %, and the calculated midpoint (Log EC50), (generated from a nonlinear regression curve fit, variable slope) was obtained as a measure of the relative colloidal solubility of samples. In this assay, the higher Log EC50 equates to a greater colloidal stability.

As shown in Table 8, no difference in colloidal stability was observed between the three different antibodies. Greater colloidal stability was observed in the acetate pH 5 buffer as shown by the larger log EC50 value.

surfaces are presented to the hydrophobic environment (air) and hydrophilic surfaces to the hydrophilic environment (water). Agitation of protein solutions achieves a large air-liquid interface that can drive aggregation.

Samples of humanized antibodies 5811gL14gH4, 5811gL8gH4 and 5811gL5gH4 in PBS pH 7.4 and 50 mM sodium acetate/125 mM sodium chloride pH 5.0 were stressed by vortexing using an Eppendorf Thermomixer Comfort™. Prior to vortexing the concentration was adjusted to 1 mg/mL using the appropriate extinction coefficients (1.41 Abs 280 nm, 1 mg/mL, 1 cm path length) and the absorbance at 280 nm, 340 nm and 595 nm obtained using a Varian Cary® 50-Bio spectrophotometer to establish the time zero reading. Each sample was aliquoted into 1.5 mL conical Eppendorf®-style capped tubes (4×250 µL) and subjected to stringent conditions in order to test robustness by vortexing at 1400 rpm at 25° C. for up to 24 hours. Time dependent aggregation (turbidity) was monitored by measurement of the samples at 24 hours post vortexing at 595 nm using a Varian Cary™ 50-Bio spectrophotometer. The mean absorbance values were plotted versus time for each sample.

Antibody molecule 5811gL5gH4 exhibited greater aggregation stability compared with 5811gL14gH4 and 5811gL8gH4. All antibodies showed greater aggregation stability in PBS pH 7.4.

Chemical Stability—Deamidation Stress Study

An accelerated stress study was performed using all three antibodies: 5811gL5gH4; 5811gL8gH4 and 5811gL14gH4 to determine deamidation propensity of one identified potential site: Asn(93) in the light chain of CDR3 where 5811gL14gH4 has an Asn(93)Ala motif and both 5811gL8gH4 and gL5gH4 have an Asn(93)Gly motif.

The three antibodies were subjected to conditions known to favor deamidation of Asn(N) residues (50 mM Tris/125 mM sodium chloride pH 8.0/37° C.). Additionally, samples were also prepared in 50 mM sodium acetate/125 mM sodium chloride pH 5.0 as a control condition to assess the basal deamidation prior to stressing. The final concentration of sample in each of the buffers was adjusted to ~5 mg/mL and then split into two aliquots where one was stored at 4° C. and one at 37° C. for up to 5 weeks. An aliquot was removed immediately (T0) and at 2 weeks and 5 weeks and stored at −20° C.

Basal deamidation at residue Asn(93) was measured on the non-stressed samples (50 mM sodium acetate/125 mM sodium chloride pH 5/4° C.) and the deamidation propensity of Asn(93) was obtained using the 2 week/pH 8/37° C. stressed samples by generating a tryptic peptide containing the sequence of interest. Briefly, 80 µg of each sample were reduced with DTT and denatured with guanidine hydrochlo-

TABLE 8

| Best-fit values | 50 mM NaOAc/125mMNaCl pH 5 | | | PBS pH 7.4 | | |
|---|---|---|---|---|---|---|
| | 5811gL14gH4 | 5811gL8gH4 | 5811gL5gH4 | 5811gL14gH4 | 5811gL8gH4 | 5811gL5gH4 |
| LogEC50 | 15.1 | 14.9 | 15.3 | 11.9 | 11.7 | 11.9 |
| HillSlope | −0.91 | −0.77 | −0.66 | −0.84 | −0.62 | −0.69 |
| $R^2$ std error | 0.987 | 0.989 | 0.965 | 0.994 | 0.985 | 0.99 |

Sigmoidal dose-response (variable slope)

Effect of Stress at Air-Liquid Interface (Aggregation Assay)

This assay serves to mimic the stresses that antibodies would be subjected to during manufacture (for example ultra-filtration). Proteins, such as antibodies, tend to unfold when exposed to an air-liquid interface, where hydrophobic ride at 37° C. Samples were then alkylated with iodoacetamide at room temperature, before buffer exchange into 7.5 mM Tris/1.5 mM CaCl$_2$) pH 7.9 (Zeba™ 7 kDa MWCO spin columns, Thermo Fisher) and approximately 3-hour incubation with trypsin (1:23 w/w) at 37° C. Proteolysis was stopped by adding trifluoroacetic acid to 0.1% v/v and samples stored at −20° C. On thawing, samples were centrifuged to remove precipitate.

The resulting peptides were separated and analyzed on a Waters BEH C18 column interfaced to a Thermo Fusion™ mass spectrometer running a positive-ion, data-dependent orbitrap-orbitrap method with collision induced dissociation (CID) fragmentation. LC-MS and $MS^2$ data were analyzed using Thermo Xcalibur™ and Pepfinder™ software. The peptide of interest (LC N93-K102) was analyzed to assess the percentage of chemical modification.

Peptide mapping mass spectrometry showed that the basal Asn(93) deamidation level was lower for 5811gL14gH4 compared with 5811gL8gH4 and 5811gL5gH4. The difference between the molecules was not unexpected since it has been shown that although prediction of deamidation propensity is difficult, Asn(N) residues followed by a Gly(G) residue show a greater propensity to deamidate than those followed with the bulkier Ala(A) residue (Robinson, N. E. et al., Proc. Natl. Acad. Sci. USA 2001, 98, 4367-4372).

For all three antibodies, a low rate of deamidation was observed at Asn(93), that is, 1.2%-1.4% per week. Mass differences of the light chain N93-K102 peptide for 5811gL5gH4 and 5811gL8gH4 included a −17 Da modification (likely the intermediate succinimide species) and +1 Da (fully deamidated product at Asn(93)), whereas the succinimide was not observed for 5811gL14gH4 (Table 9).

TABLE 9

| Percent (%) | Deamidation Asn(93) | | Succinimide formation | | Deamidation plus succinimide Increase in total chemical modification per week |
|---|---|---|---|---|---|
| | Basal | 2 weeks | Basal | 2 weeks | |
| 5811gL14gH4 | 1.2 | 4.1 | Not seen | Not seen | 1.4 |
| 5811gL8gH4 | 4.4 | 7.1 | 4.6 | 4.3 | 1.2 |
| 5811gL5gH4 | 5.6 | 8.6 | 4.8 | 4.3 | 1.3 |

The overall rate of deamidation was low for all antibodies although more heterogeneity was observed for 5811gL5gH4 and 5811gL8gH4.

Example 7: Cell-Based Appreciation Assay

HEK Freestyle 293F cells (suspension cells) were prepared at $0.7 \times 10^6$ cell/ml in Freestyle 293 Expression Medium (Invitrogen™) and cultured to $300 \times 10^6$ cell/ml. Transfection was performed according to manufacturer instructions and briefly 600 µg pcDNA3.1(+) incorporating the alpha-synuclein gene were mixed in 20 ml OptiMEM medium whilst 293Fectin was diluted in OptiMEM medium (Invitrogen™) and incubated for 5 minutes at room temperature. The diluted DNA was added and incubated at room temperature for 20 minutes before to be added drop by drop on the cells (20 ml per flask). The cells were incubated for 24 hours at 37° C., 125 rpm, 8% $CO_2$. Cells were either used immediately or frozen at concentration of 5 million cells/ml in FBS+10% DMSO.

If the cells had been previously frozen cryovials were thawed and cells resuspended in Freestyle 293 medium, centrifuged at 500 g for 5 minutes, the supernatant was discharged and the pellet was resuspended in Freestyle 293 medium (Life Technologies™)+ Pen/Strep (Invitrogen™) at $2 \times 10^6$ cells/ml. In a 384-well plate (Grainer™), 20 µl of cell suspension was added (to a total of ca. 40,000 cells/well). To each well, 150 nM of human alpha-synuclein fibrils (prepared as described herein in Example 1) were added followed by antibodies 5811gL5gH4 IgG4P, 5811 gL8gH4 IgG4P and 5811 gL14gH4 IgG4P (sequences in Table 1) in PBS to be tested (at various concentrations). The plates were incubated at 37° C., 5% $CO_2$, 95% humidity in a cell culture incubator for 2 days.

At the end of the second day, the medium was aspirated from all wells and the plate washed leaving 20 µl per well. About 50 µl of PBS was added to each well and the plates were centrifuged at 500 g for 5 minutes. The supernatant was aspirated from all wells with a plate washer, leaving 20 µl of medium in each well. Versene (Lonza™) was added (50 µl/well) and the plates were centrifuged at 500 g for 5 minutes, the supernatant was aspirated leaving only 20 µl of medium per well. Each well was supplemented with 20 µl 8% formaldehyde (16% solution in water, Life Technologies™)+2% Triton X-100 (VWR™) in PBS. The plates were incubated at room temperature for 15 minutes and thereafter 50 µl of FACS buffer consisting of HBSS (calcium-magnesium free VWR™)+2% FBS+2 mM EDTA, (Life Technologies™) were added. The plates were centrifuged at 2000 g for 1 minute and the supernatant was aspirated only leaving 20 µl of medium in each well. Each well was further supplemented with 20 µl of FACS buffer with anti-pSer129 alpha-synuclein antibody (AbCam™) diluted 1:300. The plates were incubated for 1 hour at room temperature and then each well was supplemented with 50 µl of FACS buffer before centrifuging again at 2000 g for 1 minute. The supernatant was removed before each well was supplemented with 1:500 diluted Alexafluor647-conjugated anti-rabbit-secondary antibody (Life Technologies™) and DAPI (Life Technologies™). Plates were incubated 1 hour at room temperature in the dark, and then 50 µl of FACS buffer was added and the plates centrifuged at 2000 g for 1 minute. Upon washing, more FACS buffer was added and the plates were ready to be placed in the flow cytometer (BD FACS Canto II) for reading.

Figure 10:
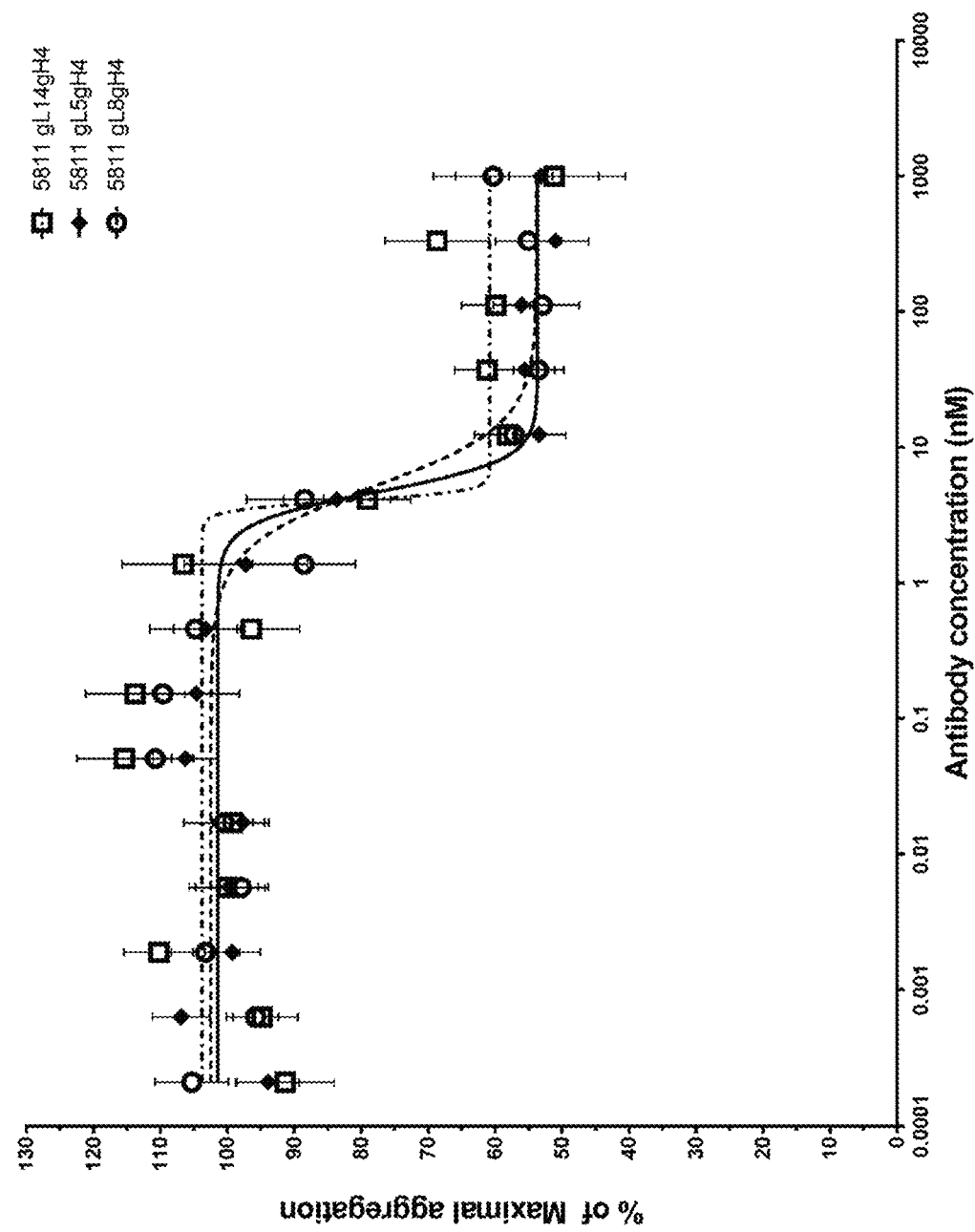
FIG. 10. Cell-based aggregation assay (HEK cells); antibodies of the present invention were able to inhibit alpha synuclein aggregation induced by alpha-synuclein fibrils, with $IC_{50}$ below 5 nM. Error bars represent standard error of measurement (SEM, N=4, n=12).

FACS data were analyzed using the FlowJo software. Firstly, live single cells were gated using forward and side scatter. Secondly, DAPI+ events were gated and their number was used as a measure of the number of live, nucleated single cells. Finally, phospho-serine 129-alpha-synuclein-positive (pSer129+) cells were gated. The percentage of pSer129+ cells relative to all DAPI+ cells was used as a measure of aggregation. Data were normalized relative to the wells treated with only fibrils and no antibody, and expressed as a percentage. Results are summarized in FIG. 10 which shows the ability of the antibodies tested to inhibit aggregation induced by alpha synuclein fibrils on cell expressing alpha synuclein. These data confirm that antibodies according to the present invention were able to block the aggregation induced by alpha-synuclein fibrils, with $IC_{50}$ about or lower than 5 nM.

Example 8: Primary Neurons Appreciation Assay

Hippocampi from E17 mouse embryos were dissected in dissection buffer (HBSS with no calcium and no magnesium, 0.6% D-(+)-Glucose, 20 mM Hepes). The dissection buffer was then removed and replaced by a dissociation solution (HBSS with no calcium and no magnesium, 0.6% D-(+)-Glucose, 20 mM HEPES, 40 U/m Papain, 1 mg/ml DNase, 1 mM L-cysteine, 0.5 mM EDTA). After 30 minutes incubation at 37° C., the dissociation buffer was removed and hippocampi were washed 3× with plating medium (Neurobasal™ Medium, 2% B27 supplement, 1 mM GlutaMAX, 2.5% FBS, 50 units/ml Penicillin-Streptomycin). Tissue clumps were triturated with a 1 ml pipette to obtain a single cell suspension. Cells were diluted to the appropriate concentration in plating medium. About 15000 cells were plated in each well of a PDL-coated 384-well plate. Cells were then kept in a cell culture incubator, at 37° C., 5% $CO_2$, 95% humidity.

The next day, 80% of the medium was replaced with plating medium without FBS [Neurobasal™ Medium, 2% B27 supplement, 1 mM GlutaMAX, 50 units/ml Penicillin-Streptomycin). Seven days after plating, the medium was removed leaving 20 µl in each well. To each well, 100 nM of human alpha-synuclein fibrils (prepared as described herein in Example 1) were added followed by antibodies 5811gL5gH4 IgG4P, 5811 gL8gH4 IgG4P and 5811 gL14gH4 IgG4P (sequences in Table 1) in PBS to be tested (at various concentrations). The plate was incubated at 37° C., 5% $CO_2$, 95% humidity in a cell culture incubator for an additional 7 days. Fourteen days after plating, the medium was aspirated from all wells leaving 20 µl per well. Each well was washed with 80 µl of Dulbecco's Phosphate Buffer Saline (DPBS). The DPBS was removed, and cells were incubated in 40 µl of fixation buffer (DPBS with 4% paraformaldehyde) per well for 15 minutes. The fixation buffer was then removed and cells were washed again with 80 µl of DPBS. The DPBS was removed and replaced by 40 µl of permeabilization buffer (DPBS with 0.1% Triton X-100) per well. After 10 minutes, the permeabilization buffer was removed, and cells were incubated for 1 hour in 40 µl of blocking buffer (PBS with 1% BSA and 0.1% Triton X-100) per well. The blocking buffer was then removed and replaced by 40 µl/well of primary antibody solution (blocking buffer with 0.3% rabbit anti-phospho-serine 129 alpha-synuclein antibody (AbCam™ ab51253). The antibody solution was incubated on the cells for 1 h, followed by three washes (90 µl/each, PBS). After the last wash, the PBS was removed and replaced by 40 µl of secondary antibody solution (0.1% AlexaFluor647-conjugated anti-rabbit antibody in PBS with 0.2% AlexaFluor488-conjugated anti-beta-III-tubulin antibody). The secondary antibody solution was incubated on the cells for 1 h, then removed and replaced by 40 µl of PBS comprising 0.3% CellMask Blue™. After 5 min of incubation, the wells were washed 3 times with 80 µl of PBS, then filled with 50 µl of PBS per well before the plate was sealed with clear plastic film.

Plates were imaged in an Arrayscan plate imager (ThermoFisher Scientific™). Images were analyzed using the HCS Scan™ software from the same manufacturer. Neuronal density was monitored using the beta-III-tubulin signal. Sparse fields or fields showing a damaged neuronal cell layer, reflected by a significant decrease in the surface of beta-III-tubulin signal, were excluded. Finally, the surface of pSer129 alpha synuclein signal per field was used to quantify pathological alpha-synuclein aggregation.

Phosphorylation at S129 of alpha synuclein is believed to play an important role in the control of alpha synuclein normal functions, as well as the regulation of its aggregation, LBs formation and neurotoxicity. Under normal conditions, only a small fraction of alpha synuclein is constitutively phosphorylated at S129 in the brain (Fujiwara H, et al. (2002) Nat Cell Biol, 4, 160-164), whereas a dramatic accumulation of pS129 has been observed in the brains of patients suffering from synucleinopathies (Kahle P J, et al. (2000) Ann N Y Acad Sci, 920, 33-41); Okochi M, et al. (2000) J Biol Chem, 275, 390-397); Anderson J P, et al. (2006) J Biol Chem, 281, 29739-29752).

Figure 11:
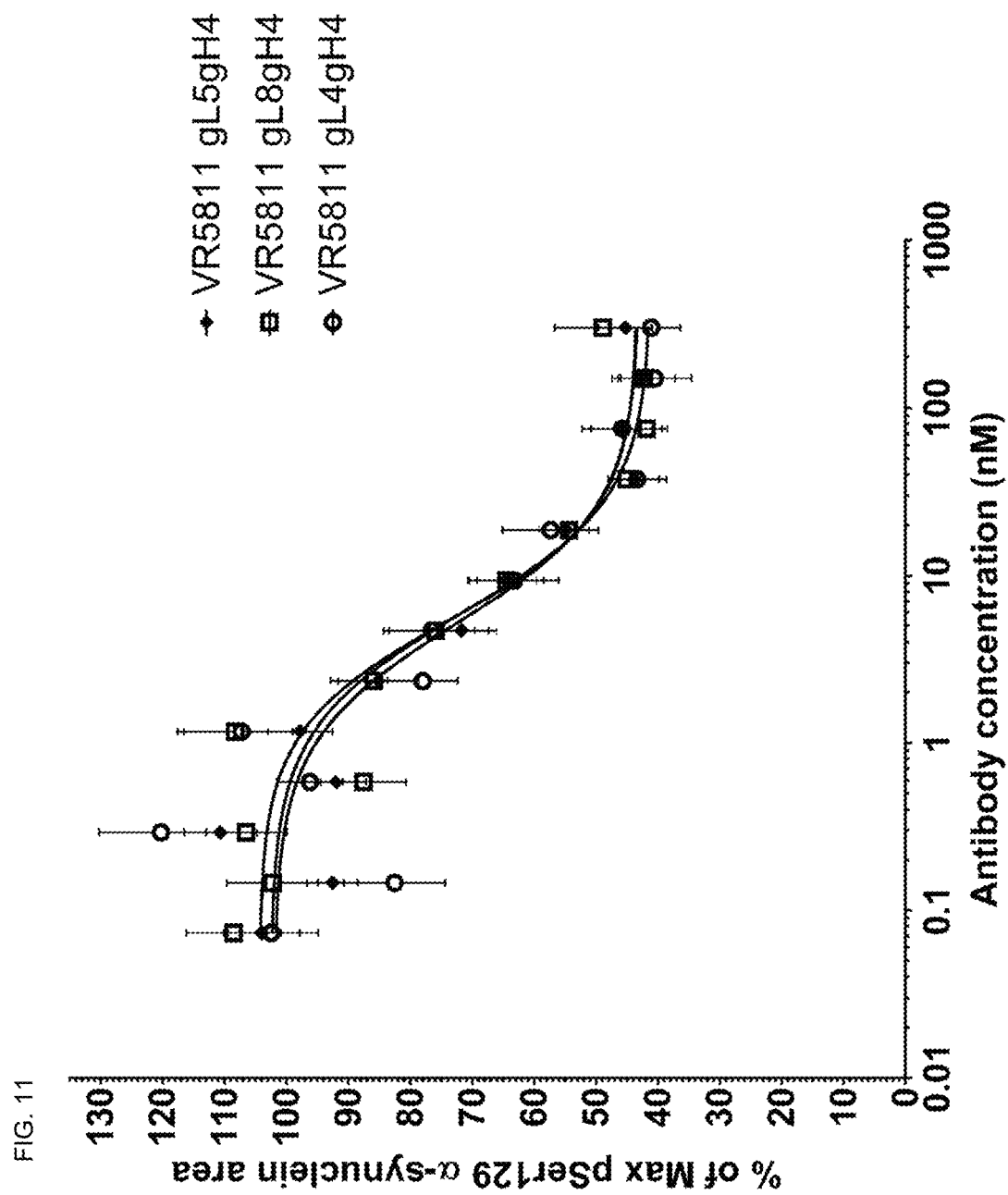
FIG. 11. Cell-based aggregation assay (primary neurons). Antibodies according to the present invention were able to inhibit alpha synuclein aggregation induced by alpha synuclein fibrils on mouse primary neurons expressing endogenous levels of alpha synuclein, with an $IC_{50}$ below 5 nM. Error bars represent standard error of mean (SEM, N=5, n=17).

Data were normalized relative to the wells treated with only fibrils and no antibody, and expressed as a percentage. As shown in FIG. 11, all three antibodies inhibited alpha synuclein aggregation induced by alpha synuclein fibrils on mouse primary neurons expressing endogenous levels of alpha synuclein. These data confirm that 5811gL5gH4 IgG4P, 5811 gL8gH4 IgG4P and 5811 gL14gH4 IgG4P antibodies were able to block the aggregation induced by alpha synuclein fibrils on mouse primary neurons, with $IC_{50}$ lower than 5 nM.

Example 9: Assessment of VR5811 Efficacy In Vivo

Antibody 5811gL5gH4 IgG4P (comprising SEQ ID NO: 14 and SEQ ID NO: 26 and hereinafter referred simply as VR5811) was tested in a transgenic model of α-synuclein knockout mouse expressing human alpha synuclein (thereafter named SNCA-OVX; Charles River, France).

SNCA-OVX mice were injected with VR5811 and murine pre-formed fibrils (PFF) (prepared as described herein in Example 1). A negative control antibody and vehicle were also injected along with a comparator anti-alpha synuclein antibody (comparator C-term Ab) which binds alpha synuclein at the last nine C-terminal residues. Such comparator antibody (which has different CDRs from the antibodies according to the present invention) showed comparable binding characteristics to the antibodies of the present invention. The comparator C-term Ab antibody possesses similar affinity for alpha synuclein as the antibodies of the present invention and similar biophysical properties. It was also effective in preventing alpha synuclein aggregation on cell-based assays (Table 10).

TABLE 10

| Antibody | Human Fibril | | | $IC_{50}$ |
| | ka1 (1/Ms) | kd1 (1/s) | KD1 (nM) | (nM) |
| --- | --- | --- | --- | --- |
| VR5811 | 2.74E+06 | 4.10E−05 | 0.015 | Less than 5 |
| Comparator C-term Ab | 1.08E+06 | 2.20E−05 | 0.02 | Less than 5 |

The antibodies were preincubated with the PFFs for 30 minutes, on a shaker at room temperature, before direct administration in the brain of the animals. The antibodies/PFFs mixtures were prepared in PBS at a ratio of 1 µg PFFs/10 µg antibodies. PBS at pH 7.4 was used as the vehicle solution. The antibody was injected 24 hours before the combined intracerebral administration The antibodies were then administered intraperitoneally to mice at a dose of 30 mg/kg. The second intraperitoneal injection was given 7 days after the first one, and then was pursued with the same regimen (one intraperitoneal injection/week at a dose of 30 mg/kg for a volume of administration of 10 ml/kg) for 11 weeks for a total of 12 injections for SNCA-OVX mice. The mice were randomly assigned to the drug treatment groups and the experimenters were blind to the treatment.

Animal experiments were performed according to the guidelines of the European Directive 2010/63/EU and Belgian legislation. The ethical committee for animal experimentation from UCB Biopharma SPRL (LA1220040 and LA2220363) approved the experimental protocol (ASYN-IC-PARKINSON-MO). The mice weighed between 25 and 30 g and were 17-week old at the time of surgery. The mice were housed in cages (4 mice per cage, Macrolon type 2). They were kept on a 12:12 light/dark cycle with light on at 06:00 h. Temperature was maintained at 20-21° C. and humidity was of approximately 40%. All animals had free access to standard pellet food and water before assignment to experimental groups. Additional enrichment and welfare were provided (Enviro-dri, Pharma Serv) before and after the surgery. Animal health was monitored daily by the animal care staff. All efforts were made to minimize suffering. Sacrifice were performed under anesthesia.

Surgery was performed under general anesthesia using a mixture of 50 mg/kg of ketamine (Nimatek, Eurovet Animal Health B.V.) and 0.5 mg/kg of medetomidine (Domitor, Orion Corporation) injected intraperitoneally. In addition, 2.5 mg/kg atipamezole (Antisedan, Orion Corporation) was given to support awakening. The recombinant purified PFFs were thawed and sonicated at room temperature (Qsonica 500—20 kHz; 65% power, for 30 pulses of 1 s ON, 1 s OFF for one minute). The PFFs were then premixed with the antibodies for 30 minutes and shaken at room temperature for 30 minutes before brain injection. The solution (2 μl) were infused at a rate of 0.2 μl/min and the needle was left in place for an additional 2.5 minutes before its slow retraction. Injections were carried out unilaterally in the right striatum at the following coordinates: AP=+0.20 mm, ML=−2.00 mm, DV=−3.20 mm.

Following anesthesia, the mice were perfused by transcardiac perfusion with ice-cold 0.9% PBS containing 10 U/ml heparin for 9 minutes at a flow rate of 6 ml/min via the left ventricle. The right atrium was cut as an outflow route. Subsequently, the animals were perfused with ice-cold 4% paraformaldehyde in PBS for 15 minutes at a flow rate of 6 ml/min. The brains were post-fixed overnight in PBS containing 4% paraformaldehyde at 4° C. (day 0). The next morning (day +1), the 4% paraformaldehyde was discarded and the brains were washed in cold PBS and incubated overnight. The next day (day +2) the brains were washed in PBS for a minimum of 1 hour and transferred to PBS containing 15% sucrose and stored at 4° C. until shipment.

Brain sectioning was performed at Neuroscience Associates (TN, USA). First, brains were treated overnight with 20% glycerol and 2% dimethyl sulfoxide to prevent freeze-artifacts, and embedded in a gelatin matrix using Multi-Brain® Technology. After curing, the blocks were rapidly frozen by immersion in isopentane chilled to −70° C. with crushed dry ice, and mounted on the freezing stage of an A0860 sliding microtome. The MultiBrain® blocks were sectioned in the coronal plane at 40 μm. All sections were collected sequentially into 24 containers per block that were filled with Antigen Preserve solution (49% PBS pH 7.0, 50% Ethylene glycol, 1% Polyvinyl Pyrrolidone). Sections not stained immediately were stored at −20° C.

Free-floating sections were stained by immunochemistry with pSer129 alpha synuclein antibody (mouse anti alpha synuclein (pSer129) Biotin-(Wako-010-26481)), diluted at 1:30,000. All incubation solutions from the blocking serum onward used Tris buffered saline (TBS) with Triton X-100 as the vehicle; all rinses were with TBS. Endogenous peroxidase activity was blocked by 0.9% hydrogen peroxide treatment and non-specific binding was blocked with 1.26% whole normal serum. Following rinses, the sections were stained with a primary antibody overnight at room temperature. Vehicle solution contained 0.3% Triton X-100 for permeabilization. Following rinses, sections were incubated with an avidin-biotin-HRP complex (Vectastain Elite ABC kit, Vector Laboratories, Burlingame, CA) for one hour at room temperature. Following rinses, the sections were treated with diaminobenzidine tetrahydrochloride (DAB) and 0.0015% hydrogen peroxide to create a visible reaction product, mounted on gelatinized (subbed) glass slides, air-dried, lightly stained with thionine, dehydrated in alcohols, cleared in xylene, and covered with Permount.

Quantification of pSer129 alpha synuclein signal per field pSer129 alpha synuclein signal was used to quantify pathological alpha-synuclein aggregation in the ipsilateral side of the striatum, cortex, basolateral amygdala, and substantia nigra. Regions of interest (ROI) were delineated manually and automatic quantification of pSer129 alpha synuclein signal in the different brain regions was performed with VisioPharm 6 software (VisioPharm). To quantify pSer129 alpha synuclein signal, the linear Bayesian algorithm, which provides a value of signal area (marker area in μm2), was used. Marker area reflects the amount of pSer129 alpha synuclein pathology that covers the different brain regions. All quantifications were performed in a blinded manner until the end of statistical analysis.

The data analyses were done on the % marker area (i.e. ratio between the pSer129 signal area in $\mu m^2$ and the Region of Interest area in $\mu m^2$). The % marker area was assessed repetitively for multiple brain sections positioned rostro-caudally (striatum: 13-14 sections from Bregma +1.1 to −0.94; cortex: 13-14 sections from +1.1 to −0.94; basolateral amygdala: 6-10 sections between −0.58 to −2.06; substantia nigra: 6-8 sections from −2.54 to −3.88), and an AUC was calculated separately for every tested subject.

One-way ANOVA were considered for statistical analysis. The ANOVA were followed by multiple pairwise comparisons among means without any multiplicity adjustment. (with **, for $p<0.01$ and *, for $p<0.05$). The data were log-transformed to meet the normality and homoscedasticity criteria. The graphs represent the geometric means of the untransformed data.

Figure 12:
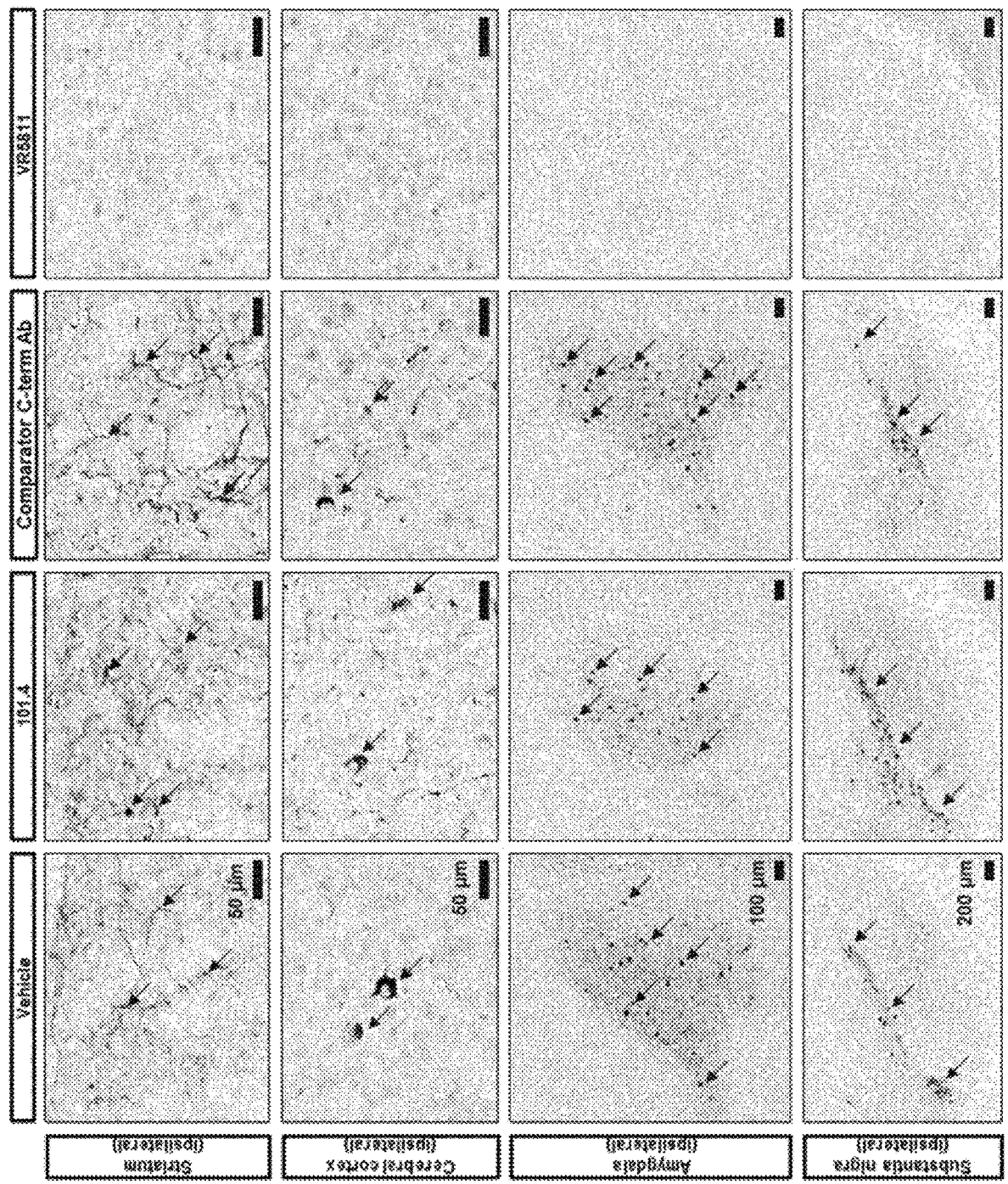
FIG. 12. Immuno-histochemistry pictures of alpha synuclein pathology (arrows) in different brain regions of SNCA-OVX mice injected with mouse PFF.

As shown in FIG. 12, VR5811 antibody markedly decreased alpha synuclein pathology (i.e. pSer129 alpha synuclein signal) in different brain regions including the striatum, cerebral cortex, amygdala and substantia nigra 3 months after PFFs administration to SNCA-OVX mice.

The negative control antibody and the comparator C-term. antibody showed no effect in decreasing the alpha synuclein pathology (pSer129 alpha synuclein signal) in comparison to vehicle-treated mice injected with the same human PFFs.

Figure 13:
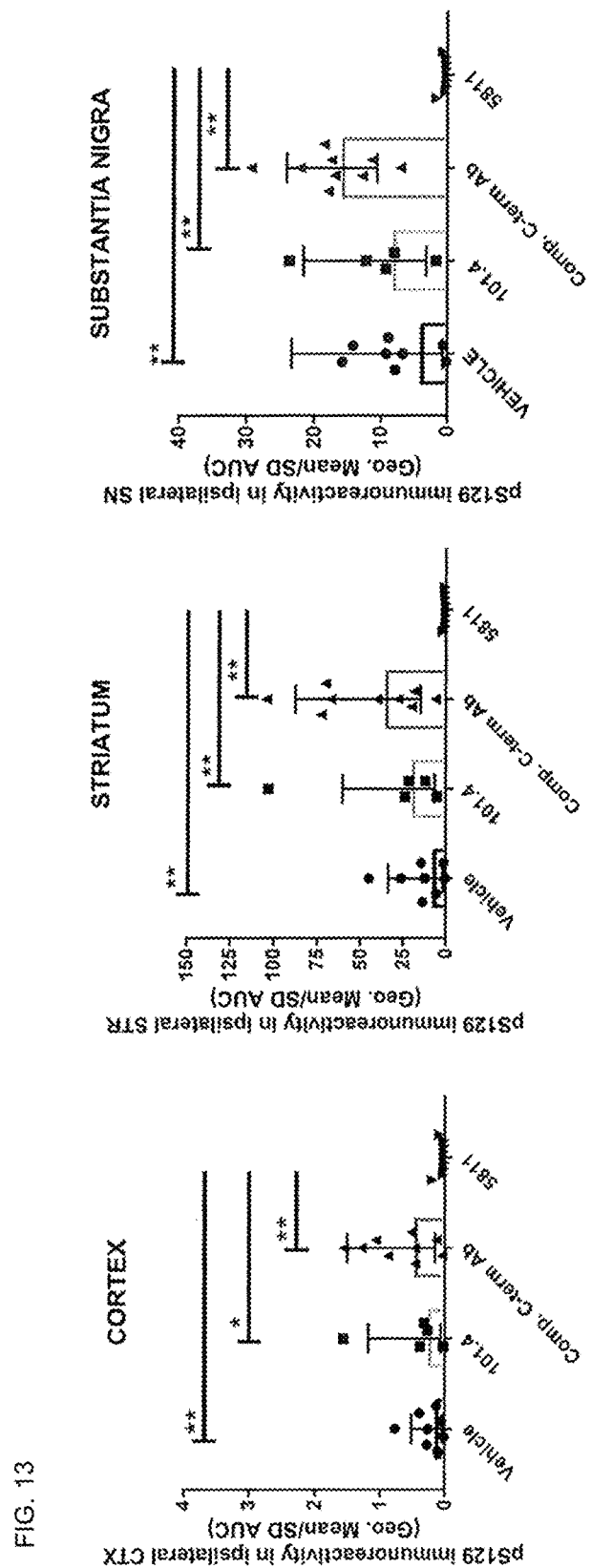
FIG. 13. Quantification of alpha synuclein pathology in different brain regions of SNCA-OVX mice in the cerebral cortex, striatum and substantia nigra.

FIG. 13 shows the quantification of alpha synuclein phosphorylated at Ser129 in each of the brain regions analyzed in SNCA-OVX mice. The results confirm that VR5811 significantly ($p<0.05$) reduces the alpha synuclein pathology in different brain regions including the ipsilateral side of the striatum, cerebral cortex and the substantia nigra in comparison with the three controls groups (i.e. vehicle, 101.4 and the Comp. C-term Ab).

As result, when tested in SNCA-OVX mice, the group treated with 5811 showed a significant reduced level of pSer129 α-synuclein in three different structures and amongst those, two were distal regions from the site of injection (cerebral cortex and substantia nigra).

This confirm that antibodies comprising the structural features of the present invention are capable of preventing in vivo the appearance of alpha synuclein phosphorylated at Ser129. Furthermore, the results demonstrate that not all antibodies that bind a-syn in the C-terminal region are efficacious in vivo: the comparator antibody, which binds to the C-terminus of a-syn with high affinity and is effective in preventing a-syn aggregation in cell based assays, failed to prevent Ser129 phosphorylation in vivo.

Therefore, the antibody or antigen-binding fragment thereof according to the present inventions can be used for treating alpha synucleinopathies characterized by an increase of Ser129 phosphorylation, including Parkinson's disease (PD) (including idiopathic and inherited forms of Parkinson's disease), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

Example 10: Pharmacokinetics of Antibody 5811 in Mouse

Male C57/Bl6 mice (n=3 per drug) were injected intravenously as a single dose of 2 mg/kg with antibody 5811gL14gH4 IgG4P (5811).

Blood samples were taken (0.083, 1, 4, 8, 24, 72, 120, 168 & 336 hours from injections) from the tail vein and allowed to clot at room temperature. Serum was isolated after centrifugation, which was then frozen until analysis. Quantification of 5811 antibody was carried out by LC-MS/MS. Serum samples from the study were defrosted and quantified against a calibration line prepared using 5811 antibody spiked at different concentrations into control mouse serum. Before injecting the samples onto the LC-MS/MS system, the serum was denatured, reduced and alkylated using acetonitrile (VWR, UK), TCEP-Tris(2-carboxyethyl) phosphine hydrochloride (Sigma, UK) and Iodoacetamide (Sigma, UK) respectively. The alkylated samples were then reconstituted in 100 mM ammonium bi-carbonate buffer (Sigma, UK) and digested overnight using trypsin (Promega, UK) enzyme at 37° C. The digestion was stopped by adding formic acid to the samples to lower the pH and then desalted using Waters HLB SPE plate. The resulting eluent was evaporated using vacuum evaporator. After the samples were completely dried they were reconstituted with 95/5: Water/Acetonitrile containing 0.1% formic acid and injected onto the LC-MS/MS system. LC-MS/MS analysis was carried out by Schimadzu prominence HPLC system coupled to AB Sciex QTrap 6500 triple quadruple mass spectrometer. The digested sample was injected by the autosampler onto a reversed-phase high-performance liquid chromatography column (Phenomenex Aeris C18 peptide column 100×2.1 mm, 2.6 μm) which was maintained at 50° C. A linear gradient of 5-70% acetonitrile in 0.1% formic acid was applied for 6 minutes and then ramped to 95% acetonitrile in 0.1% formic acid over 0.8 minutes at a flow rate of 0.6 ml/min. The mass spectrometer was set up to run multiple reaction monitoring analysis to detect multiple transitions of peptides of 5811 at a dwell time of 50 milliseconds per transition. Data analysis was carried using Analyst 1.6 software version.

Figure 14:
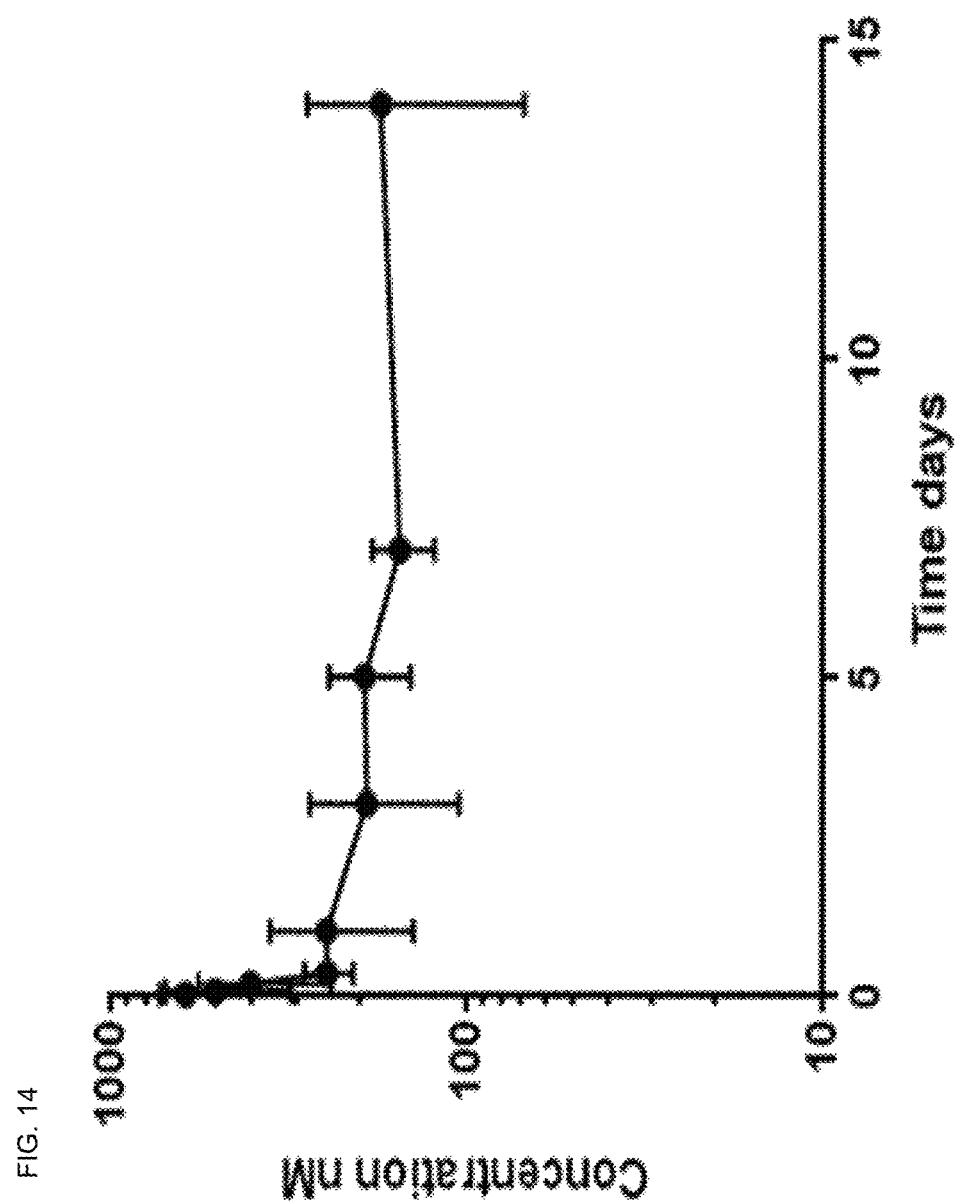
FIG. 14. Pharmacokinetic profiles of an alpha synuclein antibodies 5811 in wild type mouse.

These data demonstrate that antibody 5811 possesses very good pharmacokinetic properties (Table 11 and FIG. 14) in mouse, based on the low clearance values measured. These appear to be superior to the typical range quoted for human IgG drugs dosed to mice (3-16 ml/day/kg; Deng et al 2011 mabs 3:1 61-66).

TABLE 11

| Antibody | Clearance (SD) ml/day/kg Mouse |
|---|---|
| 5811 | 3.1 (1.0) |

The invention claimed is:

1. A method for detecting alpha synuclein in a biological sample, comprising:
   a) contacting the biological sample with an anti-alpha synuclein antibody or antigen-binding fragment thereof, and
   b) detecting binding of the anti-alpha synuclein antibody or antigen-binding fragment thereof to alpha synuclein; wherein the antibody or antigen-binding fragment thereof comprises:
      i. a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6; or
      ii. a light chain variable region comprising SEQ ID NO: 13 and a heavy chain variable region comprising SEQ ID NO: 25; or a light chain variable region comprising SEQ ID NO: 17 and a heavy chain variable region comprising SEQ ID NO: 25; or a light chain variable region comprising SEQ ID NO: 21 and a heavy chain variable region comprising SEQ ID NO: 25; or
      iii. a light chain comprising SEQ ID NO: 14 and a heavy chain comprising SEQ ID SEQ ID NO: 26; or a light chain comprising SEQ ID NO: 18 and a heavy chain comprising SEQ ID SEQ ID NO: 26; or a light chain comprising SEQ ID NO: 22 and a heavy chain comprising SEQ ID SEQ ID NO: 26.

2. The method of claim 1, wherein the antibody or antigen-binding fragment thereof comprises: a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6.

3. The method of claim 1, wherein the antibody or antigen-binding fragment thereof comprises: a light chain variable region comprising a CDR-L1 comprising SEQ ID NO: 1; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6, wherein amino acid residue glycine (Gly; G) at position 6 with reference to SEQ ID NO: 3 is replaced by alanine (Ala; A).

4. The method of claim 1, wherein the antibody or antigen-binding fragment thereof comprises: a light chain variable region comprising SEQ ID NO: 13 and a heavy chain variable region comprising SEQ ID NO: 25.

5. The method of claim 1, wherein the antibody or antigen-binding fragment thereof comprises: a light chain variable region comprising SEQ ID NO: 17 and a heavy chain variable region comprising SEQ ID NO: 25.

6. The method of claim 1, wherein the antibody or antigen-binding fragment thereof comprises: a light chain variable region comprising SEQ ID NO: 21 and a heavy chain variable region comprising SEQ ID NO: 25.

7. The method of claim 1, wherein the antibody or antigen-binding fragment thereof comprises: a light chain comprising SEQ ID NO: 14 and a heavy chain comprising SEQ ID SEQ ID NO: 26.

8. The method of claim 1, wherein the antibody or antigen-binding fragment thereof comprises: a light chain comprising SEQ ID NO: 18 and a heavy chain comprising SEQ ID SEQ ID NO: 26.

9. The method of claim 1, wherein the antibody or antigen-binding fragment thereof comprises: a light chain comprising SEQ ID NO: 22 and a heavy chain comprising SEQ ID SEQ ID NO: 26.

10. The method of claim 1, wherein the biological sample is from a subject suspected of having an alpha synucleinopathy, wherein the alpha synucleinopathy is selected from the group consisting of Parkinson's disease (PD), dementia with Lewy bodies (DLB), Diffuse Lewy Body Disease (DLBD), Lewy body variant of Alzheimer's disease (LBVAD), combined Alzheimer's and Parkinson's disease, multiple system atrophy (MSA), and neurodegeneration with brain iron accumulation type-1 (NBIA-1).

11. The method of claim 10, wherein the Parkinson's disease comprises idiopathic or inherited forms of Parkinson's disease.

12. The method of claim 10, wherein the alpha synucleinopathy is Parkinson's disease.

13. The method of claim 1, wherein the biological sample comprises cerebrospinal fluid, blood plasma, blood serum, or solid tissue samples.

14. The method of claim 13, wherein the sample is a solid tissue sample comprising a biopsy specimen, tissue cultures or cells derived therefrom, or the progeny thereof.

15. The method of claim 1, wherein after (b), the method further comprises comparing the detected alpha synuclein or a post-translationally modified form of alpha synuclein with a suitable control.

* * * * *

UNITED STATES PATENT AND TRADEMARK OFFICE
CERTIFICATE OF CORRECTION

PATENT NO. : 12,410,244 B2  
APPLICATION NO. : 17/682082  
DATED : September 9, 2025  
INVENTOR(S) : Patrick Downey et al.

Page 1 of 1

It is certified that error appears in the above-identified patent and that said Letters Patent is hereby corrected as shown below:

In the Claims

Column 97, Line 43, Claim 1: replace "comprising SEQ ID SEQ ID NO: 26" with -- comprising SEQ ID NO: 26 --.

Column 97, Line 45, Claim 1: replace "comprising SEQ ID SEQ ID NO: 26" with -- comprising SEQ ID NO: 26 --.

Column 97, Line 47, Claim 1: replace "comprising SEQ ID SEQ ID NO: 26" with -- comprising SEQ ID NO: 26 --.

Column 98, Lines 31-32, Claim 7: replace "comprising SEQ ID SEQ ID NO: 26" with -- comprising SEQ ID NO: 26 --.

Column 98, Lines 35-36, Claim 8: replace "comprising SEQ ID SEQ ID NO: 26" with -- comprising SEQ ID NO: 26 --.

Column 98, Lines 39-40, Claim 9: replace "comprising SEQ ID SEQ ID NO: 26" with -- comprising SEQ ID NO: 26 --.

Signed and Sealed this  
Eighteenth Day of November, 2025

John A. Squires  
*Director of the United States Patent and Trademark Office*

SEQUENCE LISTING

```
<160> NUMBER OF SEQ ID NOS: 48

<210> SEQ ID NO 1
<211> LENGTH: 11
<212> TYPE: PRT
<213> ORGANISM: Rattus norvegicus

<400> SEQUENCE: 1

Lys Ala Ser Gln Asn Ile Asn Lys Asn Leu Asp
1               5                   10

<210> SEQ ID NO 2
<211> LENGTH: 7
<212> TYPE: PRT
<213> ORGANISM: Rattus norvegicus

<400> SEQUENCE: 2

Tyr Ala Asn Asn Leu Gln Thr
1               5

<210> SEQ ID NO 3
<211> LENGTH: 8
<212> TYPE: PRT
<213> ORGANISM: Rattus norvegicus

<400> SEQUENCE: 3

Tyr Gln Tyr Lys Asn Gly Trp Thr
```

```
<210> SEQ ID NO 4
<211> LENGTH: 10
<212> TYPE: PRT
<213> ORGANISM: Rattus norvegicus

<400> SEQUENCE: 4

Gly Phe Thr Phe Asn Asn Ala Ala Met Tyr
1               5                   10

<210> SEQ ID NO 5
<211> LENGTH: 19
<212> TYPE: PRT
<213> ORGANISM: Rattus norvegicus

<400> SEQUENCE: 5

Arg Ile Arg Thr Lys Pro Asn Asn Tyr Ala Thr Ser Tyr Ala Asp Ser
1               5                   10                  15

Val Lys Gly

<210> SEQ ID NO 6
<211> LENGTH: 7
<212> TYPE: PRT
<213> ORGANISM: Rattus norvegicus

<400> SEQUENCE: 6

Asp Tyr Ser Arg Gly Asp Arg
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: CDR-L3 variant 1

<400> SEQUENCE: 7

Tyr Gln Tyr Lys Asn Ala Trp Thr
1               5

<210> SEQ ID NO 8
<211> LENGTH: 140
<212> TYPE: PRT
<213> ORGANISM: Homo sapiens

<400> SEQUENCE: 8

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95
```

```
Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 9
<211> LENGTH: 106
<212> TYPE: PRT
<213> ORGANISM: Rattus norvegicus

<400> SEQUENCE: 9

Asn Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Met
        35                  40                  45

Tyr Tyr Ala Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Lys Asn Gly Trp Thr
                85                  90                  95

Phe Gly Gly Gly Thr Lys Leu Glu Leu Lys
            100                 105

<210> SEQ ID NO 10
<211> LENGTH: 118
<212> TYPE: PRT
<213> ORGANISM: Rattus norvegicus

<400> SEQUENCE: 10

Glu Met Gln Leu Val Glu Ser Gly Gly Gly Leu Val Gln Pro Lys Glu
1               5                   10                  15

Ser Leu Lys Ile Ser Cys Ala Ala Ser Gly Phe Thr Phe Asn Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Ser Tyr Ala Asp
    50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Ser Glu Asp Thr Ala Met Tyr
                85                  90                  95

Tyr Cys Thr Ala Asp Tyr Ser Arg Gly Asp Arg Trp Gly Gln Gly Val
            100                 105                 110

Met Val Thr Val Ser Ser
        115

<210> SEQ ID NO 11
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

<223> OTHER INFORMATION: Rat VL nucleotide

<400> SEQUENCE: 11

```
aacatccaga tgacccagtc tcctccagtc ctgtctgcat ctgtgggaga cagagtcact    60
ctcagctgca aagcaagtca gaacattaat aagaacttag actggtatca gcaaaagcat   120
ggagaagctc caaaactcct gatgtattat gcaaacaatt tacaaacggg catcccatca   180
aggttcagtg gcagtggatc tggaacagat tacacgctca ccatcagcag cctgcagcct   240
gaagatgttg ccacatatta ctgctatcag tataagaatg ggtggacgtt cggtggaggc   300
accaagctgg aactgaaa                                                 318
```

<210> SEQ ID NO 12
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Rat VH nucleotide

<400> SEQUENCE: 12

```
gaaatgcagc tggtggagtc tggtggagga ttggtgcagc ctaaggagtc attgaaaatc    60
tcatgtgcag cctctggatt cacctttcaat aatgctgcca tgtactgggt ccgccaggct  120
ccaggaaagg gtctggaatg ggttgctcgc ataagaacta aacctaataa ttatgcaaca   180
tcttatgctg attcagtgaa aggcagattc accatctcca gagatgattc aaaaagcatg   240
gtctacctac aaatggataa cttgaaaagt gaggacacag ccatgtatta ctgtacagca   300
gattactcca gaggtgacag gtggggccaa ggagtcatgg tcacagtctc gagc         354
```

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 gL5 V-region

<400> SEQUENCE: 13

```
Asp Ile Gln Met Thr Gln Ser Pro Ser Ser Leu Ser Ala Ser Val Gly
1               5                  10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45

Tyr Tyr Ala Asn Asn Leu Gln Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Lys Asn Gly Trp Thr
                85                  90                  95

Phe Gly Gln Gly Thr Lys Val Glu Ile Lys
            100                 105
```

<210> SEQ ID NO 14
<211> LENGTH: 213
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 gL5 Light chain

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45

Tyr Tyr Ala Asn Asn Leu Gln Thr Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Lys Asn Gly Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 15
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gL5 V-region nucleotide

<400> SEQUENCE: 15

```
gacatccaga tgacccagag cccgagctcc ctgtccgcat cagtggggga tcgcgtgact      60
attacgtgca aagcctcgca gaacatcaac aagaacctcg actggtatca gcagaagcca     120
ggaaaggcgc ctaagctgct gatctactac gccaacaatc tccagaccgg cgtgccctcg     180
cggttctccg gatctgggtc cggtactgat tacaccctga ccattagctc ccttcaaccg     240
gaggacttcg ccacctatta ctgctaccag tacaagaacg gctggacttt tggacaaggc     300
accaaggtcg aaatcaag                                                   318
```

<210> SEQ ID NO 16
<211> LENGTH: 639

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gL5 Light chain nucleotide

<400> SEQUENCE: 16

```
gacatccaga tgacccagag cccgagctcc ctgtccgcat cagtggggga tcgcgtgact    60
attacgtgca aagcctcgca gaacatcaac aagaacctcg actggtatca gcagaagcca   120
ggaaaggcgc ctaagctgct gatctactac gccaacaatc tccagaccgg cgtgccctcg   180
cggttctccg gatctgggtc cggtactgat tacaccctga ccattagctc ccttcaaccg   240
gaggacttcg ccacctatta ctgctaccag tacaagaacg gctggacttt tggacaaggc   300
accaaggtcg aaatcaagcg tacggtggcc gctccctccg tgttcatctt cccaccctcc   360
gacgagcagc tgaagtccgg caccgcctcc gtcgtgtgcc tgctgaacaa cttctacccc   420
cgcgaggcca aggtgcagtg gaaggtggac aacgccctgc agtccggcaa ctcccaggaa   480
tccgtcaccg agcaggactc caaggacagc acctactccc tgtcctccac cctgaccctg   540
tccaaggccg actacgagaa gcacaaggtg tacgcctgcg aagtgaccca ccagggcctg   600
tccagccccg tgaccaagtc cttcaaccgg ggcgagtgc                          639
```

<210> SEQ ID NO 17
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 gL8 V-region

<400> SEQUENCE: 17

```
Asp Ile Gln Met Thr Gln Ser Pro Ser Ser Leu Ser Ala Ser Val Gly
1               5                  10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45

Tyr Tyr Ala Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Tyr Gln Tyr Lys Asn Gly Trp Thr
                85                  90                  95

Phe Gly Gln Gly Thr Lys Val Glu Ile Lys
            100                 105
```

<210> SEQ ID NO 18
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 gL8 Light chain

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
            35                  40                  45

Tyr Tyr Ala Asn Asn Leu Gln Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Tyr Gln Tyr Lys Asn Gly Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 V-region nucleotide

<400> SEQUENCE: 19
gacatccaga tgacccagag cccgagctcc ctgtccgcat cagtggggga tcgcgtgact      60
attacgtgca aagcctcgca gaacatcaac aagaacctcg actggtatca gcagaagcca     120
ggaaaggcgc ctaagctgct gatctactac gccaacaatc tccagaccgg cgtgccctcg     180
cggttctccg gatctgggtc cggtactgat ttcaccctga ccattagctc ccttcaaccg     240
gaggacttcg ccacctatta ctgctaccag tacaagaacg gctggacttt tggacaaggc     300
accaaggtcg aaatcaag                                                   318

<210> SEQ ID NO 20
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gL8 Light chain nucleotide

<400> SEQUENCE: 20

```
gacatccaga tgacccagag cccgagctcc ctgtccgcat cagtggggga tcgcgtgact    60
attacgtgca aagcctcgca gaacatcaac aagaacctcg actggtatca gcagaagcca   120
ggaaaggcgc ctaagctgct gatctactac gccaacaatc tccagaccgg cgtgccctcg   180
cggttctccg gatctgggtc cggtactgat ttcaccctga ccattagctc ccttcaaccg   240
gaggacttcg ccacctatta ctgctaccag tacaagaacg ctggacttt tggacaaggc    300 accaaggtcg aaatcaagcg tacggtggcc gctccctccg tgttcatctt cccaccctcc   360
gacgagcagc tgaagtccgg caccgcctcc gtcgtgtgcc tgctgaacaa cttctacccc   420
cgcgaggcca aggtgcagtg gaaggtggac aacgccctgc agtccggcaa ctcccaggaa   480
tccgtcaccg agcaggactc caaggacagc acctactccc tgtcctccac cctgaccctg   540
tccaaggccg actacgagaa gcacaaggtg tacgcctgcg aagtgaccca ccagggcctg   600
tccagccccg tgaccaagtc cttcaaccgg ggcgagtgc                          639
```

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 5811 gL14 V-region

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45

Tyr Tyr Ala Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Tyr Gln Tyr Lys Asn Ala Trp Thr
                85                  90                  95

Phe Gly Gln Gly Thr Lys Val Glu Ile Lys
            100                 105
```

<210> SEQ ID NO 22
<211> LENGTH: 213
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 5811 gL14 Light chain

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Asn
            20                  25                  30

Leu Asp Trp Tyr Gln Gln Lys Pro Gly Lys Ala Pro Lys Leu Leu Ile
        35                  40                  45
```

-continued

Tyr Tyr Ala Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Tyr Gln Tyr Lys Asn Ala Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 23
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gL14 V-region nucleotide

<400> SEQUENCE: 23
gacatccaga tgacccagag cccgagctcc ctgtccgcat cagtggggga tcgcgtgact      60
attacgtgca aagcctcgca gaacatcaac aagaacctcg actggtatca gcagaagcca     120
ggaaaggcgc ctaagctgct gatctactac gccaacaatc tccagaccgg cgtgccctcg     180
cggttctccg gatctgggtc cggtactgat ttcacccctga ccattagctc ccttcaaccg    240
gaggacttcg ccacctatta ctgctaccag tacaagaacg cttggacttt tggacaaggc     300
accaaggtcg aaatcaag                                                   318

<210> SEQ ID NO 24
<211> LENGTH: 639
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gL14 Light chain nucleotide

<400> SEQUENCE: 24
gacatccaga tgacccagag cccgagctcc ctgtccgcat cagtggggga tcgcgtgact      60
attacgtgca aagcctcgca gaacatcaac aagaacctcg actggtatca gcagaagcca     120
ggaaaggcgc ctaagctgct gatctactac gccaacaatc tccagaccgg cgtgccctcg     180
cggttctccg gatctgggtc cggtactgat ttcacccctga ccattagctc ccttcaaccg    240

```
gaggacttcg ccacctatta ctgctaccag tacaagaacg cttggacttt tggacaaggc    300
accaaggtcg aaatcaagcg tacggtggcc gctccctccg tgttcatctt cccaccctcc    360
gacgagcagc tgaagtccgg caccgcctcc gtcgtgtgcc tgctgaacaa cttctacccc    420
cgcgaggcca aggtgcagtg gaaggtggac aacgccctgc agtccggcaa ctcccaggaa    480
tccgtcaccg agcaggactc caaggacagc acctactccc tgtcctccac cctgaccctg    540
tccaaggccg actacgagaa gcacaaggtg tacgcctgcg aagtgaccca ccagggcctg    600
tccagccccg tgaccaagtc cttcaaccgg ggcgagtgc                          639
```

<210> SEQ ID NO 25
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 gH4 V-region

<400> SEQUENCE: 25

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Ser Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ala Asp Tyr Ser Arg Gly Asp Arg Trp Gly Gln Gly Thr
            100                 105                 110

Met Val Thr Val Ser Ser
        115
```

<210> SEQ ID NO 26
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 gH4 Heavy chain

<400> SEQUENCE: 26

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Ser Tyr Ala Asp
    50                  55                  60

Ser Val Lys Gly Arg Phe Thr Ile Ser Arg Asp Asp Ser Lys Asn Thr
65                  70                  75                  80
```

```
Leu Tyr Leu Gln Met Asn Ser Leu Lys Thr Glu Asp Thr Ala Val Tyr
                85                  90                  95

Tyr Cys Thr Ala Asp Tyr Ser Arg Gly Asp Arg Trp Gly Gln Gly Thr
            100                 105                 110

Met Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 27
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gH4 V-region nucleotide
```

<400> SEQUENCE: 27

```
gaagtgcagc ttgtggagag cggaggtgga ctcgtgaagc ctggcggatc tctgcgcctg      60
tcctgcgccg cctcggggtt cacctttaac aatgccgcaa tgtattgggt cagacaggcc     120
ccgggaaagg gtttggaatg ggtggctagg attcggacta agcccaacaa ctacgcgacc     180
tcctacgccg atagcgtgaa gggcagattc accatctccc gggacgactc aaagaacacg     240
ctgtacctcc aaatgaactc cctgaaaacc gaggacaccg ccgtgtacta ctgcaccgcg     300
gactactccc ggggcgatcg ctggggacag gggactatgg tcactgtctc gagt           354
```

<210> SEQ ID NO 28
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 5811 gH4 Heavy chain nucleotide

<400> SEQUENCE: 28

```
gaagtgcagc ttgtggagag cggaggtgga ctcgtgaagc ctggcggatc tctgcgcctg      60
tcctgcgccg cctcggggtt cacctttaac aatgccgcaa tgtattgggt cagacaggcc     120
ccgggaaagg gtttggaatg ggtggctagg attcggacta agcccaacaa ctacgcgacc     180
tcctacgccg atagcgtgaa gggcagattc accatctccc gggacgactc aaagaacacg     240
ctgtacctcc aaatgaactc cctgaaaacc gaggacaccg ccgtgtacta ctgcaccgcg     300
gactactccc ggggcgatcg ctggggacag gggactatgg tcactgtctc gagtgcctcc     360
accaagggcc cctccgtgtt ccctctggcc ccttgctccc ggtccacctc cgagtctacc     420
gccgctctgg gctgcctggt caaggactac ttccccgagc ccgtgacagt gtcctggaac     480
tctggcgccc tgacctccgg cgtgcacacc ttccctgccg tgctgcagtc ctccggcctg     540
tactccctgt cctccgtcgt gaccgtgccc tcctccagcc tgggcaccaa gacctacacc     600
tgtaacgtgg accacaagcc ctccaacacc aaggtggaca gcggtgtgga atctaagtac     660
ggccctccct gcccccctg ccctgcccct gaatttctgg gcggaccttc cgtgttcctg     720 ttcccccaa gcccaagga caccctgatg atctcccgga cccccgaagt gacctgcgtg     780
gtggtggacg tgcccagga agatcccgag gtccagttca attggtacgt ggacggcgtg     840
gaagtgcaca atgccaagac caagcccaga gaggaacagt tcaactccac ctaccgggtg     900
gtgtccgtgc tgaccgtgct gcaccaggac tggctgaacg gcaaagagta caagtgcaag     960
gtgtccaaca agggcctgcc ctccagcatc gaaaagacca tctccaaggc caagggccag    1020
ccccgcgagc cccaggtgta caccctgccc cctagccagg aagagatgac caagaaccag    1080
gtgtccctga cctgtctggt caagggcttc taccccagg acattgccgt ggaatgggag    1140
tccaacggcc agcccgagaa caactacaag accaccccc ctgtgctgga cagcgacggc    1200
tccttcttcc tgtactccaa gctgaccgtg gacaagtccc ggtggcagga aggcaacgtc    1260
ttctcctgct ccgtgatgca cgaggccctg cacaaccact acacccagaa gtccctgtcc    1320
ctgagcctgg gcaag                                                    1335
```

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 30
<211> LENGTH: 116
<212> TYPE: PRT
<213> ORGANISM: Homo sapiens

<400> SEQUENCE: 30

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Ala Phe Asp Val Trp Gly Gln Gly Thr Met Val
            100                 105                 110

Thr Val Ser Ser
        115

<210> SEQ ID NO 31
<211> LENGTH: 321
<212> TYPE: DNA
<213> ORGANISM: Homo sapiens

<400> SEQUENCE: 31
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat tcactctca ccatcagcag tctgcaacct    240
gaagattttg caacttacta ctgtcaacag agttacagta ccccttggac gttcggccaa    300
gggaccaagg tggaaatcaa a                                                321

<210> SEQ ID NO 32
<211> LENGTH: 348

```
<212> TYPE: DNA
<213> ORGANISM: Homo sapiens

<400> SEQUENCE: 32
gaggtgcagc tggtggagtc tgggggaggc ttggtaaagc ctgggggtc ccttagactc      60 tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtaccaca     300
gatgcttttg atgtctgggg ccaagggaca atggtcaccg tctcttca                 348

<210> SEQ ID NO 33
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Rabbit Fc human 68-140 a-syn

<400> SEQUENCE: 33
```

Gly Ala Val Val Thr Gly Val Thr Ala Val Ala Gln Lys Thr Val Glu
1               5                   10                  15

Gly Ala Gly Ser Ile Ala Ala Ala Thr Gly Phe Val Lys Lys Asp Gln
            20                  25                  30

Leu Gly Lys Asn Glu Glu Gly Ala Pro Gln Glu Gly Ile Leu Glu Asp
        35                  40                  45

Met Pro Val Asp Pro Asp Asn Glu Ala Tyr Glu Met Pro Ser Glu Glu
    50                  55                  60

Gly Tyr Gln Asp Tyr Glu Pro Glu Ala Val Glu Lys Thr Val Ala Pro
65                  70                  75                  80

Ser Thr Cys Ser Lys Pro Thr Cys Pro Pro Glu Leu Leu Gly Gly
                85                  90                  95

Pro Ser Val Phe Ile Phe Pro Pro Lys Pro Lys Asp Thr Leu Met Ile
            100                 105                 110

Ser Arg Thr Pro Glu Val Thr Cys Val Val Val Asp Val Ser Gln Asp
        115                 120                 125

Asp Pro Glu Val Gln Phe Thr Trp Tyr Ile Asn Asn Glu Gln Val Arg
    130                 135                 140

Thr Ala Arg Pro Pro Leu Arg Glu Gln Gln Phe Asn Ser Thr Ile Arg
145                 150                 155                 160

Val Val Ser Thr Leu Pro Ile Ala His Gln Asp Trp Leu Arg Gly Lys
                165                 170                 175

Glu Phe Lys Cys Lys Val His Asn Lys Ala Leu Pro Ala Pro Ile Glu
            180                 185                 190

Lys Thr Ile Ser Lys Ala Arg Gly Gln Pro Leu Glu Pro Lys Val Tyr
        195                 200                 205

Thr Met Gly Pro Pro Arg Glu Glu Leu Ser Ser Arg Ser Val Ser Leu
    210                 215                 220

Thr Cys Met Ile Asn Gly Phe Tyr Pro Ser Asp Ile Ser Val Glu Trp
225                 230                 235                 240

Glu Lys Asn Gly Lys Ala Glu Asp Asn Tyr Lys Thr Thr Pro Ala Val
                245                 250                 255

Leu Asp Ser Asp Gly Ser Tyr Phe Leu Tyr Ser Lys Leu Ser Val Pro

```
                        260                 265                 270
Thr Ser Glu Trp Gln Arg Gly Asp Val Phe Thr Cys Ser Val Met His
            275                 280                 285

Glu Ala Leu His Asn His Tyr Thr Gln Lys Ser Ile Ser Arg Ser Pro
        290                 295                 300

Gly Lys
305

<210> SEQ ID NO 34
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 rat-mouse chimeric light chain

<400> SEQUENCE: 34

Asn Ile Gln Met Thr Gln Ser Pro Pro Val Leu Ser Ala Ser Val Gly
1               5                   10                  15

Asp Arg Val Thr Leu Ser Cys Lys Ala Ser Gln Asn Ile Asn Lys Asn
            20                  25                  30

Leu Asp Trp Tyr Gln Gln Lys His Gly Glu Ala Pro Lys Leu Leu Met
        35                  40                  45

Tyr Tyr Ala Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Lys Asn Gly Trp Thr
                85                  90                  95

Phe Gly Gly Gly Thr Lys Leu Glu Leu Lys Arg Thr Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 35
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 rat-mouse chimeric heavy chain

<400> SEQUENCE: 35
```

-continued

```
Glu Met Gln Leu Val Glu Ser Gly Gly Gly Leu Val Gln Pro Lys Glu
1               5                   10                  15

Ser Leu Lys Ile Ser Cys Ala Ala Ser Gly Phe Thr Phe Asn Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Ser Tyr Ala Asp
    50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Ser Glu Asp Thr Ala Met Tyr
                85                  90                  95

Tyr Cys Thr Ala Asp Tyr Ser Arg Gly Asp Arg Trp Gly Gln Gly Val
            100                 105                 110

Met Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asp Thr Asp Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
```

```
                    420             425             430
Glu Lys Ser Leu Ser His Ser Pro Gly Lys
        435             440

<210> SEQ ID NO 36
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 5811 rat-mouse chimeric Fab-His heavy chain

<400> SEQUENCE: 36

Glu Met Gln Leu Val Glu Ser Gly Gly Gly Leu Val Gln Pro Lys Glu
1               5                   10                  15

Ser Leu Lys Ile Ser Cys Ala Ala Ser Gly Phe Thr Phe Asn Asn Ala
            20                  25                  30

Ala Met Tyr Trp Val Arg Gln Ala Pro Gly Lys Gly Leu Glu Trp Val
        35                  40                  45

Ala Arg Ile Arg Thr Lys Pro Asn Asn Tyr Ala Thr Ser Tyr Ala Asp
    50                  55                  60

Ser Val Lys Gly Arg Phe Thr Ile Ser Arg Asp Asp Ser Lys Ser Met
65                  70                  75                  80

Val Tyr Leu Gln Met Asp Asn Leu Lys Ser Glu Asp Thr Ala Met Tyr
                85                  90                  95

Tyr Cys Thr Ala Asp Tyr Ser Arg Gly Asp Arg Trp Gly Gln Gly Val
            100                 105                 110

Met Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
            180                 185                 190

Trp Pro Ser Glu Thr Val Thr Cys Asn Val Ala His Pro Ala Ser Ser
        195                 200                 205

Thr Lys Val Asp Lys Lys Ile Val Pro Arg Asp Cys His His His His
    210                 215                 220

His His His His His His
225                 230

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 37

Glu Glu Gly Ala Pro Gln Glu Gly Ile Leu
1               5                   10
```

```
<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 38

Gln Glu Gly Ile Leu Glu Asp Met Pro Val
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 39

Gly Ile Leu Glu Asp Met Pro Val Asp Pro
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 40

Leu Glu Asp Met Pro Val Asp Pro Asp Asn
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 41

Asp Met Pro Val Asp Pro Asp Asn Glu Ala
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 42

Pro Val Asp Pro Asp Asn Glu Ala Tyr Glu
1               5                   10
```

```
<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 43

Asp Pro Asp Asn Glu Ala Tyr Glu Met Pro
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 44

Asp Asn Glu Ala Tyr Glu Met Pro Ser Glu
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 45

Glu Ala Tyr Glu Met Pro Ser Glu Glu Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 46

Tyr Glu Met Pro Ser Glu Glu Gly Tyr Gln
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: fragment of C-terminus of alpha synuclein

<400> SEQUENCE: 47

Met Pro Ser Glu Glu Gly Tyr Gln Asp Tyr
```

```
<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His His His His His His His His His His
1               5                   10
```